US010799390B2

(12) United States Patent
Estreicher et al.

(10) Patent No.: US 10,799,390 B2
(45) Date of Patent: Oct. 13, 2020

(54) ENERGY HARVESTING, HEAT MANAGING, MULTI-EFFECT THERAPEUTIC GARMENT

(71) Applicant: New York Knitworks, LLC, New York, NY (US)

(72) Inventors: Sidney Samuel Estreicher, Hillsborough, NJ (US); Gabor Stein, New York, NY (US); George Joseph Szekely, Elkins Park, PA (US); Herbert Stevan Quinn, New York, NY (US)

(73) Assignee: New York Knitworks, LLC, New York, NY (US)

( * ) Notice: Subject to any disclaimer, the term of this patent is extended or adjusted under 35 U.S.C. 154(b) by 883 days.

(21) Appl. No.: 15/226,892

(22) Filed: Aug. 2, 2016

(65) Prior Publication Data

US 2017/0035605 A1 Feb. 9, 2017

Related U.S. Application Data

(60) Provisional application No. 62/200,124, filed on Aug. 3, 2015.

(51) Int. Cl.
| | | |
|---|---|---|
| *A61F 7/02* | (2006.01) | |
| *A61F 7/03* | (2006.01) | |
| *D02G 3/44* | (2006.01) | |
| *D04B 1/28* | (2006.01) | |
| *A61F 7/00* | (2006.01) | |

(52) U.S. Cl.
CPC .............. *A61F 7/02* (2013.01); *A61F 7/03* (2013.01); *D02G 3/44* (2013.01); *D04B 1/28* (2013.01);

(Continued)

(58) Field of Classification Search
CPC ............ D10B 2401/02; D10B 2401/04; D10B 2403/0114; D10B 2403/023;

(Continued)

(56) References Cited

U.S. PATENT DOCUMENTS

| | | |
|---|---|---|
| 6,373,034 B1 | 4/2002 | Rock et al. |
| 6,941,775 B2 | 9/2005 | Sharma |

(Continued)

FOREIGN PATENT DOCUMENTS

| | | |
|---|---|---|
| CA | 2908027 A1 | 10/2014 |
| EP | 1260355 A1 | 11/2002 |

(Continued)

OTHER PUBLICATIONS

Japan Exlan Co., Ltd., and Toyobo Specialties Trading Co., LTD. Exhibit at the International Textile Fair—"Preview in Seoul 2013"—</i> (Year: 2013).*

(Continued)

*Primary Examiner* — Eun Hwa Kim
*Assistant Examiner* — Adam Z Minchella
(74) *Attorney, Agent, or Firm* — Ashok Tankha

(57) ABSTRACT

An energy harvesting, heat managing, multi-effect therapeutic garment, defining an inner surface and an outer surface, seamlessly knitted using a predetermined number of yarns is provided. The yarns for constructing the therapeutic garment are selected from a yarn that absorbs, stores, and releases heat energy through a phase change, yarns that convert heat energy and ultra violet radiation energy into far infrared radiation energy and radiate the far infrared radiation energy to other yarns and to a wearer's body part, a yarn that adsorbs moisture from the wearer's body part and/or ambient environment and generates heat energy through an exothermic reaction, a heat insulating and hydrophobic yarn, and a heat conductive yarn that maintains a uniform temperature within the yarns. The yarns of the therapeutic garment are bundled and knitted to create a uniform surface area distribution of the yarns that contact each other and cover the wearer's body part.

11 Claims, 71 Drawing Sheets

(52) U.S. Cl.
CPC ............... *A61F 2007/0018* (2013.01); *A61F 2007/0036* (2013.01); *A61F 2007/0045* (2013.01); *A61F 2007/0088* (2013.01); *A61F 2007/0098* (2013.01); *A61F 2007/0233* (2013.01); *A61F 2007/0266* (2013.01); *D10B 2401/02* (2013.01); *D10B 2401/04* (2013.01); *D10B 2403/0114* (2013.01); *D10B 2403/0243* (2013.01)

(58) Field of Classification Search
CPC ............ D10B 2403/0234; D04B 1/28; A41D 19/01535; A41D 19/01576; A41D 31/102; A41D 31/065; A41D 31/04; A41D 13/002; D02G 3/44; A61F 7/02; A61F 7/03; A61F 2007/0018; A61F 2007/0036; A61F 2007/0045; A61F 2007/0088; A61F 2007/0098; A61F 2007/0233; A61F 2007/0266
See application file for complete search history.

(56) References Cited

U.S. PATENT DOCUMENTS

| | | | |
|---|---|---|---|
| 7,217,456 B1 | 5/2007 | Rock et al. | |
| 8,605,049 B2 | 12/2013 | Spencer | |
| 8,679,627 B2 | 3/2014 | Hartmann et al. | |
| 2008/0170982 A1* | 7/2008 | Zhang | C01B 32/15 423/447.3 |
| 2011/0162126 A1* | 7/2011 | Zhang | D04B 1/22 2/159 |
| 2013/0253397 A1* | 9/2013 | Samoodi | A41C 1/10 602/19 |
| 2015/0038040 A1 | 2/2015 | Gabbay | |
| 2018/0142383 A1* | 5/2018 | Minehardt | D02G 3/04 |

FOREIGN PATENT DOCUMENTS

| | | |
|---|---|---|
| JP | 2011214178 A | 10/2011 |
| KR | 20040061417 A | 7/2004 |
| KR | 20090026629 A | 3/2009 |
| WO | 2009031946 A1 | 3/2009 |
| WO | 2010006051 A1 | 1/2010 |
| WO | 2014152498 A1 | 9/2014 |
| WO | 2014199969 A1 | 12/2014 |

OTHER PUBLICATIONS

Japan Exlan Co., Ltd., and Toyobo Specialties Trading Co., LTD. Exhibit at the International Textile Fair—"Preview in Seoul 2013"—(Year: 2013).*

* cited by examiner

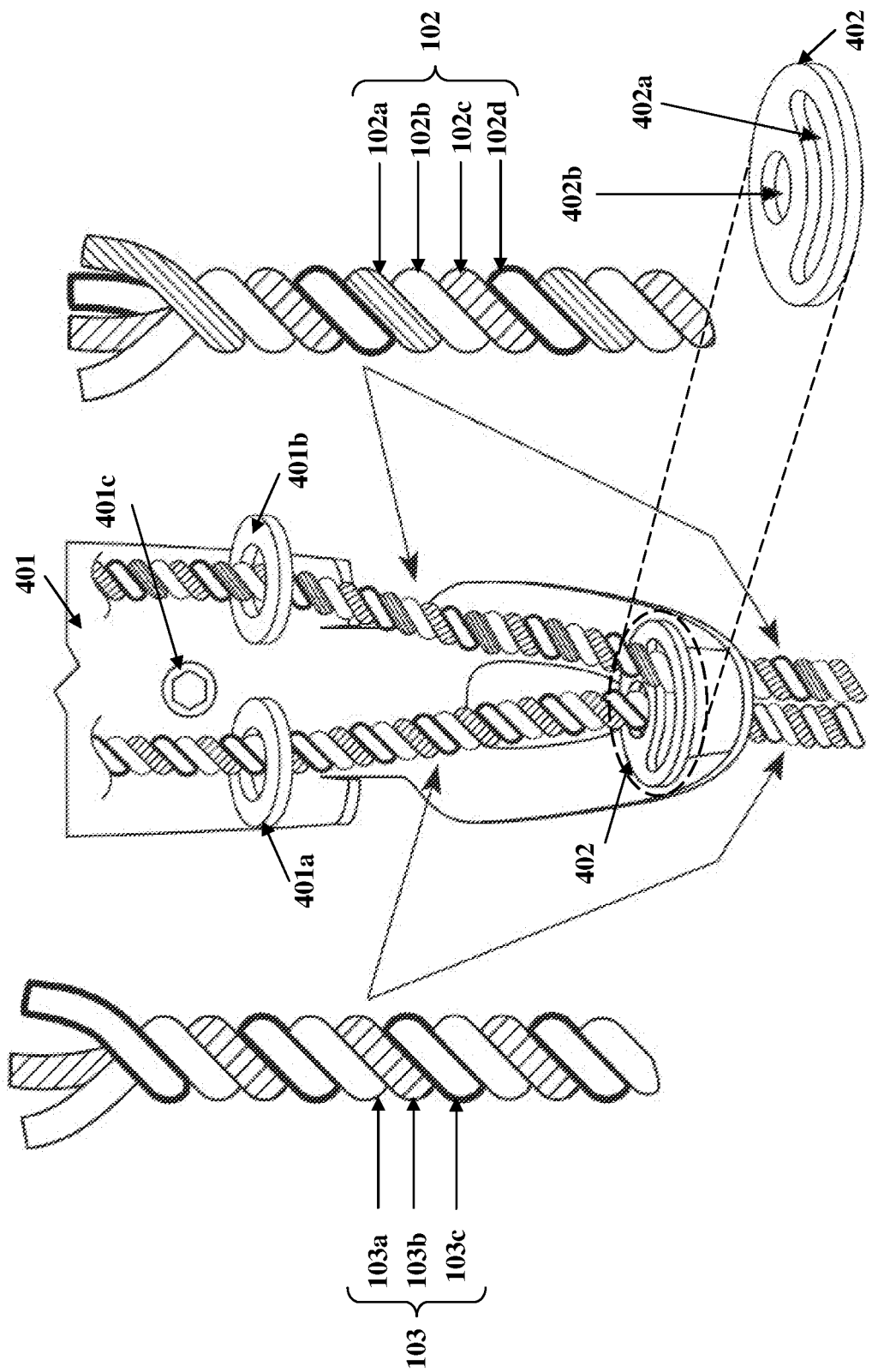

| TEST SAMPLE | ELEMENT 1 YARN | ELEMENT 2 YARN | ELEMENT 3 YARN | ELEMENT 6 YARN | SLOPE |
|---|---|---|---|---|---|
| A | 4 (320 den.) | 2 (312 den.) | 4 (760 den.) | - | -40 |
| B | 5 (400 den.) | 3 (468 den.) | 3 (570 den.) | - | -26 |
| C | 8 (640 den.) | 4 (624 den.) | - | - | -39 |
| D | 8 (640 den.) | - | 4 (760 den.) | - | -35 |
| E | - | 4 (624 den.) | 4 (760 den.) | - | -35 |
| F | - | - | 7 (1330 den.) | - | -76 |
| G | - | 8 (1248den.) | - | - | -58 |
| H | 17 (1360 den.) | - | - | - | -54 |
| I | 2 (160 den.) | 1 (156 den.) | 2 (380 den.) | 5 (630 den.) | -41 |

FIG. 8A

| TEST SAMPLE | ELEMENT 5 YARN | ELEMENT 3 YARN | SPANDEX | SLOPE |
|---|---|---|---|---|
| A | 1 (550 den.) | 3 (570 den.) | 1 (40 den.) | -40 |
| B | 1 (550 den.) | 3 (570 den.) | 1 (40 den.) | -26 |
| C | 1 (550 den.) | 3 (570 den.) | 1 (40 den.) | -39 |
| D | 1 (550 den.) | 3 (570 den.) | 1 (40 den.) | -35 |
| E | 1 (550 den.) | 3 (570 den.) | 1 (40 den.) | -35 |
| F | 1 (550 den.) | 3 (570 den.) | 1 (40 den.) | -76 |
| G | 1 (550 den.) | 3 (570 den.) | 1 (40 den.) | -58 |
| H | 1 (550 den.) | 3 (570 den.) | 1 (40 den.) | -54 |
| I | 1 (550 den.) | 3 (570 den.) | 1 (40 den.) | -41 |

FIG. 8B

| TIME | TECH SAMPLE A (°F) | TECH SAMPLE B (°F) |
|---|---|---|
| 2:08:06 PM | 91.3 | 91.3 |
| 2:08:21 PM | 91.4 | 91.9 |
| 2:08:36 PM | 91.5 | 92.1 |
| 2:08:51 PM | 91.4 | 91.6 |
| 2:09:06 PM | 90.8 | 90.8 |
| 2:09:21 PM | 90.9 | 89.9 |
| 2:09:36 PM | 91.1 | 90.3 |
| 2:09:51 PM | 91.4 | 91.1 |
| 2:10:06 PM | 91.6 | 90.5 |
| 2:10:21 PM | 91.8 | 90.8 |
| 2:10:36 PM | 92 | 91.2 |
| 2:10:51 PM | 92.1 | 91.5 |
| 2:11:06 PM | 92.1 | 91.8 |
| 2:11:21 PM | 92.2 | 92 |
| 2:11:36 PM | 92.2 | 92.1 |
| 2:11:51 PM | 92.3 | 92.3 |
| 2:12:06 PM | 92.3 | 92.4 |
| 2:12:21 PM | 92.3 | 92.5 |
| 2:12:36 PM | 92.2 | 92.6 |
| 2:12:51 PM | 92.1 | 92.6 |
| 2:13:06 PM | 92.1 | 92.7 |
| 2:13:21 PM | 92 | 92.8 |
| 2:13:36 PM | 91.9 | 92.8 |
| 2:13:51 PM | 91.9 | 92.9 |
| 2:14:06 PM | 91.9 | 92.9 |
| 2:14:21 PM | 91.9 | 93 |
| 2:14:36 PM | 91.9 | 93 |
| 2:14:51 PM | 91.8 | 93.1 |
| 2:15:06 PM | 91.8 | 93.1 |
| 2:15:21 PM | 91.7 | 93.2 |
| 2:15:36 PM | 91.7 | 93.2 |
| 2:15:51 PM | 91.7 | 93.2 |
| 2:16:06 PM | 91.7 | 93.3 |

FIG. 9A

| TIME | TECH SAMPLE A (°F) | TECH SAMPLE B (°F) |
| --- | --- | --- |
| 2:16:21 PM | 91.6 | 93.3 |
| 2:16:36 PM | 91.6 | 93.3 |
| 2:16:51 PM | 91.6 | 93.3 |
| 2:17:06 PM | 91.6 | 93.3 |
| 2:17:21 PM | 91.6 | 93.3 |
| 2:17:36 PM | 91.6 | 93.3 |
| 2:17:51 PM | 91.6 | 93.4 |
| 2:18:06 PM | 91.5 | 93.4 |
| 2:18:21 PM | 91.4 | 93.4 |
| 2:18:36 PM | 91.4 | 93.4 |
| 2:18:51 PM | 91.4 | 93.4 |
| 2:19:06 PM | 91.3 | 93.4 |
| 2:19:21 PM | 91.3 | 93.4 |
| 2:19:36 PM | 91.2 | 93.4 |
| 2:19:51 PM | 91 | 93.3 |
| 2:20:06 PM | 91.1 | 93.1 |
| 2:20:21 PM | 91.1 | 93 |
| 2:20:36 PM | 91.2 | 93 |
| 2:20:51 PM | 91.2 | 93 |
| 2:21:06 PM | 91.2 | 93 |
| 2:21:21 PM | 91.1 | 93 |
| 2:21:36 PM | 91.1 | 92.8 |
| 2:21:51 PM | 91.1 | 92.8 |
| 2:22:06 PM | 91 | 92.9 |
| 2:22:21 PM | 90.9 | 92.9 |
| 2:22:36 PM | 90.9 | 93.1 |
| 2:22:51 PM | 91 | 93.2 |
| 2:23:06 PM | 91 | 93.2 |
| 2:23:21 PM | 90.9 | 93.2 |
| 2:23:36 PM | 90.8 | 93.1 |
| 2:23:51 PM | 90.8 | 93.1 |
| 2:24:06 PM | 90.7 | 93.1 |
| 2:24:21 PM | 90.7 | 93.1 |

FIG. 9B

| TIME | TECH SAMPLE A (°F) | TECH SAMPLE B (°F) |
|---|---|---|
| 2:24:36 PM | 90.5 | 93 |
| 2:24:51 PM | 90.3 | 92.9 |
| 2:25:06 PM | 90.2 | 92.8 |
| 2:25:21 PM | 90.1 | 92.6 |
| 2:25:36 PM | 90.1 | 92.5 |
| 2:25:51 PM | 90.1 | 92.5 |
| 2:26:06 PM | 90.1 | 92.5 |
| 2:26:21 PM | 90 | 92.4 |
| 2:26:36 PM | 89.9 | 91.3 |
| 2:26:51 PM | 90.1 | 91.8 |
| 2:27:06 PM | 90.2 | 92.1 |
| 2:27:21 PM | 90.3 | 92.3 |
| 2:27:36 PM | 90.3 | 92.4 |
| 2:27:51 PM | 90.2 | 92.5 |
| 2:28:06 PM | 90.3 | 92.6 |
| 2:28:21 PM | 90.3 | 92.6 |
| 2:28:36 PM | 90.3 | 92.6 |
| 2:28:51 PM | 90.3 | 92.6 |
| 2:29:06 PM | 90.3 | 92.7 |
| 2:29:21 PM | 90.2 | 92.7 |
| 2:29:36 PM | 90.2 | 92.7 |
| 2:29:51 PM | 90.1 | 92.7 |
| 2:30:06 PM | 90.1 | 92.7 |
| 2:30:21 PM | 89.9 | 92.5 |
| 2:30:36 PM | 89.7 | 92.5 |
| 2:30:51 PM | 89.6 | 92.5 |
| 2:31:06 PM | 89.6 | 92.4 |
| 2:31:21 PM | 89.6 | 92.4 |
| 2:31:36 PM | 89.6 | 92.3 |
| 2:31:51 PM | 89.5 | 92.1 |
| 2:32:06 PM | 89.6 | 92.2 |
| 2:32:21 PM | 89.3 | 90.9 |
| 2:32:36 PM | 89.3 | 91.1 |
| 2:32:51 PM | 89.4 | 91.5 |

FIG. 9C

| TIME | TECH SAMPLE A (°F) | TECH SAMPLE B (°F) |
|---|---|---|
| 2:33:06 PM | 89.4 | 91.6 |
| 2:33:21 PM | 89.4 | 91.7 |
| 2:33:36 PM | 89.2 | 91.8 |
| 2:33:51 PM | 89.2 | 91.8 |
| 2:34:06 PM | 89.1 | 91.9 |
| 2:34:21 PM | 88.8 | 91.7 |
| 2:34:36 PM | 88.7 | 91.7 |
| 2:34:51 PM | 88.6 | 91.6 |
| 2:35:06 PM | 88.5 | 91.5 |
| 2:35:21 PM | 88.3 | 91.5 |
| 2:35:36 PM | 88.3 | 91.5 |
| 2:35:51 PM | 88.1 | 91.5 |
| 2:36:06 PM | 87.7 | 91.4 |
| 2:36:21 PM | 87.3 | 91.4 |
| 2:36:36 PM | 87.1 | 91.5 |
| 2:36:51 PM | 87.3 | 91.5 |
| 2:37:06 PM | 87.5 | 91.6 |
| 2:37:21 PM | 87.7 | 91.6 |
| 2:37:36 PM | 87.7 | 91.6 |
| 2:37:51 PM | 87.6 | 91.4 |
| 2:38:06 PM | 87.6 | 91.3 |
| 2:38:21 PM | 87.6 | 91.1 |
| 2:38:36 PM | 87.6 | 91 |
| 2:38:51 PM | 87.5 | 90.5 |
| 2:39:06 PM | 87.4 | 90.4 |
| 2:39:21 PM | 87.4 | 90.3 |
| 2:39:36 PM | 87.5 | 90.6 |
| 2:39:51 PM | 87.4 | 90.4 |
| 2:40:06 PM | 87.4 | 89.7 |
| 2:40:21 PM | 87.4 | 89.9 |
| 2:40:36 PM | 87.4 | 90.2 |
| 2:40:51 PM | 87.2 | 90.3 |
| 2:41:06 PM | 87.2 | 90.4 |

FIG. 9D

| TIME | TECH SAMPLE A (°F) | TECH SAMPLE B (°F) |
|---|---|---|
| 2:41:21 PM | 87.2 | 90.4 |
| 2:41:36 PM | 87.2 | 90.4 |
| 2:41:51 PM | 87.2 | 90.5 |
| 2:42:06 PM | 87.2 | 90.5 |
| 2:42:21 PM | 87.1 | 90.5 |
| 2:42:36 PM | 87.1 | 90.5 |
| 2:42:51 PM | 87 | 90.4 |
| 2:43:06 PM | 87.1 | 90.5 |
| 2:43:21 PM | 87.1 | 90.5 |
| 2:43:36 PM | 87 | 90.6 |
| 2:43:51 PM | 86.4 | 90.2 |
| 2:44:06 PM | 86.7 | 90.2 |
| 2:44:21 PM | 86.7 | 90.2 |
| 2:44:36 PM | 86.8 | 90 |
| 2:44:51 PM | 86.9 | 90 |
| 2:45:06 PM | 86.9 | 90 |
| 2:45:21 PM | 86.8 | 90 |
| 2:45:36 PM | 86.8 | 90.1 |
| 2:45:51 PM | 86.8 | 90.1 |
| 2:46:06 PM | 86.7 | 90.1 |
| 2:46:21 PM | 86.6 | 90.1 |
| 2:46:36 PM | 86.6 | 90.1 |
| 2:46:51 PM | 86.4 | 90.1 |
| 2:47:06 PM | 86.3 | 90.1 |
| 2:47:21 PM | 86.4 | 90.1 |
| 2:47:36 PM | 86.4 | 90 |
| 2:47:51 PM | 86.3 | 90 |
| 2:48:06 PM | 86.3 | 90 |
| 2:48:21 PM | 86.3 | 90 |
| 2:48:36 PM | 86.2 | 89.9 |
| 2:48:51 PM | 86.2 | 89.9 |
| 2:49:06 PM | 86.1 | 89.8 |
| 2:49:21 PM | 86 | 89.7 |

FIG. 9E

| TIME | TECH SAMPLE A (°F) | TECH SAMPLE B (°F) |
| --- | --- | --- |
| 2:49:36 PM | 86.1 | 89.7 |
| 2:49:51 PM | 86.1 | 89.8 |
| 2:50:06 PM | 86 | 89.8 |
| 2:50:21 PM | 85.9 | 89.8 |
| 2:50:36 PM | 85.8 | 89.8 |
| 2:50:51 PM | 85.8 | 89.6 |
| 2:51:06 PM | 85.9 | 89.6 |
| 2:51:21 PM | 86 | 89.5 |
| 2:51:36 PM | 85.9 | 89.4 |
| 2:51:51 PM | 85.9 | 89.4 |
| 2:52:06 PM | 85.9 | 89.4 |
| 2:52:21 PM | 85.8 | 89.3 |
| 2:52:36 PM | 85.5 | 88.8 |
| 2:52:51 PM | 85.5 | 88.6 |
| 2:53:06 PM | 85.4 | 88.6 |
| 2:53:21 PM | 85.4 | 88.6 |
| 2:53:36 PM | 85.3 | 88.6 |
| 2:53:51 PM | 85.2 | 88.6 |
| 2:54:06 PM | 85.3 | 88.6 |
| 2:54:21 PM | 85.4 | 88.7 |
| 2:54:36 PM | 85.3 | 88.7 |
| 2:54:51 PM | 85.3 | 88.6 |
| 2:55:06 PM | 85.3 | 88.6 |
| 2:55:21 PM | 85.2 | 88.6 |
| 2:55:36 PM | 85.2 | 88.6 |
| 2:55:51 PM | 85.1 | 88.6 |
| 2:56:06 PM | 85.1 | 88.7 |
| 2:56:21 PM | 85.1 | 88.8 |
| 2:56:36 PM | 85 | 88.8 |
| 2:56:51 PM | 85 | 88.8 |
| 2:57:06 PM | 84.9 | 88.8 |
| 2:57:21 PM | 84.8 | 88.8 |
| 2:57:36 PM | 84.9 | 88.6 |

FIG. 9F

| TIME | TECH SAMPLE A (°F) | TECH SAMPLE B (°F) |
| --- | --- | --- |
| 2:57:51 PM | 84.8 | 88.5 |
| 2:58:06 PM | 84.8 | 88.5 |
| 2:58:21 PM | 84.7 | 88.5 |
| 2:58:36 PM | 84.7 | 88.5 |
| 2:58:51 PM | 84.6 | 88.5 |
| 2:59:06 PM | 84.6 | 88.5 |
| 2:59:21 PM | 84.5 | 88.5 |
| 2:59:36 PM | 84.5 | 88.5 |
| 2:59:51 PM | 84.4 | 88.5 |
| 3:00:06 PM | 84.4 | 88.5 |
| 3:00:21 PM | 84.4 | 88.5 |
| 3:00:36 PM | 84.3 | 88.5 |
| 3:00:51 PM | 84.3 | 88.3 |
| 3:01:06 PM | 84.3 | 88.2 |
| 3:01:21 PM | 84.4 | 88.1 |
| 3:01:36 PM | 84.3 | 88.1 |
| 3:01:51 PM | 84.3 | 88.1 |
| 3:02:06 PM | 84.2 | 87.9 |
| 3:02:21 PM | 84.2 | 87.8 |
| 3:02:36 PM | 84.1 | 87.8 |
| 3:02:51 PM | 84.1 | 87.8 |
| 3:03:06 PM | 84.1 | 87.7 |
| 3:03:21 PM | 84 | 87.7 |
| 3:03:36 PM | 84 | 87.6 |
| 3:03:51 PM | 83.9 | 87.5 |
| 3:04:06 PM | 84 | 87.4 |
| 3:04:21 PM | 84 | 87.4 |
| 3:04:36 PM | 84 | 87.3 |
| 3:04:51 PM | 83.9 | 87.3 |
| 3:05:06 PM | 83.8 | 87.3 |
| 3:05:21 PM | 83.8 | 87.2 |
| 3:05:36 PM | 83.8 | 87.2 |
| 3:05:51 PM | 83.7 | 87.1 |

FIG. 9G

| TIME | TECH SAMPLE A (°F) | TECH SAMPLE B (°F) |
|---|---|---|
| 3:06:06 PM | 83.8 | 87.1 |
| 3:06:21 PM | 83.8 | 87.1 |
| 3:06:36 PM | 83.8 | 87 |
| 3:06:51 PM | 81.2 | 84 |
| 3:07:06 PM | 82.2 | 84 |
| 3:07:21 PM | 81.7 | 82.8 |

FIG. 9H

| TIME | TECH SAMPLE D (°F) | TECH SAMPLE C (°F) |
| --- | --- | --- |
| 2:18:44 PM | 79.9 | 78.6 |
| 2:18:59 PM | 79.7 | 79 |
| 2:19:14 PM | 80.2 | 79.9 |
| 2:19:29 PM | 80.4 | 79.9 |
| 2:19:44 PM | 78.9 | 78.8 |
| 2:19:59 PM | 79.5 | 78.6 |
| 2:20:14 PM | 78.4 | 76.9 |
| 2:20:29 PM | 78.6 | 79.3 |
| 2:20:44 PM | 78.8 | 80 |
| 2:20:59 PM | 79.2 | 80.4 |
| 2:21:14 PM | 79.4 | 81 |
| 2:21:29 PM | 79.5 | 81.3 |
| 2:21:44 PM | 79.6 | 81.5 |
| 2:21:59 PM | 79.7 | 81.4 |
| 2:22:14 PM | 79.8 | 81.2 |
| 2:22:29 PM | 80.1 | 81.4 |
| 2:22:44 PM | 80.2 | 81.8 |
| 2:22:59 PM | 80 | 81.9 |
| 2:23:14 PM | 80.1 | 81.9 |
| 2:23:29 PM | 80.2 | 82 |
| 2:23:44 PM | 80.2 | 82.2 |
| 2:23:59 PM | 80.3 | 82.3 |
| 2:24:14 PM | 80.6 | 82.6 |
| 2:24:29 PM | 80.7 | 82.8 |
| 2:24:44 PM | 80.7 | 82.9 |
| 2:24:59 PM | 80.8 | 83.1 |
| 2:25:14 PM | 81.1 | 83.1 |
| 2:25:29 PM | 81.2 | 83.2 |
| 2:25:44 PM | 81.3 | 83 |
| 2:25:59 PM | 81.3 | 83.2 |
| 2:26:14 PM | 81.2 | 83.3 |
| 2:26:29 PM | 81.1 | 82.7 |

FIG. 10A

| TIME | TECH SAMPLE D (°F) | TECH SAMPLE C (°F) |
|---|---|---|
| 2:26:44 PM | 81.1 | 83 |
| 2:26:59 PM | 81.1 | 82.1 |
| 2:27:14 PM | 81.2 | 83 |
| 2:27:29 PM | 81.4 | 83.3 |
| 2:27:44 PM | 81.4 | 83.4 |
| 2:27:59 PM | 81.4 | 83.5 |
| 2:28:14 PM | 81.4 | 83.6 |
| 2:28:29 PM | 81.3 | 83.8 |
| 2:28:44 PM | 81.5 | 83.9 |
| 2:28:59 PM | 81.6 | 84 |
| 2:29:14 PM | 81.5 | 84 |
| 2:29:29 PM | 81.6 | 84 |
| 2:29:44 PM | 81.6 | 83.6 |
| 2:29:59 PM | 82 | 84.3 |
| 2:30:14 PM | 82.2 | 84.5 |
| 2:30:29 PM | 82.3 | 84.6 |
| 2:30:44 PM | 82.1 | 84.6 |
| 2:30:59 PM | 82 | 84.6 |
| 2:31:14 PM | 82 | 84.4 |
| 2:31:29 PM | 81.7 | 84 |
| 2:31:44 PM | 81.7 | 84.4 |
| 2:31:59 PM | 81.6 | 82.3 |
| 2:32:14 PM | 81.4 | 82.2 |
| 2:32:29 PM | 81.6 | 81.7 |
| 2:32:44 PM | 81.8 | 81.7 |
| 2:32:59 PM | 81.7 | 81.7 |
| 2:33:14 PM | 81.5 | 81.6 |
| 2:33:29 PM | 81.3 | 81.4 |
| 2:33:44 PM | 81.3 | 82.2 |
| 2:33:59 PM | 81.1 | 82.4 |
| 2:34:14 PM | 80.8 | 81.1 |
| 2:34:29 PM | 80.6 | 81.2 |

FIG. 10B

| TIME | TECH SAMPLE D (°F) | TECH SAMPLE C (°F) |
|---|---|---|
| 2:34:44 PM | 80.3 | 81.2 |
| 2:34:59 PM | 80.4 | 81.4 |
| 2:35:14 PM | 80.4 | 80.8 |
| 2:35:29 PM | 80.2 | 80.1 |
| 2:35:44 PM | 80 | 79.8 |
| 2:35:59 PM | 80.1 | 81.3 |
| 2:36:14 PM | 80.4 | 82.6 |
| 2:36:29 PM | 80.8 | 83.3 |
| 2:36:44 PM | 80.9 | 83.2 |
| 2:36:59 PM | 80.9 | 82.6 |
| 2:37:14 PM | 80.8 | 82.3 |
| 2:37:29 PM | 80.9 | 82 |
| 2:37:44 PM | 80.9 | 81.8 |
| 2:37:59 PM | 81 | 82.1 |
| 2:38:14 PM | 81 | 82.2 |
| 2:38:29 PM | 80.9 | 82.3 |
| 2:38:44 PM | 80.9 | 82.7 |
| 2:38:59 PM | 80.9 | 82.5 |
| 2:39:14 PM | 80.9 | 82.2 |
| 2:39:29 PM | 80.8 | 81.5 |
| 2:39:44 PM | 80.8 | 79.1 |
| 2:39:59 PM | 80.7 | 78.9 |
| 2:40:14 PM | 80.7 | 77.3 |
| 2:40:29 PM | 80.7 | 77 |
| 2:40:44 PM | 80.6 | 76.4 |
| 2:40:59 PM | 80.7 | 76.6 |
| 2:41:14 PM | 80.9 | 78 |
| 2:41:29 PM | 81 | 79.1 |
| 2:41:44 PM | 81.1 | 78.1 |
| 2:41:59 PM | 81 | 77.6 |
| 2:42:14 PM | 80.8 | 77.1 |
| 2:42:29 PM | 80.7 | 76.9 |
| 2:42:44 PM | 80.7 | 79.8 |

FIG. 10C

| TIME | TECH SAMPLE D (°F) | TECH SAMPLE C (°F) |
|---|---|---|
| 2:42:59 PM | 80.6 | 79.1 |
| 2:43:14 PM | 80.2 | 78.8 |
| 2:43:29 PM | 79.7 | 77.4 |
| 2:43:44 PM | 80.3 | 80.4 |
| 2:43:59 PM | 80.1 | 79.9 |
| 2:44:14 PM | 80 | 81.6 |
| 2:44:29 PM | 80.2 | 81.7 |
| 2:44:44 PM | 80.3 | 81.3 |
| 2:44:59 PM | 80.3 | 80.3 |
| 2:45:14 PM | 80.3 | 80.3 |
| 2:45:29 PM | 80.2 | 78.7 |
| 2:45:44 PM | 80 | 77.5 |
| 2:45:59 PM | 79.7 | 77 |
| 2:46:14 PM | 79.6 | 77.1 |
| 2:46:29 PM | 79.4 | 75.9 |
| 2:46:44 PM | 79.5 | 77.4 |
| 2:46:59 PM | 79.6 | 80 |
| 2:47:14 PM | 79.8 | 80.6 |
| 2:47:29 PM | 79.9 | 80.8 |
| 2:47:44 PM | 79.9 | 79.2 |
| 2:47:59 PM | 79.7 | 80.6 |
| 2:48:14 PM | 79.8 | 80.8 |
| 2:48:29 PM | 79.8 | 81 |
| 2:48:44 PM | 79.7 | 81.1 |
| 2:48:59 PM | 79.6 | 80.7 |
| 2:49:14 PM | 79.5 | 81.5 |
| 2:49:29 PM | 79.7 | 81.7 |
| 2:49:44 PM | 79.8 | 81.6 |
| 2:49:59 PM | 79.7 | 81.7 |
| 2:50:14 PM | 79.8 | 81.7 |
| 2:50:29 PM | 79.8 | 81.8 |
| 2:50:44 PM | 79.7 | 81.5 |
| 2:50:59 PM | 79.6 | 80.4 |

FIG. 10D

| TIME | TECH SAMPLE D (°F) | TECH SAMPLE C (°F) |
| --- | --- | --- |
| 2:51:14 PM | 79.5 | 79.7 |
| 2:51:29 PM | 79.6 | 79.9 |
| 2:51:44 PM | 79.5 | 80.2 |
| 2:51:59 PM | 79.6 | 80.7 |
| 2:52:14 PM | 79.6 | 80.6 |
| 2:52:29 PM | 79.6 | 81.9 |
| 2:52:44 PM | 79.6 | 82 |
| 2:52:59 PM | 79.4 | 82.1 |
| 2:53:14 PM | 79.3 | 81.8 |
| 2:53:29 PM | 79.2 | 81.5 |
| 2:53:44 PM | 78.9 | 81.2 |
| 2:53:59 PM | 78.8 | 80.9 |
| 2:54:14 PM | 78.7 | 80.7 |
| 2:54:29 PM | 78.4 | 80.8 |
| 2:54:44 PM | 78.7 | 80.4 |
| 2:54:59 PM | 78.6 | 80 |
| 2:55:14 PM | 78.4 | 77.6 |
| 2:55:29 PM | 78.1 | 76.9 |
| 2:55:44 PM | 77.8 | 77.1 |
| 2:55:59 PM | 77.9 | 78.1 |
| 2:56:14 PM | 77.7 | 77.3 |
| 2:56:29 PM | 77.6 | 77.2 |
| 2:56:44 PM | 77.5 | 77.4 |
| 2:56:59 PM | 77.4 | 77.6 |
| 2:57:14 PM | 77.3 | 77.5 |
| 2:57:29 PM | 77.2 | 77.3 |
| 2:57:44 PM | 77.1 | 78.3 |
| 2:57:59 PM | 77 | 78.4 |
| 2:58:14 PM | 76.8 | 77.9 |
| 2:58:29 PM | 76.8 | 77.8 |
| 2:58:44 PM | 76.7 | 76.8 |
| 2:58:59 PM | 76.4 | 78.4 |
| 2:59:14 PM | 76.2 | 78.7 |

FIG. 10E

| TIME | TECH SAMPLE D (°F) | TECH SAMPLE C (°F) |
|---|---|---|
| 2:59:29 PM | 76.2 | 78.9 |
| 2:59:44 PM | 76.1 | 78.7 |
| 2:59:59 PM | 76 | 78.9 |
| 3:00:14 PM | 76 | 80 |
| 3:00:29 PM | 76.3 | 80.3 |
| 3:00:44 PM | 76.6 | 80.6 |
| 3:00:59 PM | 76.6 | 80 |
| 3:01:14 PM | 76.5 | 79.1 |
| 3:01:29 PM | 76.5 | 78.7 |
| 3:01:44 PM | 76.5 | 78.4 |
| 3:01:59 PM | 76.5 | 78.4 |
| 3:02:14 PM | 76.4 | 78.1 |
| 3:02:29 PM | 76.4 | 78.1 |
| 3:02:44 PM | 76.4 | 78.8 |
| 3:02:59 PM | 76.3 | 78.3 |
| 3:03:14 PM | 76.4 | 77.6 |
| 3:03:29 PM | 76.5 | 77.7 |
| 3:03:44 PM | 76.6 | 79.5 |
| 3:03:59 PM | 76.7 | 79.1 |
| 3:04:14 PM | 76.7 | 79.1 |
| 3:04:29 PM | 76.8 | 79.1 |
| 3:04:44 PM | 76.7 | 79 |
| 3:04:59 PM | 76.6 | 78.6 |
| 3:05:14 PM | 76.6 | 78.4 |
| 3:05:29 PM | 76.5 | 78.1 |
| 3:05:44 PM | 76.5 | 78.2 |
| 3:05:59 PM | 76.5 | 78.1 |
| 3:06:14 PM | 76.5 | 78 |
| 3:06:29 PM | 76.4 | 77.7 |
| 3:06:44 PM | 76.4 | 76 |
| 3:06:59 PM | 76.6 | 73.9 |
| 3:07:14 PM | 75.7 | 66.1 |
| 3:07:29 PM | 75.5 | 74.5 |

FIG. 10F

| TIME | TECH SAMPLE D (°F) | TECH SAMPLE C (°F) |
|---|---|---|
| 3:07:44 PM | 75.6 | 75.8 |
| 3:07:59 PM | 75 | 75.7 |
| 3:08:14 PM | 74.9 | 76.6 |
| 3:08:29 PM | 74.6 | 75.6 |
| 3:08:44 PM | 74.5 | 76.5 |
| 3:08:59 PM | 74.4 | 76.3 |
| 3:09:14 PM | 74.4 | 76.3 |
| 3:09:29 PM | 74.3 | 76.4 |
| 3:09:44 PM | 74.1 | 75.8 |
| 3:09:59 PM | 74 | 76.3 |
| 3:10:14 PM | 73.7 | 76.2 |
| 3:10:29 PM | 73.6 | 76.3 |
| 3:10:44 PM | 73.7 | 76.6 |
| 3:10:59 PM | 73.7 | 76.9 |
| 3:11:14 PM | 74 | 76.6 |
| 3:11:29 PM | 74.3 | 76.6 |
| 3:11:44 PM | 74.4 | 76.1 |
| 3:11:59 PM | 74.6 | 75.5 |
| 3:12:14 PM | 74.6 | 72.7 |
| 3:12:29 PM | 74.6 | 74.1 |
| 3:12:44 PM | 74.5 | 73.8 |
| 3:12:59 PM | 74.5 | 74.7 |
| 3:13:14 PM | 74.5 | 74.1 |
| 3:13:29 PM | 74.5 | 73.8 |
| 3:13:44 PM | 74.5 | 74.2 |
| 3:13:59 PM | 74.4 | 73.7 |
| 3:14:14 PM | 74.4 | 75.1 |
| 3:14:29 PM | 74.4 | 74.3 |
| 3:14:44 PM | 74.3 | 74.2 |
| 3:14:59 PM | 74.2 | 74.3 |
| 3:15:14 PM | 73.3 | 64.3 |
| 3:15:29 PM | 72.6 | 70.4 |
| 3:15:44 PM | 72.6 | 73.1 |
| 3:15:59 PM | 72.9 | 73.3 |

FIG. 10G

| TIME | TECH SAMPLE D (°F) | TECH SAMPLE C (°F) |
|---|---|---|
| 3:16:14 PM | 73.1 | 70.5 |
| 3:16:29 PM | 73.1 | 73 |
| 3:16:44 PM | 73.2 | 73.9 |
| 3:16:59 PM | 73.3 | 73.5 |
| 3:17:14 PM | 73.1 | 65.8 |
| 3:17:29 PM | 73.1 | 67.7 |
| 3:17:44 PM | 71.9 | 67 |
| 3:17:59 PM | 72.2 | 70.1 |
| 3:18:14 PM | 72.5 | 71.5 |

FIG. 10H

| TIME | TEST SAMPLE E (°F) |
|---|---|
| 11:14:15 AM | 86.6 |
| 11:14:30 AM | 86.7 |
| 11:14:45 AM | 87 |
| 11:15:00 AM | 86.6 |
| 11:15:15 AM | 85.9 |
| 11:15:30 AM | 85.3 |
| 11:15:45 AM | 84.3 |
| 11:16:00 AM | 84.4 |
| 11:16:15 AM | 85.1 |
| 11:16:30 AM | 85.9 |
| 11:16:45 AM | 86.3 |
| 11:17:00 AM | 86.7 |
| 11:17:15 AM | 86.8 |
| 11:17:30 AM | 86.8 |
| 11:17:45 AM | 86.9 |
| 11:18:00 AM | 86.9 |
| 11:18:15 AM | 86.8 |
| 11:18:30 AM | 86.8 |
| 11:18:45 AM | 86.8 |
| 11:19:00 AM | 86.8 |
| 11:19:15 AM | 86.8 |
| 11:19:30 AM | 86.8 |
| 11:19:45 AM | 87 |
| 11:20:00 AM | 86.6 |
| 11:20:15 AM | 86.6 |
| 11:20:30 AM | 86.6 |
| 11:20:45 AM | 86.7 |
| 11:21:00 AM | 86.7 |
| 11:21:15 AM | 86.8 |
| 11:21:30 AM | 86.8 |
| 11:21:45 AM | 86.8 |
| 11:22:00 AM | 86.8 |

FIG. 11A

| TIME | TEST SAMPLE E (°F) |
|---|---|
| 11:22:15 AM | 86.7 |
| 11:22:30 AM | 86.7 |
| 11:22:45 AM | 86.7 |
| 11:23:00 AM | 86.7 |
| 11:23:15 AM | 86.8 |
| 11:23:30 AM | 86.7 |
| 11:23:45 AM | 86.8 |
| 11:24:00 AM | 86.8 |
| 11:24:15 AM | 86.9 |
| 11:24:30 AM | 87 |
| 11:24:45 AM | 86.9 |
| 11:25:00 AM | 87 |
| 11:25:15 AM | 87 |
| 11:25:30 AM | 87 |
| 11:25:45 AM | 87 |
| 11:26:00 AM | 87 |
| 11:26:15 AM | 87 |
| 11:26:30 AM | 87.1 |
| 11:26:45 AM | 87.3 |
| 11:27:00 AM | 87.5 |
| 11:27:15 AM | 87.6 |
| 11:27:30 AM | 87.7 |
| 11:27:45 AM | 87.7 |
| 11:28:00 AM | 87.7 |
| 11:28:15 AM | 87.8 |
| 11:28:30 AM | 87.8 |
| 11:28:45 AM | 87.9 |
| 11:29:00 AM | 88 |
| 11:29:15 AM | 87.9 |
| 11:29:30 AM | 87.7 |
| 11:29:45 AM | 88 |
| 11:30:00 AM | 88.2 |

FIG. 11B

| TIME | TEST SAMPLE E (°F) |
|---|---|
| 11:30:15 AM | 88.2 |
| 11:30:30 AM | 88.1 |
| 11:30:45 AM | 88.1 |
| 11:31:00 AM | 88 |
| 11:31:15 AM | 88 |
| 11:31:30 AM | 88 |
| 11:31:45 AM | 87.8 |
| 11:32:00 AM | 87.7 |
| 11:32:15 AM | 87.6 |
| 11:32:30 AM | 87.5 |
| 11:32:45 AM | 87.4 |
| 11:33:00 AM | 87.4 |
| 11:33:15 AM | 87.4 |
| 11:33:30 AM | 87.5 |
| 11:33:45 AM | 87.6 |
| 11:34:00 AM | 87.7 |
| 11:34:15 AM | 87.6 |
| 11:34:30 AM | 87.5 |
| 11:34:45 AM | 87.5 |
| 11:35:00 AM | 87.5 |
| 11:35:15 AM | 87.5 |
| 11:35:30 AM | 87.4 |
| 11:35:45 AM | 87.5 |
| 11:36:00 AM | 87.6 |
| 11:36:15 AM | 87.6 |
| 11:36:30 AM | 87.6 |
| 11:36:45 AM | 87.5 |
| 11:37:00 AM | 87.5 |
| 11:37:15 AM | 87.4 |
| 11:37:30 AM | 87.2 |
| 11:37:45 AM | 87.1 |
| 11:38:00 AM | 87 |

FIG. 11C

| TIME | TEST SAMPLE E (°F) |
|---|---|
| 11:38:15 AM | 86.8 |
| 11:38:30 AM | 86.7 |
| 11:38:45 AM | 86.6 |
| 11:39:00 AM | 86.4 |
| 11:39:15 AM | 86.3 |
| 11:39:30 AM | 86.1 |
| 11:39:45 AM | 86.3 |
| 11:40:00 AM | 86.4 |
| 11:40:15 AM | 86.4 |
| 11:40:30 AM | 86.1 |
| 11:40:45 AM | 86.3 |
| 11:41:00 AM | 86.4 |
| 11:41:15 AM | 86.4 |
| 11:41:30 AM | 86.6 |
| 11:41:45 AM | 86.7 |
| 11:42:00 AM | 86.7 |
| 11:42:15 AM | 86.8 |
| 11:42:30 AM | 86.6 |
| 11:42:45 AM | 86.4 |
| 11:43:00 AM | 86.1 |
| 11:43:15 AM | 85.8 |
| 11:43:30 AM | 86 |
| 11:43:45 AM | 86.1 |
| 11:44:00 AM | 86 |
| 11:44:15 AM | 85.1 |
| 11:44:30 AM | 85.3 |
| 11:44:45 AM | 85.5 |
| 11:45:00 AM | 85.2 |
| 11:45:15 AM | 85.3 |
| 11:45:30 AM | 85.3 |
| 11:45:45 AM | 85.2 |
| 11:46:00 AM | 85.1 |

FIG. 11D

| TIME | TEST SAMPLE E (°F) |
|---|---|
| 11:46:15 AM | 85 |
| 11:46:30 AM | 84.9 |
| 11:46:45 AM | 84.8 |
| 11:47:00 AM | 84.7 |
| 11:47:15 AM | 84.8 |
| 11:47:30 AM | 84.7 |
| 11:47:45 AM | 84.7 |
| 11:48:00 AM | 84.8 |
| 11:48:15 AM | 84.7 |
| 11:48:30 AM | 84.6 |
| 11:48:45 AM | 84.4 |
| 11:49:00 AM | 84.3 |
| 11:49:15 AM | 84.3 |
| 11:49:30 AM | 84.2 |
| 11:49:45 AM | 84.2 |
| 11:50:00 AM | 84.1 |
| 11:50:15 AM | 84.1 |
| 11:50:30 AM | 84.1 |
| 11:50:45 AM | 83.9 |
| 11:51:00 AM | 83.8 |
| 11:51:15 AM | 83.7 |
| 11:51:30 AM | 83.8 |
| 11:51:45 AM | 83.9 |
| 11:52:00 AM | 83.9 |
| 11:52:15 AM | 83.7 |
| 11:52:30 AM | 83.7 |
| 11:52:45 AM | 83.7 |
| 11:53:00 AM | 83.6 |
| 11:53:15 AM | 83.5 |
| 11:53:30 AM | 83.5 |
| 11:53:45 AM | 83.5 |
| 11:54:00 AM | 83.6 |

FIG. 11E

| TIME | TEST SAMPLE E (°F) |
|---|---|
| 11:54:15 AM | 83.5 |
| 11:54:30 AM | 83.5 |
| 11:54:45 AM | 83.4 |
| 11:55:00 AM | 83.3 |
| 11:55:15 AM | 83.3 |
| 11:55:30 AM | 83.3 |
| 11:55:45 AM | 83.1 |
| 11:56:00 AM | 83.1 |
| 11:56:15 AM | 83.3 |
| 11:56:30 AM | 83.3 |
| 11:56:45 AM | 83.3 |
| 11:57:00 AM | 83.3 |
| 11:57:15 AM | 83.2 |
| 11:57:30 AM | 83.2 |
| 11:57:45 AM | 83.1 |
| 11:58:00 AM | 83 |
| 11:58:15 AM | 82.9 |
| 11:58:30 AM | 82.8 |
| 11:58:45 AM | 82.7 |
| 11:59:00 AM | 82.6 |
| 11:59:15 AM | 82.6 |
| 11:59:30 AM | 82.5 |
| 11:59:45 AM | 82 |
| 12:00:00 PM | 81.9 |
| 12:00:15 PM | 82.1 |
| 12:00:30 PM | 82.2 |
| 12:00:45 PM | 82 |
| 12:01:00 PM | 82 |
| 12:01:15 PM | 82 |
| 12:01:30 PM | 82 |
| 12:01:45 PM | 82 |
| 12:02:00 PM | 82.1 |

FIG. 11F

| TIME | TEST SAMPLE E (°F) |
|---|---|
| 12:02:15 PM | 82 |
| 12:02:30 PM | 82 |
| 12:02:45 PM | 80.9 |
| 12:03:00 PM | 79.1 |
| 12:03:15 PM | 79.8 |
| 12:03:30 PM | 80.2 |
| 12:03:45 PM | 80.6 |
| 12:04:00 PM | 80.7 |
| 12:04:15 PM | 80.7 |
| 12:04:30 PM | 80.7 |
| 12:04:45 PM | 80.8 |
| 12:05:00 PM | 80.9 |
| 12:05:15 PM | 80.9 |
| 12:05:30 PM | 80.8 |
| 12:05:45 PM | 80.7 |
| 12:06:00 PM | 80.3 |
| 12:06:15 PM | 80.4 |
| 12:06:30 PM | 80.6 |
| 12:06:45 PM | 80.6 |
| 12:07:00 PM | 80.6 |
| 12:07:15 PM | 79.6 |
| 12:07:30 PM | 79.7 |
| 12:07:45 PM | 80 |
| 12:08:00 PM | 80 |
| 12:08:15 PM | 80 |
| 12:08:30 PM | 80.1 |
| 12:08:45 PM | 80.1 |
| 12:09:00 PM | 80 |
| 12:09:15 PM | 80.1 |
| 12:09:30 PM | 80.1 |
| 12:09:45 PM | 80.1 |
| 12:10:00 PM | 80.2 |

FIG. 11G

| TIME | TEST SAMPLE E (°F) |
|---|---|
| 12:10:15 PM | 80.1 |
| 12:10:30 PM | 80 |
| 12:10:45 PM | 80 |
| 12:11:00 PM | 79.9 |
| 12:11:15 PM | 79.9 |
| 12:11:30 PM | 79.8 |
| 12:11:45 PM | 79.8 |
| 12:12:00 PM | 79.7 |
| 12:12:15 PM | 79.8 |
| 12:12:30 PM | 79.8 |
| 12:12:45 PM | 79.8 |
| 12:13:00 PM | 79.8 |
| 12:13:15 PM | 79.8 |
| 12:13:30 PM | 79.7 |
| 12:13:45 PM | 78.5 |
| 12:14:00 PM | 78.4 |

FIG. 11H

| TIME | TECH SAMPLE F (°F) |
|---|---|
| 10:38:55 AM | 87.4 |
| 10:39:10 AM | 87.4 |
| 10:39:25 AM | 87.6 |
| 10:39:40 AM | 87.6 |
| 10:39:55 AM | 86 |
| 10:40:10 AM | 87.2 |
| 10:40:25 AM | 87.6 |
| 10:40:40 AM | 87.8 |
| 10:40:55 AM | 87.2 |
| 10:41:10 AM | 87.6 |
| 10:41:25 AM | 87.8 |
| 10:41:40 AM | 87.8 |
| 10:41:55 AM | 87.9 |
| 10:42:10 AM | 87.5 |
| 10:42:25 AM | 87.8 |
| 10:42:40 AM | 87.7 |
| 10:42:55 AM | 87.8 |
| 10:43:10 AM | 87.9 |
| 10:43:25 AM | 87.9 |
| 10:43:40 AM | 88 |
| 10:43:55 AM | 88 |
| 10:44:10 AM | 88.1 |
| 10:44:25 AM | 88.1 |
| 10:44:40 AM | 87.7 |
| 10:44:55 AM | 87.9 |
| 10:45:10 AM | 87.9 |
| 10:45:25 AM | 87.9 |
| 10:45:40 AM | 88 |
| 10:45:55 AM | 88 |
| 10:46:10 AM | 88 |
| 10:46:25 AM | 88.1 |
| 10:46:40 AM | 88.2 |
| 10:46:55 AM | 88 |

FIG. 12A

| TIME | TECH SAMPLE F (°F) |
|---|---|
| 10:47:10 AM | 88.2 |
| 10:47:25 AM | 88.3 |
| 10:47:40 AM | 88.4 |
| 10:47:55 AM | 88.4 |
| 10:48:10 AM | 88.4 |
| 10:48:25 AM | 88.6 |
| 10:48:40 AM | 88.6 |
| 10:48:55 AM | 88.5 |
| 10:49:10 AM | 88.6 |
| 10:49:25 AM | 88.3 |
| 10:49:40 AM | 88.2 |
| 10:49:55 AM | 88.2 |
| 10:50:10 AM | 88.2 |
| 10:50:25 AM | 88.1 |
| 10:50:40 AM | 88 |
| 10:50:55 AM | 87.3 |
| 10:51:10 AM | 87.4 |
| 10:51:25 AM | 87.4 |
| 10:51:40 AM | 87.5 |
| 10:51:55 AM | 87.6 |
| 10:52:10 AM | 87.6 |
| 10:52:25 AM | 87.8 |
| 10:52:40 AM | 87.5 |
| 10:52:55 AM | 87.6 |
| 10:53:10 AM | 87.4 |
| 10:53:25 AM | 87.6 |
| 10:53:40 AM | 87.6 |
| 10:53:55 AM | 87.6 |
| 10:54:10 AM | 87.6 |
| 10:54:25 AM | 87.5 |
| 10:54:40 AM | 87.4 |
| 10:54:55 AM | 87.3 |
| 10:55:10 AM | 87.2 |

FIG. 12B

| TIME | TECH SAMPLE F (°F) |
|---|---|
| 10:55:25 AM | 87.1 |
| 10:55:40 AM | 87.1 |
| 10:55:55 AM | 87 |
| 10:56:10 AM | 86.8 |
| 10:56:25 AM | 87 |
| 10:56:40 AM | 87.3 |
| 10:56:55 AM | 87.3 |
| 10:57:10 AM | 86.4 |
| 10:57:25 AM | 86.9 |
| 10:57:40 AM | 87.3 |
| 10:57:55 AM | 87.2 |
| 10:58:10 AM | 86.7 |
| 10:58:25 AM | 86.3 |
| 10:58:40 AM | 85.9 |
| 10:58:55 AM | 85.4 |
| 10:59:10 AM | 85.3 |
| 10:59:25 AM | 85.3 |
| 10:59:40 AM | 85.1 |
| 10:59:55 AM | 85 |
| 11:00:10 AM | 84.9 |
| 11:00:25 AM | 84.8 |
| 11:00:40 AM | 84.8 |
| 11:00:55 AM | 85.4 |
| 11:01:10 AM | 85.5 |
| 11:01:25 AM | 85.5 |
| 11:01:40 AM | 85.4 |
| 11:01:55 AM | 85.2 |
| 11:02:10 AM | 85.2 |
| 11:02:25 AM | 85.1 |
| 11:02:40 AM | 84.9 |
| 11:02:55 AM | 83.8 |
| 11:03:10 AM | 82.8 |
| 11:03:25 AM | 82.6 |

FIG. 12C

| TIME | TECH SAMPLE F (°F) |
|---|---|
| 11:03:40 AM | 82.1 |
| 11:03:55 AM | 81.7 |
| 11:04:10 AM | 81.4 |
| 11:04:25 AM | 81.2 |
| 11:04:40 AM | 80.9 |
| 11:04:55 AM | 81.1 |
| 11:05:10 AM | 82.2 |
| 11:05:25 AM | 82.7 |
| 11:05:40 AM | 82.9 |
| 11:05:55 AM | 82.9 |
| 11:06:10 AM | 82.6 |
| 11:06:25 AM | 82.5 |
| 11:06:40 AM | 82.7 |
| 11:06:55 AM | 82.8 |
| 11:07:10 AM | 82.9 |
| 11:07:25 AM | 83 |
| 11:07:40 AM | 83.1 |
| 11:07:55 AM | 83.1 |
| 11:08:10 AM | 83.1 |
| 11:08:25 AM | 83.2 |
| 11:08:40 AM | 83.1 |
| 11:08:55 AM | 83.1 |
| 11:09:10 AM | 83.3 |
| 11:09:25 AM | 83.1 |
| 11:09:40 AM | 82.5 |
| 11:09:55 AM | 82 |
| 11:10:10 AM | 81.8 |
| 11:10:25 AM | 81.6 |
| 11:10:40 AM | 81.6 |
| 11:10:55 AM | 81.4 |
| 11:11:10 AM | 81.1 |
| 11:11:25 AM | 81.3 |
| 11:11:40 AM | 81.5 |

FIG. 12D

| TIME | TECH SAMPLE F (°F) |
|---|---|
| 11:11:55 AM | 81.5 |
| 11:12:10 AM | 81.3 |
| 11:12:25 AM | 81.1 |
| 11:12:40 AM | 80.6 |
| 11:12:55 AM | 80.3 |
| 11:13:10 AM | 80.1 |
| 11:13:25 AM | 80 |
| 11:13:40 AM | 79.9 |
| 11:13:55 AM | 79.6 |
| 11:14:10 AM | 79.4 |
| 11:14:25 AM | 79.2 |
| 11:14:40 AM | 79 |
| 11:14:55 AM | 78.8 |
| 11:15:10 AM | 78.7 |
| 11:15:25 AM | 79.1 |
| 11:15:40 AM | 79.5 |
| 11:15:55 AM | 79.5 |
| 11:16:10 AM | 79.2 |
| 11:16:25 AM | 79.2 |
| 11:16:40 AM | 79 |
| 11:16:55 AM | 79.8 |
| 11:17:10 AM | 79.8 |
| 11:17:25 AM | 79.7 |
| 11:17:40 AM | 79.4 |
| 11:17:55 AM | 79.2 |
| 11:18:10 AM | 78 |
| 11:18:25 AM | 77.2 |
| 11:18:40 AM | 76.8 |
| 11:18:55 AM | 76.5 |
| 11:19:10 AM | 76.3 |
| 11:19:25 AM | 75.9 |
| 11:19:40 AM | 75.7 |
| 11:19:55 AM | 75.7 |
| 11:20:10 AM | 75.6 |

FIG. 12E

| TIME | TECH SAMPLE F (°F) |
|---|---|
| 11:20:25 AM | 75.6 |
| 11:20:40 AM | 75.3 |
| 11:20:55 AM | 75 |
| 11:21:10 AM | 74.8 |
| 11:21:25 AM | 74.7 |
| 11:21:40 AM | 74.8 |
| 11:21:55 AM | 75.1 |
| 11:22:10 AM | 75.5 |
| 11:22:25 AM | 76.1 |
| 11:22:40 AM | 76.9 |
| 11:22:55 AM | 77.4 |
| 11:23:10 AM | 77.7 |
| 11:23:25 AM | 77.7 |
| 11:23:40 AM | 77.9 |
| 11:23:55 AM | 77.2 |
| 11:24:10 AM | 76.1 |
| 11:24:25 AM | 75.8 |
| 11:24:40 AM | 76.2 |
| 11:24:55 AM | 76.4 |
| 11:25:10 AM | 76.7 |
| 11:25:25 AM | 77 |
| 11:25:40 AM | 77.2 |
| 11:25:55 AM | 77.4 |
| 11:26:10 AM | 77.6 |
| 11:26:25 AM | 77.8 |
| 11:26:40 AM | 77.9 |
| 11:26:55 AM | 78 |
| 11:27:10 AM | 78.1 |
| 11:27:25 AM | 78.3 |
| 11:27:40 AM | 78.4 |
| 11:27:55 AM | 78.5 |
| 11:28:10 AM | 78.5 |
| 11:28:25 AM | 78.6 |

FIG. 12F

| TIME | TECH SAMPLE F (°F) |
|---|---|
| 11:28:40 AM | 78.6 |
| 11:28:55 AM | 77.1 |
| 11:29:10 AM | 76 |
| 11:29:25 AM | 75.3 |
| 11:29:40 AM | 75 |
| 11:29:55 AM | 74.6 |
| 11:30:10 AM | 74.6 |
| 11:30:25 AM | 74.4 |
| 11:30:40 AM | 74.6 |
| 11:30:55 AM | 74.4 |
| 11:31:10 AM | 74.1 |
| 11:31:25 AM | 73.9 |
| 11:31:40 AM | 73.7 |
| 11:31:55 AM | 73.7 |
| 11:32:10 AM | 73.7 |
| 11:32:25 AM | 73.7 |
| 11:32:40 AM | 73.6 |
| 11:32:55 AM | 73.5 |
| 11:33:10 AM | 73.4 |
| 11:33:25 AM | 73.2 |
| 11:33:40 AM | 73.1 |
| 11:33:55 AM | 73 |
| 11:34:10 AM | 73 |
| 11:34:25 AM | 73.1 |
| 11:34:40 AM | 73.1 |
| 11:34:55 AM | 73.1 |
| 11:35:10 AM | 73 |
| 11:35:25 AM | 72.8 |
| 11:35:40 AM | 72.8 |
| 11:35:55 AM | 72.7 |
| 11:36:10 AM | 73.3 |
| 11:36:25 AM | 73.2 |
| 11:36:40 AM | 72.5 |

FIG. 12G

| TIME | TECH SAMPLE F (°F) |
|---|---|
| 11:36:55 AM | 72.1 |
| 11:37:10 AM | 71.8 |
| 11:37:25 AM | 71.5 |
| 11:37:40 AM | 71.3 |
| 11:37:55 AM | 71.9 |
| 11:38:10 AM | 72.7 |

FIG. 12H

| TIME | TECH SAMPLE G (°F) |
|---|---|
| 2:13:02 PM | 78.2 |
| 2:13:17 PM | 78.6 |
| 2:13:32 PM | 78.3 |
| 2:13:47 PM | 78.1 |
| 2:14:02 PM | 77 |
| 2:14:17 PM | 76.6 |
| 2:14:32 PM | 77.7 |
| 2:14:47 PM | 77.9 |
| 2:15:02 PM | 78.3 |
| 2:15:17 PM | 78.5 |
| 2:15:32 PM | 78.6 |
| 2:15:47 PM | 78.6 |
| 2:16:02 PM | 78.7 |
| 2:16:17 PM | 78.9 |
| 2:16:32 PM | 79 |
| 2:16:47 PM | 79.1 |
| 2:17:02 PM | 79.1 |
| 2:17:17 PM | 78.9 |
| 2:17:32 PM | 78.7 |
| 2:17:47 PM | 78 |
| 2:18:02 PM | 78.7 |
| 2:18:17 PM | 79 |
| 2:18:32 PM | 79.1 |
| 2:18:47 PM | 79.1 |
| 2:19:02 PM | 79.4 |
| 2:19:17 PM | 79.6 |
| 2:19:32 PM | 79.9 |
| 2:19:47 PM | 80.1 |
| 2:20:02 PM | 80.2 |
| 2:20:17 PM | 80.3 |
| 2:20:32 PM | 80.4 |
| 2:20:47 PM | 80.6 |

FIG. 13A

| TIME | TECH SAMPLE G (°F) |
|---|---|
| 2:21:02 PM | 80.4 |
| 2:21:17 PM | 80.6 |
| 2:21:32 PM | 80.7 |
| 2:21:47 PM | 80.6 |
| 2:22:02 PM | 80.7 |
| 2:22:17 PM | 80.8 |
| 2:22:32 PM | 80.7 |
| 2:22:47 PM | 80.7 |
| 2:23:02 PM | 80.8 |
| 2:23:17 PM | 80.8 |
| 2:23:32 PM | 80.9 |
| 2:23:47 PM | 80.8 |
| 2:24:02 PM | 80.8 |
| 2:24:17 PM | 80.7 |
| 2:24:32 PM | 80.6 |
| 2:24:47 PM | 79.8 |
| 2:25:02 PM | 80.3 |
| 2:25:17 PM | 80.8 |
| 2:25:32 PM | 81.1 |
| 2:25:47 PM | 81.3 |
| 2:26:02 PM | 81.3 |
| 2:26:17 PM | 81.3 |
| 2:26:32 PM | 81.5 |
| 2:26:47 PM | 81.7 |
| 2:27:02 PM | 81.7 |
| 2:27:17 PM | 81.7 |
| 2:27:32 PM | 81.8 |
| 2:27:47 PM | 81.8 |
| 2:28:02 PM | 81.6 |
| 2:28:17 PM | 81.4 |
| 2:28:32 PM | 81.3 |
| 2:28:47 PM | 81.2 |
| 2:29:02 PM | 81 |
| 2:29:17 PM | 81.2 |

FIG. 13B

| TIME | TECH SAMPLE G (°F) |
|---|---|
| 2:29:32 PM | 81.3 |
| 2:29:47 PM | 81.5 |
| 2:30:02 PM | 81.6 |
| 2:30:17 PM | 81.7 |
| 2:30:32 PM | 81 |
| 2:30:47 PM | 81 |
| 2:31:02 PM | 81.1 |
| 2:31:17 PM | 81.3 |
| 2:31:32 PM | 81.2 |
| 2:31:47 PM | 81.2 |
| 2:32:02 PM | 81.1 |
| 2:32:17 PM | 81.1 |
| 2:32:32 PM | 81 |
| 2:32:47 PM | 80.9 |
| 2:33:02 PM | 80.7 |
| 2:33:17 PM | 80.6 |
| 2:33:32 PM | 80.3 |
| 2:33:47 PM | 80.2 |
| 2:34:02 PM | 80 |
| 2:34:17 PM | 79.9 |
| 2:34:32 PM | 79.8 |
| 2:34:47 PM | 79.8 |
| 2:35:02 PM | 79.8 |
| 2:35:17 PM | 79.8 |
| 2:35:32 PM | 79.6 |
| 2:35:47 PM | 79.6 |
| 2:36:02 PM | 79.6 |
| 2:36:17 PM | 79.5 |
| 2:36:32 PM | 79.4 |
| 2:36:47 PM | 79.1 |
| 2:37:02 PM | 78.7 |
| 2:37:17 PM | 79.3 |
| 2:37:32 PM | 79.6 |

FIG. 13C

| TIME | TECH SAMPLE G (°F) |
|---|---|
| 2:37:47 PM | 79.7 |
| 2:38:02 PM | 79.8 |
| 2:38:17 PM | 80 |
| 2:38:32 PM | 80.1 |
| 2:38:47 PM | 80.1 |
| 2:39:02 PM | 80.2 |
| 2:39:17 PM | 80 |
| 2:39:32 PM | 79.6 |
| 2:39:47 PM | 79.5 |
| 2:40:02 PM | 79.4 |
| 2:40:17 PM | 79.5 |
| 2:40:32 PM | 79.5 |
| 2:40:47 PM | 79.4 |
| 2:41:02 PM | 78.1 |
| 2:41:17 PM | 77.1 |
| 2:41:32 PM | 77.4 |
| 2:41:47 PM | 77.5 |
| 2:42:02 PM | 76.7 |
| 2:42:17 PM | 76.3 |
| 2:42:32 PM | 76.3 |
| 2:42:47 PM | 77 |
| 2:43:02 PM | 77.3 |
| 2:43:17 PM | 77.5 |
| 2:43:32 PM | 77.6 |
| 2:43:47 PM | 77.8 |
| 2:44:02 PM | 77.9 |
| 2:44:17 PM | 77.7 |
| 2:44:32 PM | 77.5 |
| 2:44:47 PM | 77.3 |
| 2:45:02 PM | 77.4 |
| 2:45:17 PM | 77.4 |
| 2:45:32 PM | 77.2 |
| 2:45:47 PM | 77.2 |

FIG. 13D

| TIME | TECH SAMPLE G (°F) |
|---|---|
| 2:46:02 PM | 77.4 |
| 2:46:17 PM | 77.5 |
| 2:46:32 PM | 77.6 |
| 2:46:47 PM | 77.7 |
| 2:47:02 PM | 77.7 |
| 2:47:17 PM | 77.7 |
| 2:47:32 PM | 77.8 |
| 2:47:47 PM | 77.7 |
| 2:48:02 PM | 77.6 |
| 2:48:17 PM | 77.4 |
| 2:48:32 PM | 77.3 |
| 2:48:47 PM | 77.2 |
| 2:49:02 PM | 76.9 |
| 2:49:17 PM | 76.6 |
| 2:49:32 PM | 76.5 |
| 2:49:47 PM | 76.4 |
| 2:50:02 PM | 76.4 |
| 2:50:17 PM | 76.3 |
| 2:50:32 PM | 76.2 |
| 2:50:47 PM | 76.3 |
| 2:51:02 PM | 76.3 |
| 2:51:17 PM | 76.2 |
| 2:51:32 PM | 76.1 |
| 2:51:47 PM | 76 |
| 2:52:02 PM | 75.9 |
| 2:52:17 PM | 76 |
| 2:52:32 PM | 76 |
| 2:52:47 PM | 76 |
| 2:53:02 PM | 75.9 |
| 2:53:17 PM | 75.7 |
| 2:53:32 PM | 75.2 |
| 2:53:47 PM | 75.3 |
| 2:54:02 PM | 75.1 |

FIG. 13E

| TIME | TECH SAMPLE G (°F) |
|---|---|
| 2:54:17 PM | 74.6 |
| 2:54:32 PM | 73.6 |
| 2:54:47 PM | 73.8 |
| 2:55:02 PM | 73.9 |
| 2:55:17 PM | 73.4 |
| 2:55:32 PM | 72.9 |
| 2:55:47 PM | 72.5 |
| 2:56:02 PM | 72.7 |
| 2:56:17 PM | 72.7 |
| 2:56:32 PM | 72.7 |
| 2:56:47 PM | 71 |
| 2:57:02 PM | 71.6 |
| 2:57:17 PM | 71.1 |
| 2:57:32 PM | 71.1 |
| 2:57:47 PM | 71.1 |
| 2:58:02 PM | 71.1 |
| 2:58:17 PM | 70.7 |
| 2:58:32 PM | 71.1 |
| 2:58:47 PM | 71.7 |
| 2:59:02 PM | 72.1 |
| 2:59:17 PM | 72.5 |
| 2:59:32 PM | 72.7 |
| 2:59:47 PM | 71.9 |
| 3:00:02 PM | 71.9 |
| 3:00:17 PM | 72 |
| 3:00:32 PM | 71.3 |
| 3:00:47 PM | 71.2 |
| 3:01:02 PM | 70.6 |
| 3:01:17 PM | 70.3 |
| 3:01:32 PM | 70.2 |
| 3:01:47 PM | 69.9 |
| 3:02:02 PM | 69.5 |
| 3:02:17 PM | 69.4 |

FIG. 13F

| TIME | TECH SAMPLE G (°F) |
|---|---|
| 3:02:32 PM | 69.3 |
| 3:02:47 PM | 69.1 |
| 3:03:02 PM | 68.9 |
| 3:03:17 PM | 68.9 |
| 3:03:32 PM | 68.7 |
| 3:03:47 PM | 68.8 |
| 3:04:02 PM | 68.9 |
| 3:04:17 PM | 68.9 |
| 3:04:32 PM | 68.8 |
| 3:04:47 PM | 68.9 |
| 3:05:02 PM | 68.9 |
| 3:05:17 PM | 68.8 |
| 3:05:32 PM | 68.6 |
| 3:05:47 PM | 68.3 |
| 3:06:02 PM | 68.5 |
| 3:06:17 PM | 68.4 |
| 3:06:32 PM | 68.5 |
| 3:06:47 PM | 68.6 |
| 3:07:02 PM | 68.6 |
| 3:07:17 PM | 68.6 |
| 3:07:32 PM | 68.7 |
| 3:07:47 PM | 68.3 |
| 3:08:02 PM | 68.1 |
| 3:08:17 PM | 68 |
| 3:08:32 PM | 67.8 |
| 3:08:47 PM | 67.8 |
| 3:09:02 PM | 68 |
| 3:09:17 PM | 67.9 |
| 3:09:32 PM | 68 |
| 3:09:47 PM | 68.1 |
| 3:10:02 PM | 68.5 |
| 3:10:17 PM | 68.7 |
| 3:10:32 PM | 68.8 |

FIG. 13G

| TIME | TECH SAMPLE G (°F) |
|---|---|
| 3:10:47 PM | 68.9 |
| 3:11:02 PM | 69 |
| 3:11:17 PM | 68.3 |
| 3:11:32 PM | 68.5 |
| 3:11:47 PM | 67.7 |
| 3:12:02 PM | 67.7 |
| 3:12:17 PM | 67.4 |
| 3:12:32 PM | 68.2 |
| 3:12:47 PM | 68.3 |

FIG. 13H

| TIME | TECH SAMPLE H (°F) |
|---|---|
| 11:09:04 AM | 81.1 |
| 11:09:19 AM | 81.1 |
| 11:09:34 AM | 80.9 |
| 11:09:49 AM | 80.9 |
| 11:10:04 AM | 80.2 |
| 11:10:19 AM | 79.8 |
| 11:10:34 AM | 79.4 |
| 11:10:49 AM | 79.3 |
| 11:11:04 AM | 79.2 |
| 11:11:19 AM | 79.1 |
| 11:11:34 AM | 79.4 |
| 11:11:49 AM | 78.9 |
| 11:12:04 AM | 78.9 |
| 11:12:19 AM | 78.8 |
| 11:12:34 AM | 78.7 |
| 11:12:49 AM | 78.6 |
| 11:13:04 AM | 78.6 |
| 11:13:19 AM | 78.6 |
| 11:13:34 AM | 79.2 |
| 11:13:49 AM | 79.8 |
| 11:14:04 AM | 80 |
| 11:14:19 AM | 80.2 |
| 11:14:34 AM | 79.5 |
| 11:14:49 AM | 79.3 |
| 11:15:04 AM | 79 |
| 11:15:19 AM | 78.6 |
| 11:15:34 AM | 79.4 |
| 11:15:49 AM | 80.4 |
| 11:16:04 AM | 80.7 |
| 11:16:19 AM | 80.4 |
| 11:16:34 AM | 80.4 |
| 11:16:49 AM | 80 |

FIG. 14A

| TIME | TECH SAMPLE H (°F) |
|---|---|
| 11:17:04 AM | 79.4 |
| 11:17:19 AM | 79.1 |
| 11:17:34 AM | 78.8 |
| 11:17:49 AM | 78.8 |
| 11:18:04 AM | 78.9 |
| 11:18:19 AM | 79.6 |
| 11:18:34 AM | 79.9 |
| 11:18:49 AM | 79.8 |
| 11:19:04 AM | 79.1 |
| 11:19:19 AM | 79.3 |
| 11:19:34 AM | 78.6 |
| 11:19:49 AM | 77.8 |
| 11:20:04 AM | 78.4 |
| 11:20:19 AM | 79.1 |
| 11:20:34 AM | 80 |
| 11:20:49 AM | 80.6 |
| 11:21:04 AM | 80.9 |
| 11:21:19 AM | 80.7 |
| 11:21:34 AM | 79.6 |
| 11:21:49 AM | 80.6 |
| 11:22:04 AM | 80.7 |
| 11:22:19 AM | 79.5 |
| 11:22:34 AM | 80.3 |
| 11:22:49 AM | 80 |
| 11:23:04 AM | 80 |
| 11:23:19 AM | 79.7 |
| 11:23:34 AM | 79.6 |
| 11:23:49 AM | 79.5 |
| 11:24:04 AM | 79.4 |
| 11:24:19 AM | 79.2 |
| 11:24:34 AM | 79.1 |
| 11:24:49 AM | 78.6 |
| 11:25:04 AM | 78.3 |

FIG. 14B

| TIME | TECH SAMPLE H (°F) |
|---|---|
| 11:25:19 AM | 78.7 |
| 11:25:34 AM | 78.7 |
| 11:25:49 AM | 78.5 |
| 11:26:04 AM | 77.4 |
| 11:26:19 AM | 76.7 |
| 11:26:34 AM | 76.5 |
| 11:26:49 AM | 77.2 |
| 11:27:04 AM | 77.8 |
| 11:27:19 AM | 78 |
| 11:27:34 AM | 77.8 |
| 11:27:49 AM | 77.6 |
| 11:28:04 AM | 77.7 |
| 11:28:19 AM | 78.2 |
| 11:28:34 AM | 78.3 |
| 11:28:49 AM | 78.4 |
| 11:29:04 AM | 78.6 |
| 11:29:19 AM | 78.8 |
| 11:29:34 AM | 78.5 |
| 11:29:49 AM | 78.1 |
| 11:30:04 AM | 77.9 |
| 11:30:19 AM | 77.6 |
| 11:30:34 AM | 77.8 |
| 11:30:49 AM | 77.6 |
| 11:31:04 AM | 77.5 |
| 11:31:19 AM | 77.2 |
| 11:31:34 AM | 77.1 |
| 11:31:49 AM | 77.2 |
| 11:32:04 AM | 77.2 |
| 11:32:19 AM | 77 |
| 11:32:34 AM | 76.4 |
| 11:32:49 AM | 76.6 |
| 11:33:04 AM | 76.6 |
| 11:33:19 AM | 76.6 |

FIG. 14C

| TIME | TECH SAMPLE H (°F) |
|---|---|
| 11:33:34 AM | 76.3 |
| 11:33:49 AM | 75.6 |
| 11:34:04 AM | 75.2 |
| 11:34:19 AM | 74.9 |
| 11:34:34 AM | 74.8 |
| 11:34:49 AM | 74.8 |
| 11:35:04 AM | 74.7 |
| 11:35:19 AM | 74.3 |
| 11:35:34 AM | 74 |
| 11:35:49 AM | 74 |
| 11:36:04 AM | 73.8 |
| 11:36:19 AM | 74.2 |
| 11:36:34 AM | 74.8 |
| 11:36:49 AM | 74.9 |
| 11:37:04 AM | 74.5 |
| 11:37:19 AM | 74 |
| 11:37:34 AM | 73.9 |
| 11:37:49 AM | 73.9 |
| 11:38:04 AM | 73.6 |
| 11:38:19 AM | 73.3 |
| 11:38:34 AM | 73.6 |
| 11:38:49 AM | 73 |
| 11:39:04 AM | 72.3 |
| 11:39:19 AM | 72.4 |
| 11:39:34 AM | 72.8 |
| 11:39:49 AM | 72.4 |
| 11:40:04 AM | 71.9 |
| 11:40:19 AM | 71.9 |
| 11:40:34 AM | 72 |
| 11:40:49 AM | 71.8 |
| 11:41:04 AM | 71.6 |
| 11:41:19 AM | 71.6 |
| 11:41:34 AM | 71.1 |

FIG. 14D

| TIME | TECH SAMPLE H (°F) |
|---|---|
| 11:41:49 AM | 70.2 |
| 11:42:04 AM | 70.2 |
| 11:42:19 AM | 70.1 |
| 11:42:34 AM | 70.1 |
| 11:42:49 AM | 71.4 |
| 11:43:04 AM | 71.5 |
| 11:43:19 AM | 71.3 |
| 11:43:34 AM | 71.3 |
| 11:43:49 AM | 71.3 |
| 11:44:04 AM | 71.3 |
| 11:44:19 AM | 71.3 |
| 11:44:34 AM | 70.7 |
| 11:44:49 AM | 69.6 |
| 11:45:04 AM | 70.1 |
| 11:45:19 AM | 71 |
| 11:45:34 AM | 71.3 |
| 11:45:49 AM | 71.9 |
| 11:46:04 AM | 71.1 |
| 11:46:19 AM | 70.4 |
| 11:46:34 AM | 70.1 |
| 11:46:49 AM | 69.9 |
| 11:47:04 AM | 70.1 |
| 11:47:19 AM | 70.4 |
| 11:47:34 AM | 70.6 |
| 11:47:49 AM | 72 |
| 11:48:04 AM | 72.4 |
| 11:48:19 AM | 72.5 |
| 11:48:34 AM | 72.5 |
| 11:48:49 AM | 72.5 |
| 11:49:04 AM | 72.5 |
| 11:49:19 AM | 72.5 |
| 11:49:34 AM | 72.4 |
| 11:49:49 AM | 72.5 |

FIG. 14E

| TIME | TECH SAMPLE H (°F) |
|---|---|
| 11:50:04 AM | 72.5 |
| 11:50:19 AM | 72.4 |
| 11:50:34 AM | 72.3 |
| 11:50:49 AM | 72.1 |
| 11:51:04 AM | 72.2 |
| 11:51:19 AM | 72.2 |
| 11:51:34 AM | 72.4 |
| 11:51:49 AM | 72.5 |
| 11:52:04 AM | 71.9 |
| 11:52:19 AM | 71.9 |
| 11:52:34 AM | 72.5 |
| 11:52:49 AM | 72.4 |
| 11:53:04 AM | 72.3 |
| 11:53:19 AM | 72.3 |
| 11:53:34 AM | 72.6 |
| 11:53:49 AM | 72.9 |
| 11:54:04 AM | 72.6 |
| 11:54:19 AM | 71.5 |
| 11:54:34 AM | 71.6 |
| 11:54:49 AM | 70.3 |
| 11:55:04 AM | 70.9 |
| 11:55:19 AM | 70.1 |
| 11:55:34 AM | 70.5 |
| 11:55:49 AM | 70.1 |
| 11:56:04 AM | 69.9 |
| 11:56:19 AM | 70.1 |
| 11:56:34 AM | 69.8 |
| 11:56:49 AM | 69.8 |
| 11:57:04 AM | 69.8 |
| 11:57:19 AM | 70.4 |
| 11:57:34 AM | 70.9 |
| 11:57:49 AM | 71.3 |
| 11:58:04 AM | 71.4 |
| 11:58:19 AM | 71.2 |

FIG. 14F

| TIME | TECH SAMPLE H (°F) |
|---|---|
| 11:58:34 AM | 71.3 |
| 11:58:49 AM | 71.6 |
| 11:59:04 AM | 72.1 |
| 11:59:19 AM | 72.4 |
| 11:59:34 AM | 72.5 |
| 11:59:49 AM | 72.5 |
| 12:00:04 PM | 71.9 |
| 12:00:19 PM | 71.4 |
| 12:00:34 PM | 71.2 |
| 12:00:49 PM | 71.6 |
| 12:01:04 PM | 71.5 |
| 12:01:19 PM | 70.5 |
| 12:01:34 PM | 70.1 |
| 12:01:49 PM | 69.9 |
| 12:02:04 PM | 69.7 |
| 12:02:19 PM | 69.7 |
| 12:02:34 PM | 69.6 |
| 12:02:49 PM | 69.7 |
| 12:03:04 PM | 70 |
| 12:03:19 PM | 70.4 |
| 12:03:34 PM | 70.3 |
| 12:03:49 PM | 70.3 |
| 12:04:04 PM | 70 |
| 12:04:19 PM | 69.8 |
| 12:04:34 PM | 69.8 |
| 12:04:49 PM | 69.8 |
| 12:05:04 PM | 69.7 |
| 12:05:19 PM | 69.5 |
| 12:05:34 PM | 69.1 |
| 12:05:49 PM | 68.8 |
| 12:06:04 PM | 69.3 |
| 12:06:19 PM | 69.4 |
| 12:06:34 PM | 69.4 |
| 12:06:49 PM | 69.7 |

FIG. 14G

| TIME | TECH SAMPLE H (°F) |
|---|---|
| 12:07:04 PM | 68.6 |
| 12:07:19 PM | 68.8 |
| 12:07:34 PM | 68.3 |
| 12:07:49 PM | 67.8 |
| 12:08:04 PM | 68.4 |
| 12:08:19 PM | 69 |

FIG. 14H

| TIME | TEST SAMPLE I (°F) |
|---|---|
| 11:05:19 AM | 82.8 |
| 11:05:34 AM | 82.9 |
| 11:05:49 AM | 83 |
| 11:06:04 AM | 83.1 |
| 11:06:19 AM | 83 |
| 11:06:34 AM | 83.4 |
| 11:06:49 AM | 82.1 |
| 11:07:04 AM | 81.3 |
| 11:07:19 AM | 81.5 |
| 11:07:34 AM | 81.2 |
| 11:07:49 AM | 81 |
| 11:08:04 AM | 81.1 |
| 11:08:19 AM | 81.2 |
| 11:08:34 AM | 81.1 |
| 11:08:49 AM | 80.7 |
| 11:09:04 AM | 80.7 |
| 11:09:19 AM | 80.8 |
| 11:09:34 AM | 80.7 |
| 11:09:49 AM | 80.8 |
| 11:10:04 AM | 81 |
| 11:10:19 AM | 81.9 |
| 11:10:34 AM | 81.8 |
| 11:10:49 AM | 82.2 |
| 11:11:04 AM | 82.5 |
| 11:11:19 AM | 82.6 |
| 11:11:34 AM | 82.7 |
| 11:11:49 AM | 82.8 |
| 11:12:04 AM | 83 |
| 11:12:19 AM | 82.9 |
| 11:12:34 AM | 82.9 |
| 11:12:49 AM | 82.9 |
| 11:13:04 AM | 83.5 |

FIG. 15A

| TIME | TEST SAMPLE I (°F) |
|---|---|
| 11:13:19 AM | 83.8 |
| 11:13:34 AM | 83.9 |
| 11:13:49 AM | 84 |
| 11:14:04 AM | 84.1 |
| 11:14:19 AM | 84.3 |
| 11:14:34 AM | 84.4 |
| 11:14:49 AM | 84.4 |
| 11:15:04 AM | 84.5 |
| 11:15:19 AM | 84.6 |
| 11:15:34 AM | 84.7 |
| 11:15:49 AM | 84.1 |
| 11:16:04 AM | 83.2 |
| 11:16:19 AM | 83 |
| 11:16:34 AM | 82.7 |
| 11:16:49 AM | 83.1 |
| 11:17:04 AM | 83.3 |
| 11:17:19 AM | 83.6 |
| 11:17:34 AM | 83.6 |
| 11:17:49 AM | 83.7 |
| 11:18:04 AM | 83.6 |
| 11:18:19 AM | 83.6 |
| 11:18:34 AM | 83.6 |
| 11:18:49 AM | 83.4 |
| 11:19:04 AM | 83.4 |
| 11:19:19 AM | 82.5 |
| 11:19:34 AM | 82.1 |
| 11:19:49 AM | 82.1 |
| 11:20:04 AM | 82.6 |
| 11:20:19 AM | 82.9 |
| 11:20:34 AM | 83 |
| 11:20:49 AM | 82.7 |
| 11:21:04 AM | 82.8 |

FIG. 15B

| TIME | TEST SAMPLE I (°F) |
|---|---|
| 11:21:19 AM | 83.2 |
| 11:21:34 AM | 83.2 |
| 11:21:49 AM | 83.2 |
| 11:22:04 AM | 83.4 |
| 11:22:19 AM | 83.5 |
| 11:22:34 AM | 83.6 |
| 11:22:49 AM | 83.6 |
| 11:23:04 AM | 83.6 |
| 11:23:19 AM | 83.6 |
| 11:23:34 AM | 83.7 |
| 11:23:49 AM | 83.6 |
| 11:24:04 AM | 83.7 |
| 11:24:19 AM | 83.7 |
| 11:24:34 AM | 83.8 |
| 11:24:49 AM | 83.9 |
| 11:25:04 AM | 84 |
| 11:25:19 AM | 84 |
| 11:25:34 AM | 84.1 |
| 11:25:49 AM | 84 |
| 11:26:04 AM | 84.1 |
| 11:26:19 AM | 83.9 |
| 11:26:34 AM | 83.7 |
| 11:26:49 AM | 83.7 |
| 11:27:04 AM | 83.6 |
| 11:27:19 AM | 83.6 |
| 11:27:34 AM | 83.7 |
| 11:27:49 AM | 83.7 |
| 11:28:04 AM | 83.6 |
| 11:28:19 AM | 83.6 |
| 11:28:34 AM | 83.6 |
| 11:28:49 AM | 83.7 |
| 11:29:04 AM | 83.7 |

FIG. 15C

| TIME | TEST SAMPLE I (°F) |
|---|---|
| 11:29:19 AM | 83.7 |
| 11:29:34 AM | 83.7 |
| 11:29:49 AM | 83.5 |
| 11:30:04 AM | 83.6 |
| 11:30:19 AM | 83.5 |
| 11:30:34 AM | 83.5 |
| 11:30:49 AM | 83.6 |
| 11:31:04 AM | 83.5 |
| 11:31:19 AM | 83.4 |
| 11:31:34 AM | 83.4 |
| 11:31:49 AM | 83.2 |
| 11:32:04 AM | 83.5 |
| 11:32:19 AM | 83.5 |
| 11:32:34 AM | 83.6 |
| 11:32:49 AM | 83.7 |
| 11:33:04 AM | 83.7 |
| 11:33:19 AM | 83.7 |
| 11:33:34 AM | 83.7 |
| 11:33:49 AM | 83.5 |
| 11:34:04 AM | 83.3 |
| 11:34:19 AM | 83.4 |
| 11:34:34 AM | 82.9 |
| 11:34:49 AM | 81.8 |
| 11:35:04 AM | 82.1 |
| 11:35:19 AM | 81.8 |
| 11:35:34 AM | 81.5 |
| 11:35:49 AM | 80 |
| 11:36:04 AM | 79.9 |
| 11:36:19 AM | 80.8 |
| 11:36:34 AM | 81.2 |
| 11:36:49 AM | 81.4 |
| 11:37:04 AM | 81.3 |

FIG. 15D

| TIME | TEST SAMPLE I (°F) |
|---|---|
| 11:37:19 AM | 81.4 |
| 11:37:34 AM | 81.5 |
| 11:37:49 AM | 81.6 |
| 11:38:04 AM | 81.7 |
| 11:38:19 AM | 81.7 |
| 11:38:34 AM | 81.7 |
| 11:38:49 AM | 81.7 |
| 11:39:04 AM | 81.5 |
| 11:39:19 AM | 81.1 |
| 11:39:34 AM | 80.8 |
| 11:39:49 AM | 80.4 |
| 11:40:04 AM | 80 |
| 11:40:19 AM | 80.3 |
| 11:40:34 AM | 80.7 |
| 11:40:49 AM | 80.7 |
| 11:41:04 AM | 80.9 |
| 11:41:19 AM | 81 |
| 11:41:34 AM | 81.1 |
| 11:41:49 AM | 80.9 |
| 11:42:04 AM | 80.6 |
| 11:42:19 AM | 80.7 |
| 11:42:34 AM | 80.8 |
| 11:42:49 AM | 80.7 |
| 11:43:04 AM | 80.6 |
| 11:43:19 AM | 80.7 |
| 11:43:34 AM | 80.8 |
| 11:43:49 AM | 80.8 |
| 11:44:04 AM | 80.8 |
| 11:44:19 AM | 80.8 |
| 11:44:34 AM | 80.6 |
| 11:44:49 AM | 80.3 |
| 11:45:04 AM | 80.2 |

FIG. 15E

| TIME | TEST SAMPLE I (°F) |
|---|---|
| 11:45:19 AM | 80 |
| 11:45:34 AM | 79.6 |
| 11:45:49 AM | 79.1 |
| 11:46:04 AM | 78.9 |
| 11:46:19 AM | 79.3 |
| 11:46:34 AM | 79.3 |
| 11:46:49 AM | 79.2 |
| 11:47:04 AM | 79.3 |
| 11:47:19 AM | 79.2 |
| 11:47:34 AM | 79 |
| 11:47:49 AM | 79 |
| 11:48:04 AM | 78.6 |
| 11:48:19 AM | 78.5 |
| 11:48:34 AM | 78.4 |
| 11:48:49 AM | 78.1 |
| 11:49:04 AM | 77.5 |
| 11:49:19 AM | 77.5 |
| 11:49:34 AM | 76.7 |
| 11:49:49 AM | 77.5 |
| 11:50:04 AM | 77.9 |
| 11:50:19 AM | 77.9 |
| 11:50:34 AM | 78 |
| 11:50:49 AM | 78.2 |
| 11:51:04 AM | 78.1 |
| 11:51:19 AM | 78 |
| 11:51:34 AM | 78 |
| 11:51:49 AM | 77.9 |
| 11:52:04 AM | 77.7 |
| 11:52:19 AM | 77.6 |
| 11:52:34 AM | 77.5 |
| 11:52:49 AM | 77.5 |
| 11:53:04 AM | 77.3 |

FIG. 15F

| TIME | TEST SAMPLE I (°F) |
|---|---|
| 11:53:19 AM | 77.1 |
| 11:53:34 AM | 76 |
| 11:53:49 AM | 76.9 |
| 11:54:04 AM | 76.8 |
| 11:54:19 AM | 77 |
| 11:54:34 AM | 77.1 |
| 11:54:49 AM | 77 |
| 11:55:04 AM | 76.8 |
| 11:55:19 AM | 76.6 |
| 11:55:34 AM | 76.9 |
| 11:55:49 AM | 77 |
| 11:56:04 AM | 76.9 |
| 11:56:19 AM | 76.6 |
| 11:56:34 AM | 76.5 |
| 11:56:49 AM | 76.4 |
| 11:57:04 AM | 76.3 |
| 11:57:19 AM | 76.2 |
| 11:57:34 AM | 76.2 |
| 11:57:49 AM | 76.2 |
| 11:58:04 AM | 76.2 |
| 11:58:19 AM | 76.3 |
| 11:58:34 AM | 76.1 |
| 11:58:49 AM | 76.1 |
| 11:59:04 AM | 75.7 |
| 11:59:19 AM | 75.2 |
| 11:59:34 AM | 75.5 |
| 11:59:49 AM | 75.3 |
| 12:00:04 PM | 74.1 |
| 12:00:19 PM | 74.4 |
| 12:00:34 PM | 73.9 |
| 12:00:49 PM | 73.9 |
| 12:01:04 PM | 74.4 |

FIG. 15G

| TIME | TEST SAMPLE I (°F) |
|---|---|
| 12:01:19 PM | 74.4 |
| 12:01:34 PM | 74.3 |
| 12:01:49 PM | 74.1 |
| 12:02:04 PM | 73.6 |
| 12:02:19 PM | 73.2 |
| 12:02:34 PM | 72.7 |
| 12:02:49 PM | 72.5 |
| 12:03:04 PM | 72.6 |
| 12:03:19 PM | 72.5 |
| 12:03:34 PM | 72.1 |
| 12:03:49 PM | 71.9 |
| 12:04:04 PM | 71.9 |
| 12:04:19 PM | 71.8 |
| 12:04:34 PM | 71.9 |
| 12:04:49 PM | 72.2 |

FIG. 15H

ENERGY HARVESTING, HEAT MANAGING, MULTI-EFFECT THERAPEUTIC GARMENT

CROSS-REFERENCE TO RELATED APPLICATIONS

This application claims priority to and the benefit of provisional patent application No. 62/200,124 titled "Energy Harvesting, Heat Managing, Multi-effect Therapeutic Garment", filed in the United States Patent and Trademark Office on Aug. 3, 2015. The specification of the above referenced patent application is incorporated herein by reference in its entirety.

BACKGROUND

Raynaud's syndrome, aggravation of arthritis in hands and feet, cold hands and feet, and discoloration of fingers and toes in cold weather are caused by reduced blood flow to hands, fingers, and toes in cold weather. This condition where blood supply to the fingers or the toes is significantly reduced due to narrowing of blood vessels, due to which, for example, skin turns pale or white and becomes cold and numb due to cold weather is called vasospasm. Persons suffering from vasospasm may also experience thickening of blood vessels in their fingers and toes over time, thereby further limiting the blood flow. Vasospasm over a prolonged period of time can lead to tissue death. Raynaud's syndrome is managed primarily by treating the underlying cause and avoiding triggers, for example, cold conditions, keeping a warm core body temperature by dressing for cold weather in layers and wearing gloves or heavy socks, etc. Most garments with active heat management features use electric heating, single use or re-useable heating cartridges or inserts, microwaveable gels, or other organic materials in a lining of the garment, etc., to provide heat to persons suffering from Raynaud's syndrome and/or arthritis. In these conventional heat management methods, additional heat is introduced into the garment by using additional, relatively cumbersome devices, which restrict movement and provide discomfort to a wearer.

Hence, there is a long felt need for an energy harvesting, heat managing, multi-effect therapeutic garment that harvests energy from both a wearer's interaction with the therapeutic garment and ambient environment, and converts the harvested energy into heat energy that can be stored and distributed within the therapeutic garment without any additional device for introducing and maintaining heat within the therapeutic garment.

SUMMARY OF THE INVENTION

This summary is provided to introduce a selection of concepts in a simplified form that are further disclosed in the detailed description of the invention. This summary is not intended to determine the scope of the claimed subject matter.

The energy harvesting, heat managing, multi-effect therapeutic garment, herein referred to as a "therapeutic garment", and method of construction thereof, address the above mentioned need for harvesting energy from both a wearer's interaction with the therapeutic garment and ambient environment, and converting the harvested energy into heat energy that can be stored and distributed within the therapeutic garment without any additional device, for example, a heat cartridge, a heatable insert, microwaveable gels, battery, charger, etc., for introducing and maintaining heat within the therapeutic garment. The therapeutic garment disclosed herein is made from a combination of a predetermined number of yarns, for example, at least three yarns defining an inner surface and at least one yarn defining an outer surface of the therapeutic garment. The yarns are knitted in a single piece free of seams as a complete garment or as a whole garment, thereby providing an improved fit with improved construction integrity.

The therapeutic garment disclosed herein comprises an enclosure configured to conform to a wearer's body part, for example, the wearer's hand, feet, torso, or any other part of the wearer's body. The enclosure comprises an inner surface and an outer surface, the inner surface being proximal to the wearer's body part and the outer surface being distal to the wearer's body part when the wearer is wearing the enclosure. The therapeutic garment comprises a combination of a predetermined number of yarns knitted to create the enclosure. The yarns comprise a first yarn for absorbing, storing, and releasing heat energy through a phase change, a second yarn for converting the heat energy into far infrared radiation energy and radiating the far infrared radiation energy to other of the yarns and to the wearer's body part, a third yarn for adsorbing moisture from the wearer's body part and/or ambient environment and generating heat energy through an exothermic reaction between the moisture and desiccant type crystals contained in the third yarn, a fourth yarn for converting ultraviolet radiation energy from sunlight into far infrared radiation energy and radiating the far infrared radiation energy to other of the yarns and to the wearer's body part, a fifth yarn for providing heat insulation and for repelling water, and a sixth yarn for conducting heat and maintaining a uniform temperature within the yarns. A bundle of inner yarns selected from the predetermined number of yarns disclosed above is knitted with a bundle of outer yarns selected from the predetermined number of yarns disclosed above to define the inner surface and the outer surface of the enclosure respectively. The bundle of inner yarns is knitted with the bundle of outer yarns to create a uniform surface area distribution of the inner yarns and the outer yarns on the inner surface and the outer surface of the enclosure respectively. Knitting of the bundle of inner yarns and the bundle of outer yarns produces interwoven inner yarns and interwoven outer yarns, respectively. The interwoven inner yarns are exposed on the inner surface of the enclosure and the interwoven outer yarns are exposed on the outer surface of the enclosure. The interwoven inner yarns and the interwoven outer yarns contact each other and cover the wearer's body part when the therapeutic garment is worn by the wearer.

Disclosed herein is also a method for constructing the therapeutic garment with self-contained heat management capabilities. In the method disclosed herein, multiple yarns as disclosed above are provided and an enclosure configured to conform to the wearer's body part is created as follows. A predetermined number of inner yarns and a predetermined number of outer yarns are selected from the yarns disclosed above. The selected inner yarns are wound onto a first set of spools and the selected outer yarns are wound onto a second set of spools. A bundle of the selected inner yarns and a bundle of the selected outer yarns are created by pulling the selected inner yarns from the first set of spools and by pulling the selected outer yarns from the second set of spools, respectively. The created bundle of the selected inner yarns and the created bundle of the selected outer yarns are fed into a knitting machine via a feeder. The fed bundle of the selected inner yarns is knit with the fed bundle of the selected outer yarns in the knitting machine to create the enclosure conforming to the wearer's body part. The knitted bundle of the selected inner yarns defines the inner surface of the enclosure and the knitted bundle of the selected outer yarns defines the outer surface of the enclosure. The knitted bundle of the selected inner yarns is exposed on the inner surface of the enclosure and the knitted bundle of the selected outer yarns is exposed on the outer surface of the enclosure. The positions of the inner yarns and the outer yarns are consistently maintained relative to each other to create a uniform surface area distribution of the inner yarns and the outer yarns on the inner surface and the outer surface of the enclosure, respectively.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific structures and methods disclosed herein. The description of a structure or a method step referenced by a numeral in a drawing is applicable to the description of that structure or method step shown by that same numeral in any subsequent drawing herein.

FIG. 4A exemplarily illustrates feeding of the twisted bundle of inner yarns and the twisted bundle of outer yarns into a plaiting feeder.

FIG. 4B exemplarily illustrates an enlarged view of a guide element of the plaiting feeder shown in FIG. 4A.

FIGS. 8A-8B exemplarily illustrate tables containing construction data of yarns in multiple test samples of the energy harvesting, heat managing, multi-effect therapeutic garment.

FIGS. 9A-9H exemplarily illustrate a table containing skin temperature measurements of a wearer wearing test sample A and test sample B of the energy harvesting, heat managing, multi-effect therapeutic garment.

FIGS. 10A-10H exemplarily illustrate a table containing skin temperature measurements of a wearer wearing test sample D and test sample C of the energy harvesting, heat managing, multi-effect therapeutic garment.

FIGS. 11A-11H exemplarily illustrate a table containing skin temperature measurements of a wearer wearing test sample E of the energy harvesting, heat managing, multi-effect therapeutic garment.

FIGS. 12A-12H exemplarily illustrate a table containing skin temperature measurements of a wearer wearing test sample F of the energy harvesting, heat managing, multi-effect therapeutic garment.

FIGS. 13A-13H exemplarily illustrate a table containing skin temperature measurements of a wearer wearing test sample G of the energy harvesting, heat managing, multi-effect therapeutic garment.

FIGS. 14A-14H exemplarily illustrate a table containing skin temperature measurements of a wearer wearing test sample H of the energy harvesting, heat managing, multi-effect therapeutic garment.

FIGS. 15A-15H exemplarily illustrate a table containing skin temperature measurements of a wearer wearing test sample I of the energy harvesting, heat managing, multi-effect therapeutic garment.

DETAILED DESCRIPTION OF THE INVENTION

Figure 1:
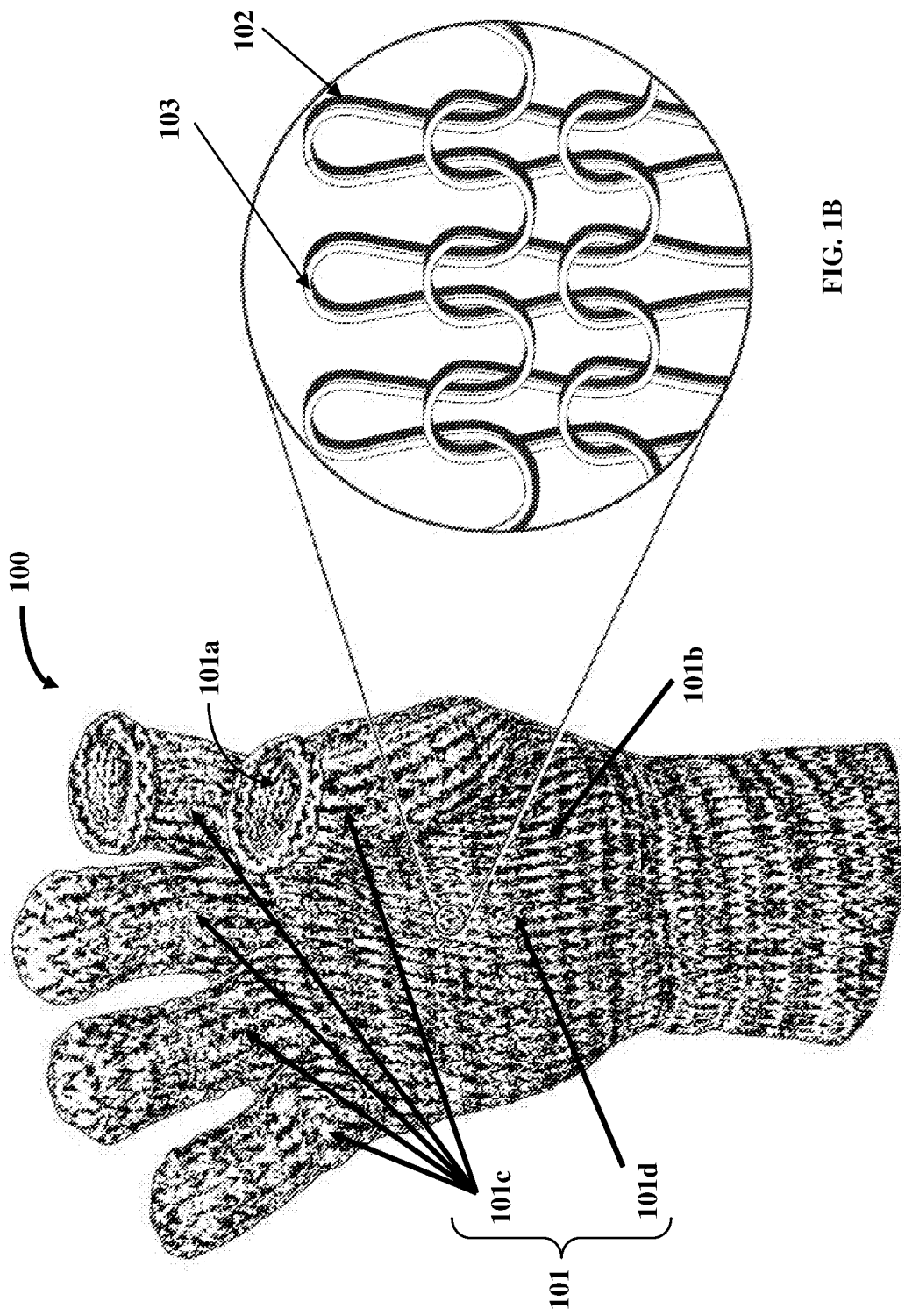
FIG. 1A exemplarily illustrates an energy harvesting, heat managing, multi-effect therapeutic garment configured as a therapeutic glove.
FIG. 1B exemplarily illustrates an enlarged view of a portion of the energy harvesting, heat managing, multi-effect therapeutic garment shown in FIG. 1A, showing inner yarns knitted with outer yarns.

FIG. 1A exemplarily illustrates an energy harvesting, heat managing, multi-effect therapeutic garment 100, herein referred to as a "therapeutic garment", configured as a therapeutic glove. For purposes of illustration, the detailed description refers to the therapeutic garment 100 configured as a therapeutic glove; however the scope of the therapeutic garment 100 disclosed herein is not limited to be configured as a therapeutic glove, but may be extended to be configured as a therapeutic sock to be worn on a wearer's foot, a therapeutic undergarment, a therapeutic T-shirt, or any other type of garment that can be worn on a wearer's body part, for example, hands, feet, torso, or any other part of the wearer's body to provide heat to the wearer. The therapeutic garment 100 comprises an enclosure 101 configured to conform to a wearer's body part, for example, the wearer's hand. The enclosure 101 is configured, for example, as a glove. The enclosure 101 comprises an inner surface 101a and an outer surface 101b defining a finger section 101c and a palm section 101d of the therapeutic garment 100. The inner surface 101a is proximal to the wearer's body part and the outer surface 101b is distal to the wearer's body part when the wearer is wearing the enclosure 101. The therapeutic garment 100 disclosed herein addresses needs of persons who suffer, for example, from Raynaud's syndrome and/or rheumatoid arthritis in their hands and feet, or those who suffer from cold hands and feet in cold weather. The therapeutic garment 100 disclosed herein further comprises a combination of a predetermined number of yarns knitted to create the enclosure 101. The therapeutic garment 100 disclosed herein is made from a combination of a predetermined number of yarns for defining the inner surface 101a and the outer surface 101b of the therapeutic garment 100. The predetermined number of yarns of the therapeutic garment 100 is knitted by a knitted construction that maintains the positions of the predetermined number of yarns relative to each other.

FIG. 1B exemplarily illustrates an enlarged view of a portion of the energy harvesting, heat managing, multi-effect therapeutic garment 100 shown in FIG. 1A, showing inner yarns 102 knitted with outer yarns 103. A bundle of inner yarns 102 selected from the predetermined number of yarns is knitted with a bundle of outer yarns 103 selected from the predetermined number of yarns to define the inner surface 101a and the outer surface 101b of the enclosure 101 exemplarily illustrated in FIG. 1A, respectively, and to create a uniform surface area distribution of the inner yarns 102 and the outer yarns 103 on the inner surface 101a and the outer surface 101b of the enclosure 101 respectively. The knitted bundle of inner yarns 102 is exposed on the inner surface 101a of the enclosure 101 and the knitted bundle of outer yarns 103 is exposed on the outer surface 101b of the enclosure 101. The knitted bundle of inner yarns 102 and the knitted bundle of outer yarns 103 contact each other and cover the wearer's body part, for example, the skin on the wearer's hand when the therapeutic garment 100 is worn by the wearer.

The bundle of inner yarns 102 and the bundle of outer yarns 103 are selected from the following yarns 101a, 101b, 101c, 101d, 102a, 102b, and 102c as exemplarily illustrated in FIG. 3A and FIGS. 3C-3E: a first yarn 102a for absorbing, storing, and releasing heat energy through a phase change; a second yarn 102b for converting the heat energy into far infrared radiation energy and for radiating the far infrared radiation energy to other yarns and to a wearer's body part; a third yarn 102c for adsorbing moisture from the wearer's body part and/or the ambient environment and for generating heat energy through an exothermic reaction between the moisture and desiccant type crystals contained in the third yarn 102c; a fourth yarn 103a for converting ultraviolet radiation energy from sunlight into far infrared radiation energy and for radiating the far infrared radiation energy to other yarns and to the wearer's body part; a fifth yarn 103b that is heat resistant and provides heat insulation and is hydrophobic, that is, water repellant; and a sixth yarn 102d for conducting heat and maintaining a uniform temperature, that is, an even distribution of temperature within the yarns.

Figure 3A:
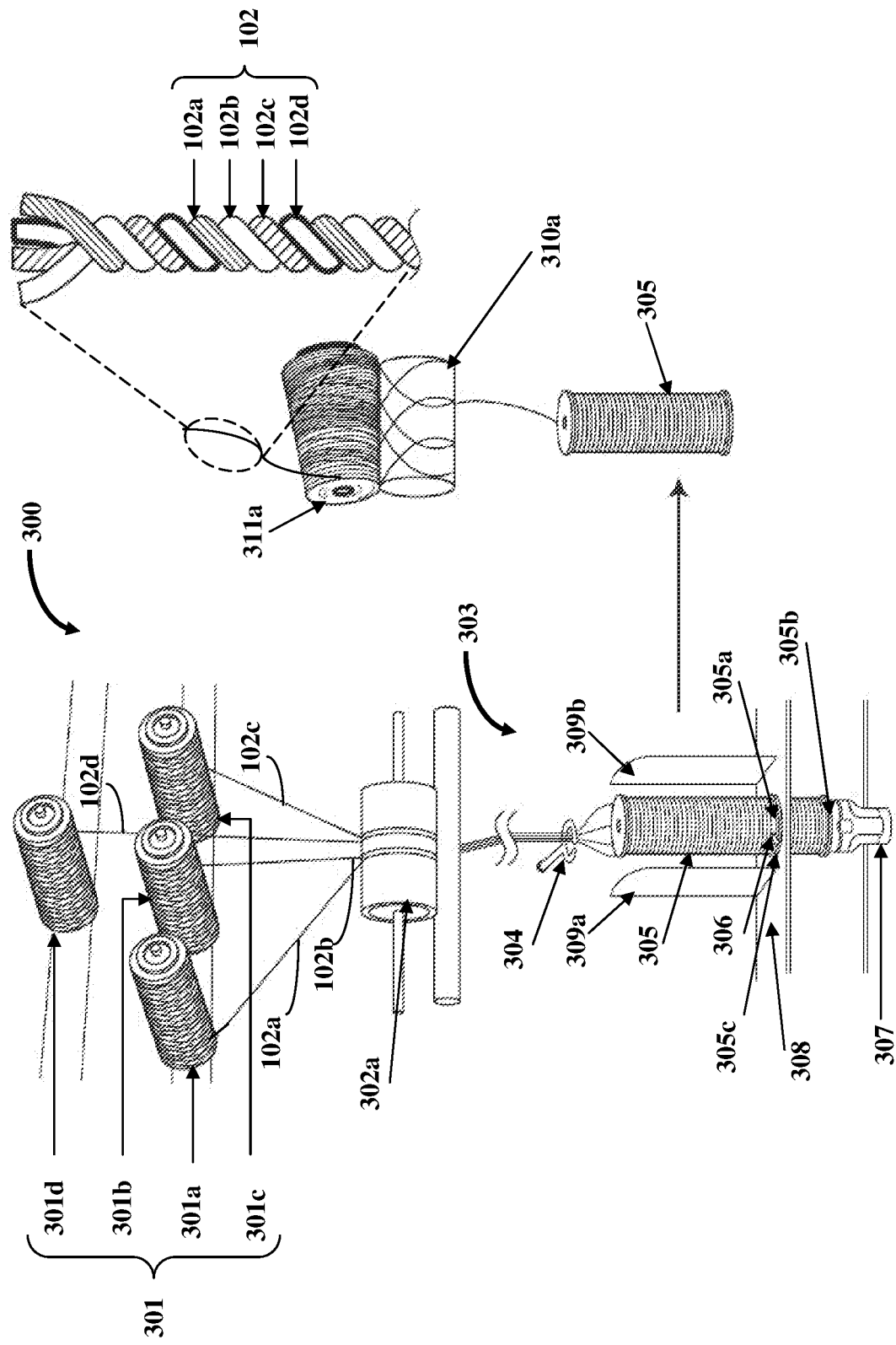
FIG. 3A exemplarily illustrates a yarn bundle creation machine for creating a bundle of inner yarns from a first set of spools.

At least three of the yarns in the bundle of inner yarns 102 are selected from the first yarn 102a, the second yarn 102b, the third yarn 102c, and the sixth yarn 102d exemplarily illustrated in FIG. 3A, to define the inner surface 101a of the enclosure 101. In an embodiment, the bundle of inner yarns 102 that defines the inner surface 101a of the enclosure 101 comprise the first yarn 102a, the second yarn 102b, and the third yarn 102c. In another embodiment, the bundle of inner yarns 102 that defines the inner surface 101a of the enclosure 101 comprises the first yarn 102a, the second yarn 102b, the third yarn 102c, and the sixth yarn 102d. The functionality, structure, and/or material of the first yarn 102a, the second yarn 102b, the third yarn 102c, and the sixth yarn 102d that define the inner surface 101a of the therapeutic garment 100 are disclosed below.

The first yarn 102a is made of a phase change material for absorbing, storing, and releasing heat energy similar to a heat battery through a physical chemical process called phase change. As used herein, "phase change material (PCM)" refers to a substance that undergoes a process of phase change, for example, from a solid phase to a liquid phase and vice versa. The phase change material absorbs, stores, and releases heat energy as the phase change material oscillates between a solid phase and a liquid phase. The phase change functionality in the first yarn 102a comes from micron size droplets of paraffin or similar phase change materials that change between a liquid phase and a solid phase, which are encapsulated in the first yarn 102a. When heated, the phase change material droplets contained in the first yarn 102a change to a liquid phase, and when cooled, the phase change material droplets contained in the first yarn 102a change to a solid phase. Heat energy is released as the phase change material changes to a solid phase and heat energy is absorbed as the phase change material returns to a liquid phase. Phase change in the phase change material is dependent on the temperature range that is just above and just below human skin temperature. The first yarn 102a with its phase change material stores heat generated by the wearer. In an embodiment, the phase change material applied to the first yarn 102a is in the 100 micron to 100,000 micron range. In an embodiment, the phase change material is sprayed onto the first yarn 102a. Furthermore, the phase change material in the first yarn 102a provides a heat buffering functionality to the first yarn 102a. The first yarn 102a therefore functions as a heat buffer and minimizes temperature swings in the therapeutic garment 100, thereby providing a uniform temperature within the therapeutic garment 100. An example of the first yarn 102a is the Outlast® phase change yarn of Outlast Technologies, LLC, Golden, Colo.

The second yarn 102b conductively harvests the wearer's body heat and the heat energy from the first yarn 102a and converts the harvested heat energy into far infrared radiation energy that radiates far infrared heat. The wavelength of the far infrared radiation is in a range of, for example, about 1 micrometer (μm) to about 10 μm. The second yarn 102b comprises multiple bioceramic particles. The bioceramic particles are, for example, boron-silicate minerals or tourmaline in a nanoparticle form embedded in the second yarn 102b. The bioceramic particles are minerals with photo thermal properties. The bioceramic particles emit and/or reflect far infrared thermal radiation when heated. The far infrared thermal radiation promotes molecular vibration leading to increased cellular metabolism and cell membrane permeability, thereby triggering biochemical changes that stimulate the exchange of metabolites and adenosine triphosphate (ATP) synthesis, up-regulation of chemical mediators that play a role in edema formation, pH regulation, free radicals metabolism, and microcirculation. Therefore, the molecular vibration due to the far infrared radiation results in physiological effects essential to the healing process, for example, pain relief, decrease of inflammatory processes, re-absorption of edema, and nerve or lymphatic vessel regeneration. Far infrared rays can penetrate the wearer's skin and underlying tissues, and generate heat by causing subcutaneous proteins, collagens, fats, and water molecules to vibrate, elevating tissue temperatures and causing blood vessels to dilate. The improvement in blood circulation delivers more oxygen to the tissues, thereby providing a range of therapeutic effects. An example of the second yarn 102b is the NILIT® Innergy yarn of NILIT Limited Corporation, Maurizio Levi Road, P.O. Box 276, Ramat Gabriel, Migdal Haemek, 2310201, Israel.

The third yarn 102c generates heat energy by adsorbing moisture from perspiration of the wearer and/or from humidity in the ambient environment. The third yarn 102c comprises desiccant type crystals, for example, silica crystals for adsorbing moisture and releasing heat. The adsorbed moisture and the desiccant type crystals contained in the third yarn 102c undergo an exothermic reaction to generate heat energy. An example of the third yarn 102c is the eks® yarn of Toyobo Co., Ltd., Osaka, Japan.

The sixth yarn 102d functions to maintain a uniform temperature within the combination of the predetermined number of yarns, for example, using carbon nanotube technology. The sixth yarn 102d is a carbon nanofiber. Carbon nanofibers are seamless, cylindrical, hollow, and lightweight fibers, comprising a single sheet of pure graphite. The type of bond holding graphite atoms together has substantial strength, and a hexagonal pattern of the graphite atoms gives rise to a phenomenon known as electron delocalization. The graphite atoms vibrate to move heat through the nanotube structure of the carbon nanofiber, thereby providing high thermal and electrical conductivity within the therapeutic garment 100. The thermal conductivity of the sixth yarn 102d functions to equalize temperature distribution within the therapeutic garment 100. The sixth yarn 102d equalizes temperature between the palm section 101d and the finger section 101c of the enclosure 101 exemplarily illustrated in FIG. 1A, by transferring heat from the palm section 101d to the finger section 101c of the enclosure 101. As the inner palm is the warmest part of the wearer's hand, the sixth yarn 102d exposed on the inner surface 101a of the enclosure 101 configured, for example, as a glove, equalizes the temperature between the inner palm and colder fingers by conducting heat from the palm section 101d of the enclosure 101 to the finger section 101c of the enclosure 101. An example of the sixth yarn 102d is the Miralon™ yarn by Nanocomp Technologies, Inc., Merrimack, N.H.

Figure 3B:
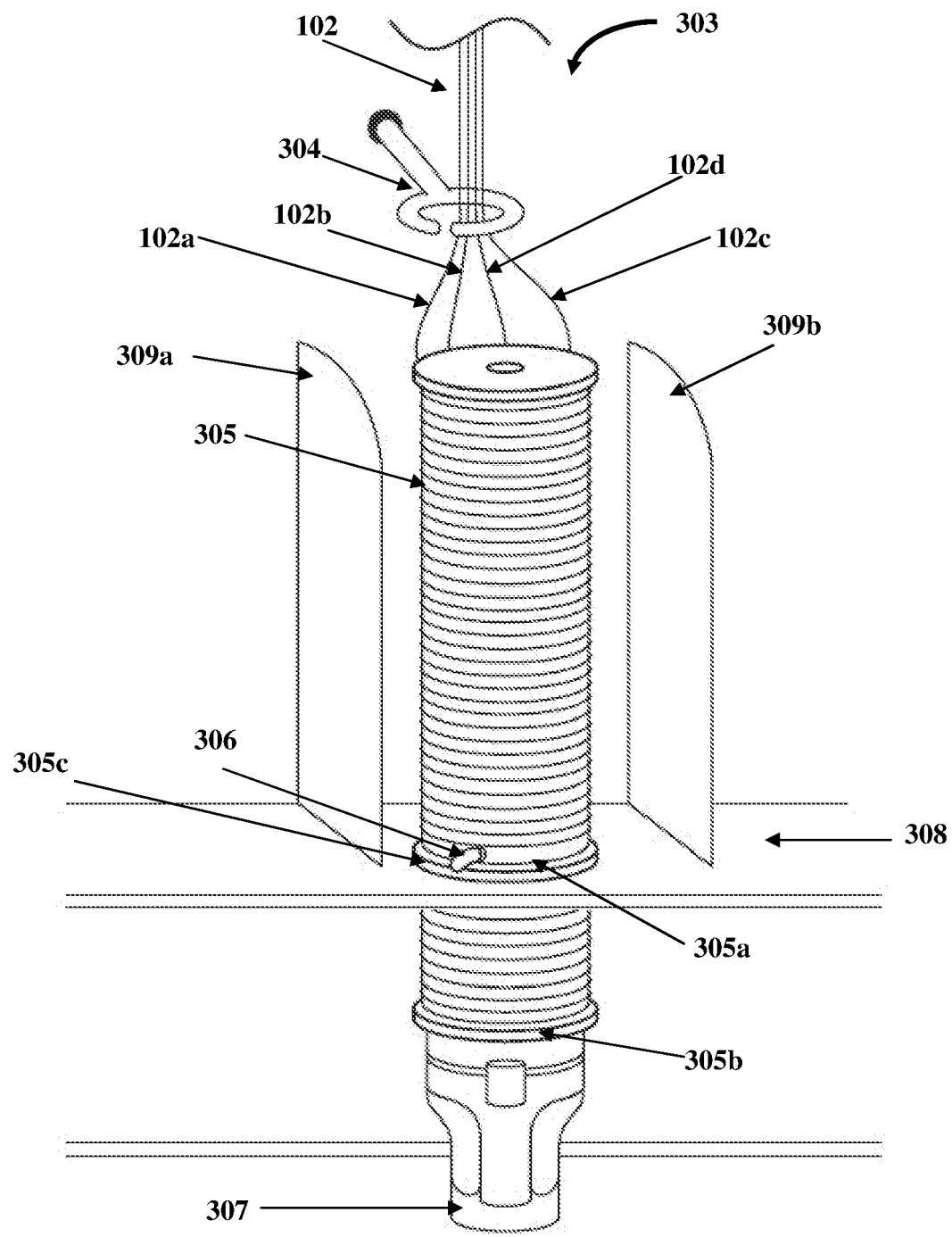
FIG. 3B exemplarily illustrates an enlarged view of a twisting machine incorporated within the yarn bundle creation machine for creating a twisted bundle of inner yarns.
Figure 3C:
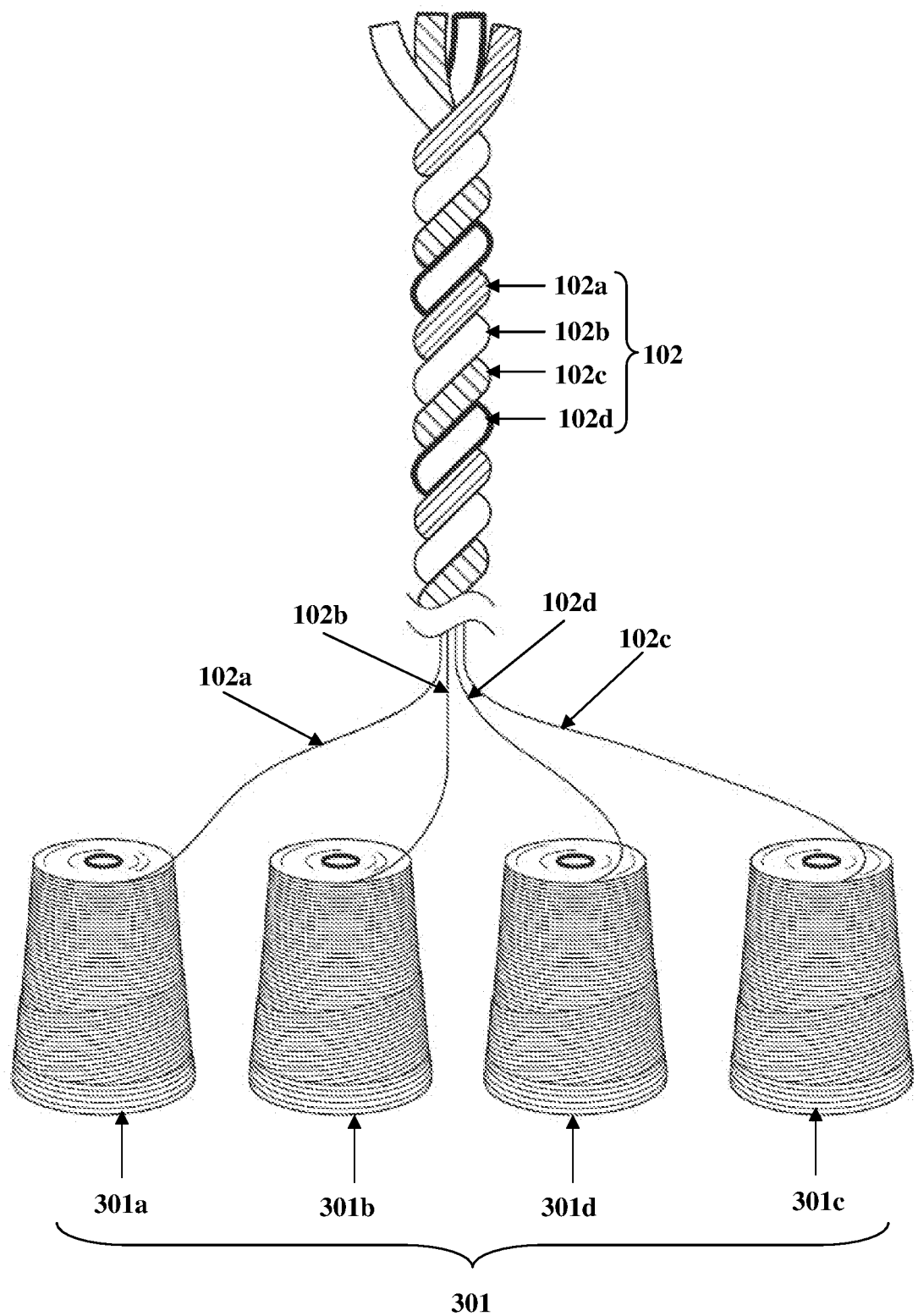
FIG. 3C exemplarily illustrates creation of the twisted bundle of inner yarns from the first set of spools.
Figure 3D:
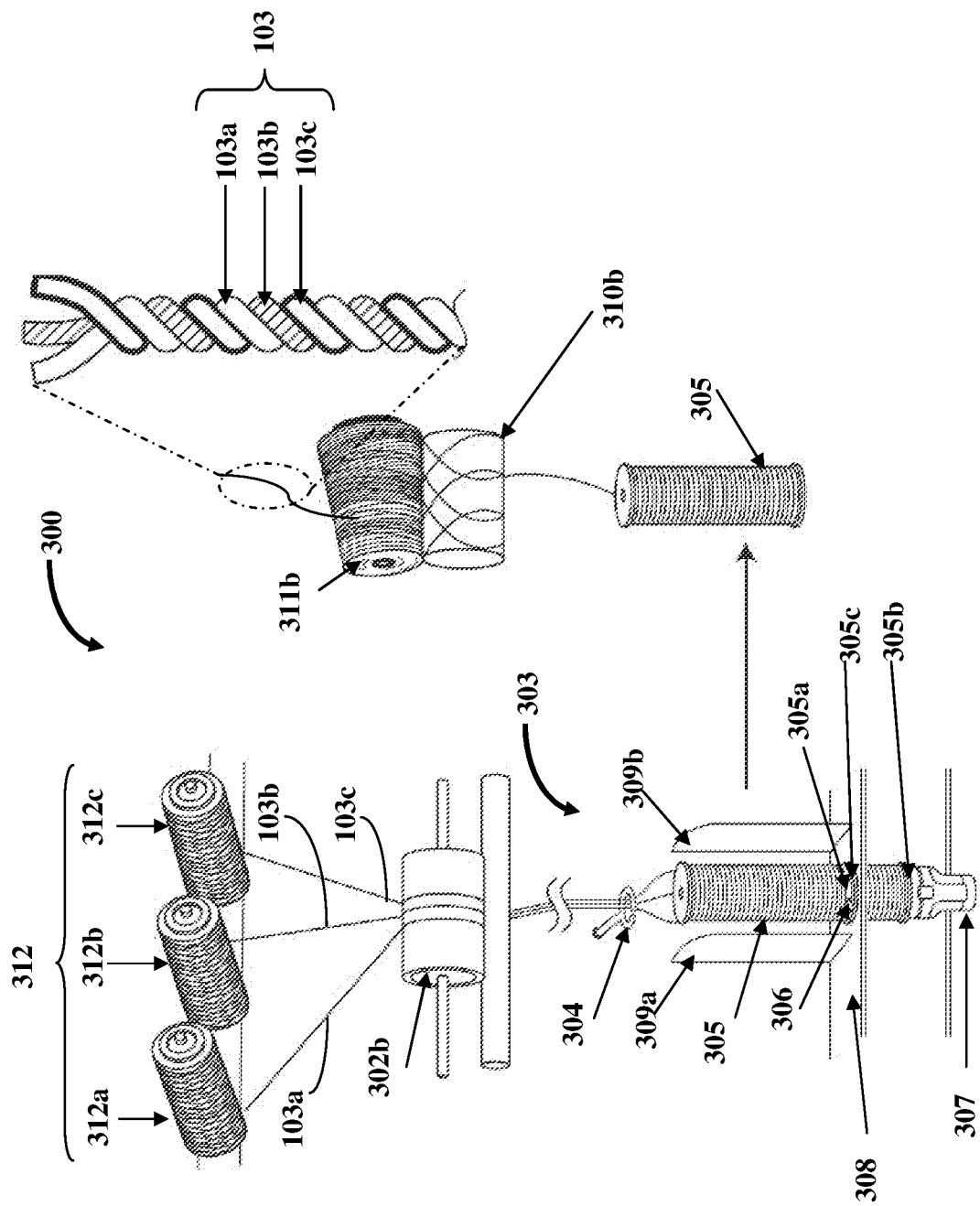
FIG. 3D exemplarily illustrates a yarn bundle creation machine for creating a bundle of outer yarns from a second set of spools.

At least one of the yarns in the bundle of outer yarns 103 is selected from the third yarn 102c, the fourth yarn 103a, and the fifth yarn 103b exemplarily illustrated in FIG. 3D, to define the outer surface 101b of the enclosure 101. In an embodiment, the bundle of outer yarns 103 that defines the outer surface 101b of the enclosure 101 comprises the third yarn 102c and the fifth yarn 103b. In another embodiment, the bundle of outer yarns 103 that defines the outer surface 101b of the enclosure 101 comprises the fourth yarn 103a and the fifth yarn 103b. In another embodiment, the bundle of outer yarns 103 that defines the outer surface 101b of the enclosure 101 comprises the third yarn 102c, the fourth yarn 103a, and the fifth yarn 103b. In another embodiment, the bundle of outer yarns 103 that defines the outer surface 101b of the enclosure 101 comprises multiple threads of the fifth yarn 103b. In an embodiment, the bundle of outer yarns 103 comprises a supplementary yarn 103c, for example, a 40 denier spandex yarn bundled with at least one of the third yarn 102c, the fourth yarn 103a, and the fifth yarn 103b to define the outer surface 101b of the enclosure 101. The third yarn 102c, the fourth yarn 103a, the fifth yarn 103b, and the supplementary yarn 103c that define the outer surface 101b of the enclosure 101 are disclosed below:

The third yarn 102c in the bundle of outer yarns 103 is disclosed above in the description of the bundle of inner yarns 102. The fourth yarn 103a in the bundle of outer yarns 103 is exposed on the outer surface 101b of the enclosure 101 for exposure to ultraviolet radiation. The wavelength of the ultraviolet radiation is in a range of, for example, about 10 nanometers (nm) to about 380 nm. An example of the fourth yarn 103a is CERAM® A of Japan Exlan Co., Ltd., Osaka, Japan.

The fifth yarn 103b is an olefin or polypropylene fiber, with low specific gravity, low thermal conductivity, and high insulting properties. The fifth yarn 103b is heat insulating and hydrophobic and therefore repels water to reduce an intrusion of unwanted outside cold weather into the therapeutic garment 100. The fifth yarn 103b is bacteria and micro-organism resistant, water resistant, fade resistant, and resistant to most acids. The heat insulating function of the fifth yarn 103b keeps the cold out and locks the warmth of the inner surface 101a within the therapeutic garment 100. An example of the fifth yarn 103b is Prolen® by Chemosvit Fibrochem, Štúrova, Slovakia.

The supplementary yarn 103c enhances heat conductivity between the wearer's body part and the inner surface 101a of the enclosure 101. An example of the supplementary yarn 103c is, for example, a 40 denier spandex. The supplementary yarn 103c also allows the therapeutic garment 100 to have a snug fit on the wearer's body part. The supplementary yarn 103c has significant elasticity made of a polyester-polyurethane copolymer, for example, Lycra® of the INVISTA company, Wichita, Kans.

The therapeutic garment 100 maintains the wearer's skin temperature at a comfortable level by combining conductive heat transfer and heat radiation within the therapeutic garment 100 and between the therapeutic garment 100 and the wearer's body part. This multi-effect heat transfer and the therapeutic performance of the therapeutic garment 100 are achieved by interactions between the yarns disclosed above and between the yarns and the wearer of the therapeutic garment 100, as a result of the combination of at least three of several different yarn configurations in the entire therapeutic garment 100 or in specific areas of the therapeutic garment 100.

The interactions between the yarns further improve when the therapeutic garment 100 has an inner surface 101a and an outer surface 101b as exemplarily illustrated in FIG. 1A. The first yarn 102a absorbs far infrared radiation energy in the range of, for example, about 1 μm to about 10 μm from the second yarn 102b and the fourth yarn 103a and conductively receives heat energy from the third yarn 102c by physical contact with the third yarn 102c. The first yarn 102a with the heat buffering effect of the phase change material, in conjunction with the sixth yarn 102d having high heat conductivity, affects a uniform temperature within the combination of the predetermined number of yarns. The second yarn 102b, the third yarn 102c, and the fourth yarn 103a interact with each other and with the wearer's body part and/or the ambient environment to harvest heat energy. The second yarn 102b and the fourth yarn 103a provide a deep, gentle heating to the wearer's body part by radiating the far infrared radiation energy into the other yarns, and also back to skin tissues of the wearer's body part. The hydrophobic property of the fifth yarn 103b removes moisture when the fifth yarn 103b is in contact with the third yarn 102c, thereby allowing the exothermic process between the moisture and desiccant type crystals contained in the third yarn 102c to progress without reaching equilibrium or saturation.

The inner surface 101a and the outer surface 101b of the enclosure 101 of the therapeutic garment 100 are knitted using a predetermined number of inner yarns 102 and a predetermined number of outer yarns 103 selected from the yarns disclosed above. The combination of the predetermined number of specific yarns in the therapeutic garment 100 disclosed herein results in energy harvesting, active heat management, and other, not heat related therapeutic features, all self-contained within the therapeutic garment 100. The combination of the predetermined number of specific yarns in the therapeutic garment 100 disclosed herein interact with each other and with the wearer and the ambient environment. The effect of all the processes performed by the yarns together, for example, generation of heat energy by an exothermic reaction, the conductive use of the heat energy by transferring the heat energy to the wearer and to the other yarns, conversion of the heat energy and ultraviolet radiation energy into far infrared radiation energy, storage of the heat energy, adsorption, heat insulation, moisture removal, etc., result in heat generation and energy harvesting and in development of a heat management system in the therapeutic garment 100 that works effectively without introducing any other external energy source or heating device into the therapeutic garment 100.

The therapeutic garment 100 disclosed herein is a self-heat generating system as the therapeutic garment 100 harvests or scavenges energy both from the therapeutic garment's 100 interaction with its wearer and from the outside environment, and converts this harvested energy into heat, which is stored and distributed within the therapeutic garment 100. The active heat management of the therapeutic garment 100 is self-generated with no additional device, for example, a heat cartridge, microwaveable gels, a battery, a charger, etc., needed for introducing and maintaining heat within the therapeutic garment 100. This is accomplished by combining at least three different types of specific yarns, selected from the yarns disclosed above, each performing the function of generating, storing, and distributing heat, respectively. The energy harvesting, heat managing, and therapeutic effects of the therapeutic garment 100 are achieved by the interaction of each yarn with the wearer and/or the ambient environment, and with another physically adjacent yarn due to the method of construction of the therapeutic garment 100. The combination of the predetermined number of yarns and the specific construction of the therapeutic garment 100 disclosed herein achieve positive results for those suffering, for example, from Raynaud's syndrome or rheumatoid arthritis, or those seeking relief from cold hands and feet in cold weather.

Figure 2:
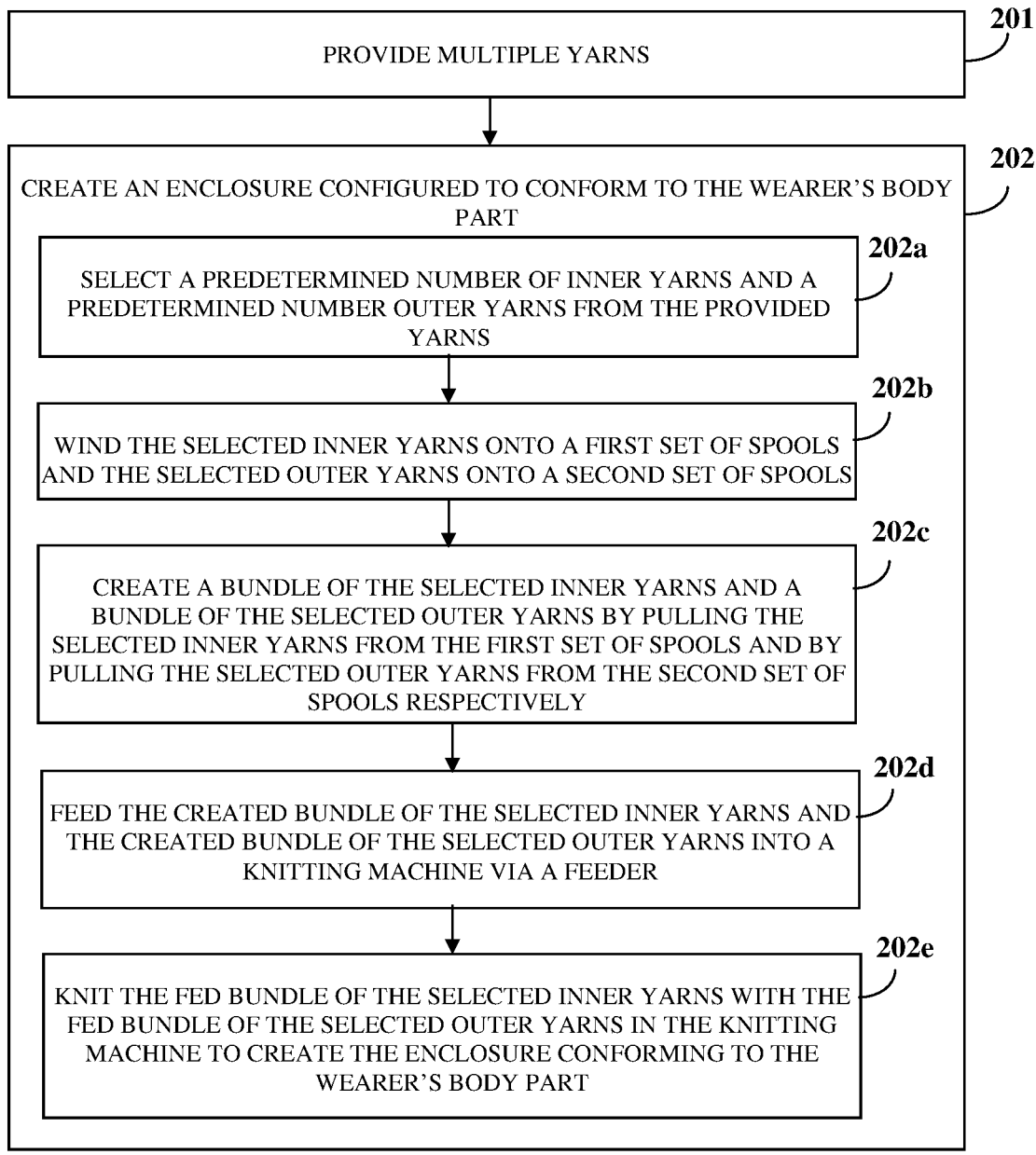
FIG. 2 illustrates a method for constructing an energy harvesting, heat managing, multi-effect therapeutic garment with self-contained heat management capabilities.

FIG. 2 illustrates a method for constructing an energy harvesting, heat managing, multi-effect therapeutic garment 100 exemplarily illustrated in FIG. 1A, with self-contained heat management capabilities. The method disclosed herein is applicable for constructing therapeutic garments of different types, for example, gloves, socks, underwear, long underwear, stockings, leggings, shirts, headgear, scarves, sweaters, slacks, etc., for any part of a wearer's body. The method disclosed herein comprises providing 201 multiple yarns as disclosed in the detailed description of FIG. 1B, and creating 202 an enclosure 101 exemplarily illustrated in FIG. 1A, configured, for example, as a glove to conform to a wearer's body part, for example, the wearer's hand. The method for creating 202 the enclosure 101 comprises selecting 202a a predetermined number of inner yarns 102 and a predetermined number of outer yarns 103 exemplarily illustrated in FIG. 1B, from the provided yarns; winding 202b the selected inner yarns 102 onto a first set of spools 301 exemplarily illustrated in FIG. 3A, and the selected outer yarns 103 onto a second set of spools 312 exemplarily illustrated in FIG. 3D; creating 202c a bundle of the selected inner yarns 102 and a bundle of the selected outer yarns 103 by pulling the selected inner yarns 102 from the first set of spools 301 and by pulling the selected outer yarns 103 from the second set of spools 312 respectively; feeding 202d the created bundle of the selected inner yarns 102 and the created bundle of the selected outer yarns 103 into a knitting machine (not shown) via a plaiting feeder 401 exemplarily illustrated in FIG. 4A; and knitting 202e the fed bundle of the selected inner yarns 102 with the fed bundle of the selected outer yarns 103 in the knitting machine to create the enclosure 101 conforming to the wearer's body part. An example of the knitting machine used in the method disclosed herein is the WHOLEGARMENT® Computerized Flat Knitting Machine, model number SWG061N2, of Shima Seiki Manufacturing, Ltd., Sakata Wakayama, Japan, developed specifically for knitting seamless clothing accessories. The knitted bundle of the selected inner yarns 102 defines the inner surface 101a of the enclosure 101 and the knitted bundle of the selected outer yarns 103 defines the outer surface 101b of the enclosure 101 as exemplarily illustrated in FIGS. 1A-1B. In an embodiment, the bundle of inner yarns 102 and the bundle of outer yarns 103 are separately made prior to the knitting of the bundle of inner yarns 102 with the bundle of outer yarns 103 to create the enclosure 101.

The bundle of inner yarns 102 plaited on the inner surface 101a of the enclosure 101 and the bundle of outer yarns 103 plaited on the outer surface 101b of the enclosure 101 comprise several different technical yarns as exemplarily illustrated in FIG. 3A and FIGS. 3C-3E. To create these bundles of yarns 102 and 103, in an embodiment, the individual yarns 102 and 103 are twisted together on yarn tubes 305 of a twisting machine 303 exemplarily illustrated in FIGS. 3A-3B and FIG. 3D. An example of the twisting machine 303 is the yarn twister of Whiting Co., Boston, Mass. This twisting machine 303 receives and twists the yarns 102 and 103 into bundles that are wound onto cones 311a and 311b exemplarily illustrated in FIG. 3A and FIG. 3D respectively, applying a predetermined amount of twist during this process. This ensures that each of the individual yarns 102 and 103 remains tight and in close proximity within their final respective bundles, while ensuring that each of the inner yarns 102 has the same amount of contact with the wearer's body part, which is necessary for maximum functionality. The winding and twisting of the outer yarns 103 ensure that each of the outer yarns 103 has an equal amount of exposure to the environment.

The knitted bundle of the selected inner yarns 102 is exposed on the inner surface 101a of the enclosure 101 and the knitted bundle of the selected outer yarns 103 is exposed on the outer surface 101b of the enclosure 101. The positions of the inner yarns 102 and the outer yarns 103 are consistently maintained relative to each other to create a uniform surface area distribution of the inner yarns 102 and the outer yarns 103 on the inner surface 101a and the outer surface 101b of the enclosure 101 respectively. The knitted bundle of the selected inner yarns 102 and the knitted bundle of the selected outer yarns 103 contact each other and cover the wearer's body part, for example, the skin on the wearer's hand when the therapeutic garment 100 is worn by the wearer. The consistent positions of the inner yarns 102 and the outer yarns 103 are maintained by a plaiting technique where the knitting machine knits one yarn of a material or more than one yarn of different materials to construct the inner surface 101a of the therapeutic garment 100, and one yarn of a material or more than one yarn of different materials to construct the outer surface 101b of the therapeutic garment 100. The plaiting technique comprises knitting with two strands of yarn where one yarn is positioned in front of the other yarn.

FIG. 3A exemplarily illustrates a yarn bundle creation machine 300 for creating a bundle of inner yarns 102 from a first set of spools 301. The inner yarns 102 comprise at least three of the yarns selected, for example, from the first yarn 102a, the second yarn 102b, the third yarn 102c, and the sixth yarn 102d as disclosed in the detailed description of FIG. 1B. For purposes of illustration, the detailed description herein refers to a selection of the first yarn 102a, the second yarn 102b, the third yarn 102c, and the sixth yarn 102d for creating a bundle of inner yarns 102; however the scope of the energy harvesting, heat managing, multi-effect therapeutic garment 100 exemplarily illustrated in FIG. 1A, and the method of construction thereof, is not limited to the selection of the first yarn 102a, the second yarn 102b, the third yarn 102c, and the sixth yarn 102d for creating the bundle of inner yarns 102, but may include a different selection of inner yarns 102, for example, the first yarn 102a, the second yarn 102b, and the third yarn 102c for creating the bundle of inner yarns 102.

The selected inner yarns 102a, 102b, 102c, and 102d are fed to the yarn bundle creation machine 300 for creating the bundle of inner yarns 102. The yarn bundle creation machine 300 comprises a first set of spools 301, a roller 302a, a winding machine 310a, and an inner yarn cone 311a. The selected inner yarns 102a, 102b, 102c, and 102d are wound around the first set of spools 301. FIG. 3A and FIG. 3C exemplarily illustrate an embodiment comprising the first yarn 102a, the second yarn 102b, the third yarn 102c, and the sixth yarn 102d wound around a first inner yarn spool 301a, a second inner yarn spool 301b, a third inner yarn spool 301c, and a fourth inner yarn spool 301d respectively. The roller 302a pulls the inner yarns 102a, 102b, 102c, and 102d from their respective spools 301a, 301b, 301c, and 301d. In an embodiment, a motor (not shown) operably coupled to the roller 302a rotates the roller 302a to pull the inner yarns 102a, 102b, 102c, and 102d from their respective spools 301a, 301b, 301c, and 301d.

Figure 3E:
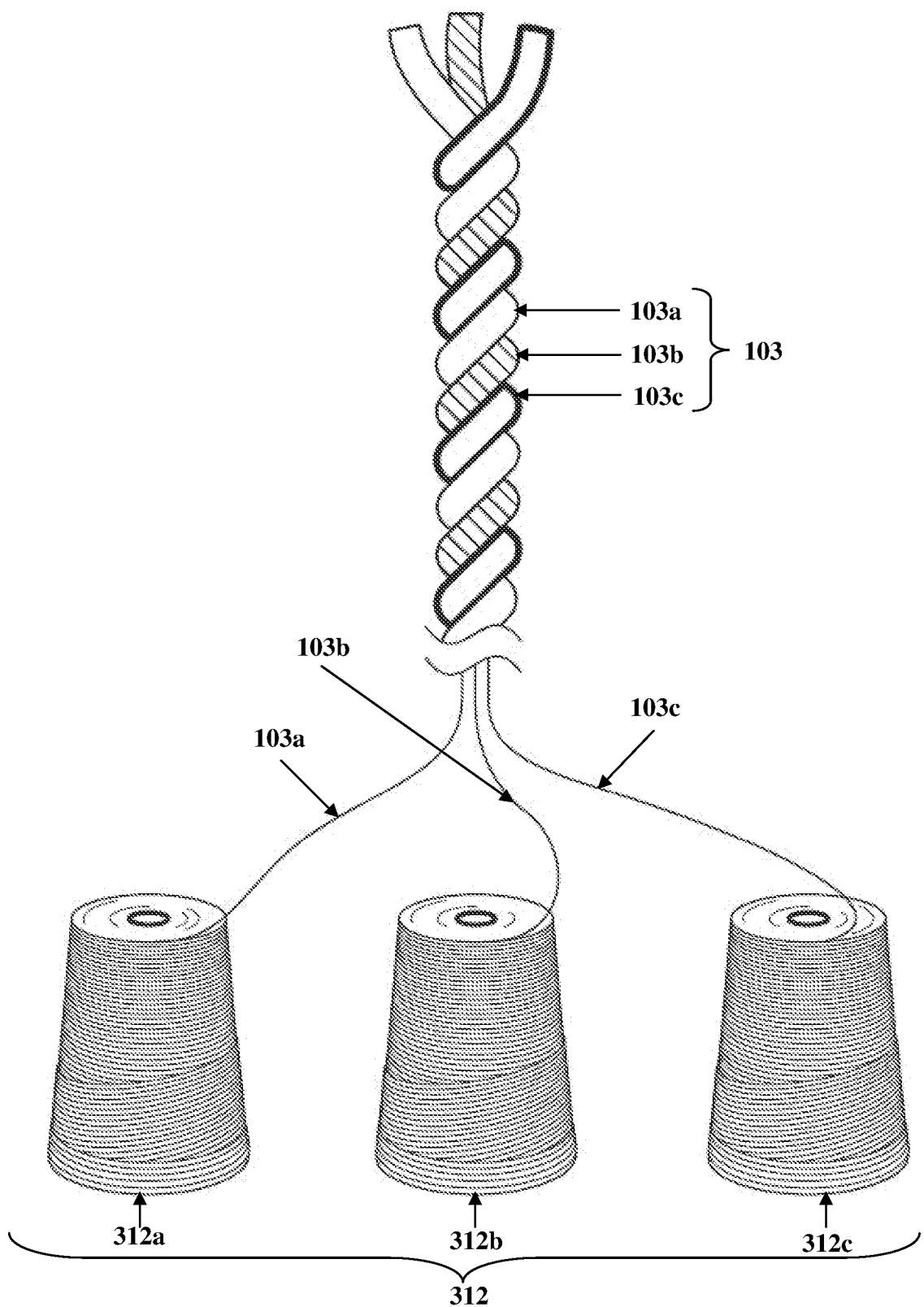
FIG. 3E exemplarily illustrates creation of a twisted bundle of outer yarns from the second set of spools.

In an embodiment, the yarn bundle creation machine 300 further comprises a twisting machine 303 comprising a yarn guide 304, a yarn tube 305, a traveler 306, and a spindle 307 as exemplarily illustrated in FIGS. 3A-3B, for twisting the inner yarns 102a, 102b, 102c, and 102d prior to knitting of the bundle of inner yarns 102 with the bundle of outer yarns 103 exemplarily illustrated in FIGS. 3D-3E, to create the enclosure 101 exemplarily illustrated in FIG. 1A. In this embodiment, the roller 302a transfers the pulled inner yarns 102a, 102b, 102c, and 102d to the yarn tube 305 of the twisting machine 303 via the yarn guide 304. The transferred inner yarns 102a, 102b, 102c, and 102d are twisted using the traveler 306 that protrudes from a lower end 305a of the yarn tube 305 to create a twisted bundle of the selected inner yarns 102, and wound on the yarn tube 305 as disclosed in the detailed description of FIG. 3B. The traveler 306 operably coupled to the spindle 307 that extends below the yarn tube 305, that is, from a bottom end 305b of the yarn tube 305, applies a predetermined amount of twist to the transferred inner yarns 102a, 102b, 102c, and 102d by spinning at a high speed, for example, about 3000 revolutions per minute (rpm) to create the twisted bundle of the selected inner yarns 102.

Twisting ensures that the individual inner yarns 102a, 102b, 102c, and 102d remain tight within the final twisted bundle of the selected inner yarns 102, and ensures that each of the inner yarns 102a, 102b, 102c, and 102d has the same amount of contact with the wearer's body part, for example, the wearer's skin, which is necessary for maximum functionality. The created twisted bundle of the selected inner yarns 102 on the yarn tube 305 is wound around the inner yarn cone 311a by the winding machine 310a for feeding the created twisted bundle of the selected inner yarns 102 into the plaiting feeder 401 exemplarily illustrated in FIG. 4A. In an embodiment, the winding machine 310a is configured as a grooved roller. An example of the winding machine 310a is the cone winder of the Foster Machine Company, Elkhart, Ind. FIG. 3A exemplarily illustrates a schematic view of the twisted bundle of the selected inner yarns 102 wound on the inner yarn cone 311a. The inner yarn cone 311a is tapered for ease of knitting on the knitting machine. The twisted bundle of the selected inner yarns 102 created from the first set of spools 301 is exemplarily illustrated in FIG. 3C.

FIG. 3B exemplarily illustrates an enlarged view of the twisting machine 303 incorporated within the yarn bundle creation machine 300 for creating the twisted bundle of inner yarns 102 exemplarily illustrated in FIG. 3A. The twisting machine 303 comprises the yarn tube 305 positioned on a movable platform 308, the traveler 306 positioned proximal to the lower end 305a of the yarn tube 305, and the spindle 307 extending from the bottom end 305b of the yarn tube 305. There is a rotating drum (not shown) near the bottom and rear of the yarn tube 305. There are belts (not shown) that are wound around the rotating drum and that connect at the bottom of the spindle 307 to rotate the spindle 307. The spindle 307, in turn, rotates the traveler 306 that is twisting the inner yarns 102, which are then wound onto the yarn tube 305 positioned above the spindle 307. The inner yarns 102 travel underneath the traveler 306, which is rotating along a ring 305c positioned around the lower end 305a of the yarn tube 305. The moving platform 308 with vertical walls 309a and 309b on opposing sides of the yarn tube 305 moves in an upward direction and a downward direction to evenly distribute the twisted inner yarns 102 onto the yarn tube 305. The twisting machine 303 exemplarily illustrated in FIG. 3B, is also used for twisting the outer yarns 103 as exemplarily illustrated in FIG. 3D.

FIG. 3C exemplarily illustrates creation of the twisted bundle of inner yarns 102 from the first set of spools 301. The first yarn 102a, the second yarn 102b, the third yarn 102c, and the sixth yarn 102d in the twisted bundle of inner yarns 102 created as disclosed in the detailed description of FIGS. 3A-3B, interact with each other and with the wearer's body part, for example, the skin of the wearer's hand as follows. The second yarn 102b receives heat energy conductively from the wearer's skin and from the first yarn 102a and converts this heat energy into far infrared radiation energy. This conversion shows a transformation in how heat is transferred from conductivity to radiation. This far infrared radiation energy penetrates below the wearer's skin, and by exciting water molecules in the wearer's body generates gentle heat. In an embodiment, the phase change material of the first yarn 102a absorbs the far infrared radiation energy, thus delaying the phase change by staying warmer longer. The first yarn 102a stores the heat energy in the embedded phase change material. The heat energy maintains the adsorption process in the third yarn 102c by delaying reaching equilibrium. The third yarn 102c adsorbs moisture based on ambient pressure and ambient temperature. When the third yarn 102c receives heat, moisture adsorbed is desorbed and escapes from the surface of the third yarn 102c. The fifth yarn 103b, being hydrophobic, carries the moisture escaped from the third yarn 102c away. The third yarn 102c cools after the desorption of the moisture. The process of adsorption and desorption is a thermodynamically reversible process. The third yarn 102c can start the adsorption anew. This heat energy and the heat energy generated by the third yarn 102c are used conductively in different methods. In a first method, the heat energy generated by the third yarn 102c is used conductively by touching the wearer's skin. In a second method, by touching the first yarn 102a, the third yarn 102c transfers the generated heat energy to the phase change material of the first yarn 102a, which stores the heat energy. In a third method, the third yarn 102c transfers the generated heat energy to the second yarn 102b, which converts this heat energy into far infrared radiation energy. The sixth yarn 102d is a carbon nanofiber that functions to maintain a uniform temperature within the combination of the first yarn 102a, the second yarn 102b, the third yarn 102c, and the outer yarns 103.

FIG. 3D exemplarily illustrates a yarn bundle creation machine 300 for creating a bundle of outer yarns 103 from a second set of spools 312. The outer yarns 103 comprise at least one of the yarns selected, for example, from the third yarn 102c, the fourth yarn 103a, the fifth yarn 103b, and the supplementary yarn 103c as disclosed in the detailed description of FIG. 1B. FIG. 3D exemplarily illustrates an embodiment comprising the fourth yarn 103a, the fifth yarn 103b, and the supplementary yarn 103c wound around a first outer yarn spool 312a, a second outer yarn spool 312b, and a third outer yarn spool 312c respectively. In an embodiment, multiple threads of the fifth yarn 103b are selected as the outer yarns 103 for creating the outer surface 101b of the enclosure 101 of the therapeutic garment 100 exemplarily illustrated in FIG. 1A. In an embodiment, the fifth yarn 103b selected as the outer yarn 103 is resistant to environmental elements of the ambient environment. For purposes of illustration, the detailed description refers to a selection of the fourth yarn 103a, the fifth yarn 103b, and the supplementary yarn 103c for creating a bundle of outer yarns 103; however the scope of the energy harvesting, heat managing, multi-effect therapeutic garment 100 exemplarily illustrated in FIG. 1A, and the method of construction thereof, is not limited to the selection of the fourth yarn 103a, the fifth yarn 103b, and the supplementary yarn 103c for creating the bundle of outer yarns 103, but may include a different selection of outer yarns 103, for example, the third yarn 102c and the fifth yarn 103b, or the fourth yarn 103a and the fifth yarn 103b, or the third yarn 102c, the fourth yarn 103a, and the fifth yarn 103b, or multiple threads of the fifth yarn 103b for creating the bundle of outer yarns 103.

The selected outer yarns 103a, 103b, and 103c are fed to the yarn bundle creation machine 300 for creating the bundle of outer yarns 103. The yarn bundle creation machine 300 comprises a second set of spools 312, a roller 302b, a winding machine 310b, and an outer yarn cone 311b. The selected outer yarns 103a, 103b, and 103c are wound around the second set of spools 312. FIGS. 3D-3E exemplarily illustrate an embodiment comprising the fourth yarn 103a, the fifth yarn 103b, and the supplementary yarn 103c wound around a first outer yarn spool 312a, a second outer yarn spool 312b, and a third outer yarn spool 312c respectively. The roller 302b pulls the outer yarns 103a, 103b, and 103c from their respective spools 312a, 312b, and 312c. In an embodiment, a motor (not shown) operably coupled to the roller 302b rotates the roller 302b to pull the outer yarns 103a, 103b, and 103c from their respective spools 312a, 312b, and 312c. In an embodiment, the yarn bundle creation machine 300 further comprises the twisting machine 303 comprising the yarn guide 304, the yarn tube 305, the traveler 306, and the spindle 307 as disclosed in the detailed description of FIG. 3B, for twisting the outer yarns 103a, 103b, and 103c prior to knitting of the bundle of inner yarns 102 exemplarily illustrated in FIG. 3A and FIG. 3C, with the bundle of outer yarns 103 to create the enclosure 101.

In this embodiment, the roller 302b transfers the pulled outer yarns 103a, 103b, and 103c to the yarn tube 305 of the twisting machine 303 via the yarn guide 304. The transferred outer yarns 103a, 103b, and 103c are twisted using the traveler 306 that protrudes from the lower end 305a of the yarn tube 305 to create a twisted bundle of the selected outer yarns 103, and wound on the yarn tube 305 as disclosed in the detailed description of FIG. 3B. The traveler 306 operably coupled to the spindle 307 that extends below the yarn tube 305, that is, from the bottom end 305b of the yarn tube 305, applies a predetermined amount of twist to the transferred outer yarns 103a, 103b, and 103c by spinning at a high speed, for example, about 3000 revolutions per minute (rpm) to create the twisted bundle of the selected outer yarns 103. Twisting ensures that the individual outer yarns 103a, 103b, and 103c remain tight within the final twisted bundle of the selected outer yarns 103, and ensures that each of the outer yarns 103a, 103b, and 103c has an equal amount of exposure to the environment. The created twisted bundle of the selected outer yarns 103 on the yarn tube 305 is wound around the outer yarn cone 311b by the winding machine 310b configured, for example, as a grooved roller, for feeding the created twisted bundle of the selected outer yarns 103 into the plaiting feeder 401 exemplarily illustrated in FIG. 4A. An example of the winding machine 310b is the cone winder of the Foster Machine Company, Elkhart, Ind. FIG. 3D exemplarily illustrates a schematic view of the twisted bundle of the selected outer yarns 103 wound on the outer yarn cone 311b. The outer yarn cone 311b is tapered for ease of knitting on the knitting machine. The twisted bundle of the selected outer yarns 103 created from the second set of spools 312 is exemplarily illustrated FIG. 3E.

FIG. 4A exemplarily illustrates feeding of the twisted bundle of inner yarns 102 and the twisted bundle of outer yarns 103 into a plaiting feeder 401. The plaiting feeder 401 comprises a first yarn guide 401a, a second yarn guide 401b, and a guide element 402 for inserting the twisted bundle of inner yarns 102 and the twisted bundle of outer yarns 103. The plating feeder 401 receives the twisted bundle of inner yarns 102 and the twisted bundle of outer yarns 103 from the inner yarn cone 311a and the outer yarn cone 311b respectively, exemplarily illustrated in FIG. 3A and FIG. 3D respectively. The plaiting feeder 401 holds the twisted bundle of inner yarns 102 and the twisted bundle of outer yarns 103 by the first yarn guide 401a and the second yarn guide 401b respectively. A fastener, for example, a bolt 401c attaches the plaiting feeder 401 to a sub carrier (not shown) that is mounted on a bar (not shown), on which the sub carrier slides back and forth. The guide element 402 comprises guides 402a and 402b for receiving the twisted bundle of inner yarns 102 and the twisted bundle of outer yarns 103 respectively, from the first yarn guide 401a and the second yarn guide 401b respectively, as exemplarily illustrated in the enlarged view of the guide element 402 shown in FIG. 4B.

FIG. 4A exemplarily illustrates an embodiment where the twisted bundle of inner yarns 102 comprises the first yarn 102a, the second yarn 102b, the third yarn 102c, and the sixth yarn 102d, and the twisted bundle of outer yarns 103 comprises the fourth yarn 103a, the fifth yarn 103b, and the supplementary yarn 103c. The twisted bundle of inner yarns 102 and the twisted bundle of outer yarns 103 are fed into the guides 402a and 402b of the guide element 402 respectively. The plaiting feeder 401 is used to feed the twisted bundle of inner yarns 102 and the twisted bundle of outer yarns 103 into a knitting machine with knitting needles 501 as exemplarily illustrated in FIGS. 5A-5C. In an embodiment, a regular feeder feeds the twisted bundle of inner yarns 102 and the twisted bundle of outer yarns 103 into the knitting machine with the knitting needles 501. The guide 402a that receives the twisted bundle of inner yarns 102 and the guide 402b that receives the twisted bundle of outer yarns 103 in the plaiting feeder 401 maintain consistent positions of the inner yarns 102 and the outer yarns 103 on the inner surface 101a and the outer surface 101b of the enclosure 101 of the therapeutic garment 100 exemplarily illustrated in FIG. 1A, respectively.

Figure 5A:
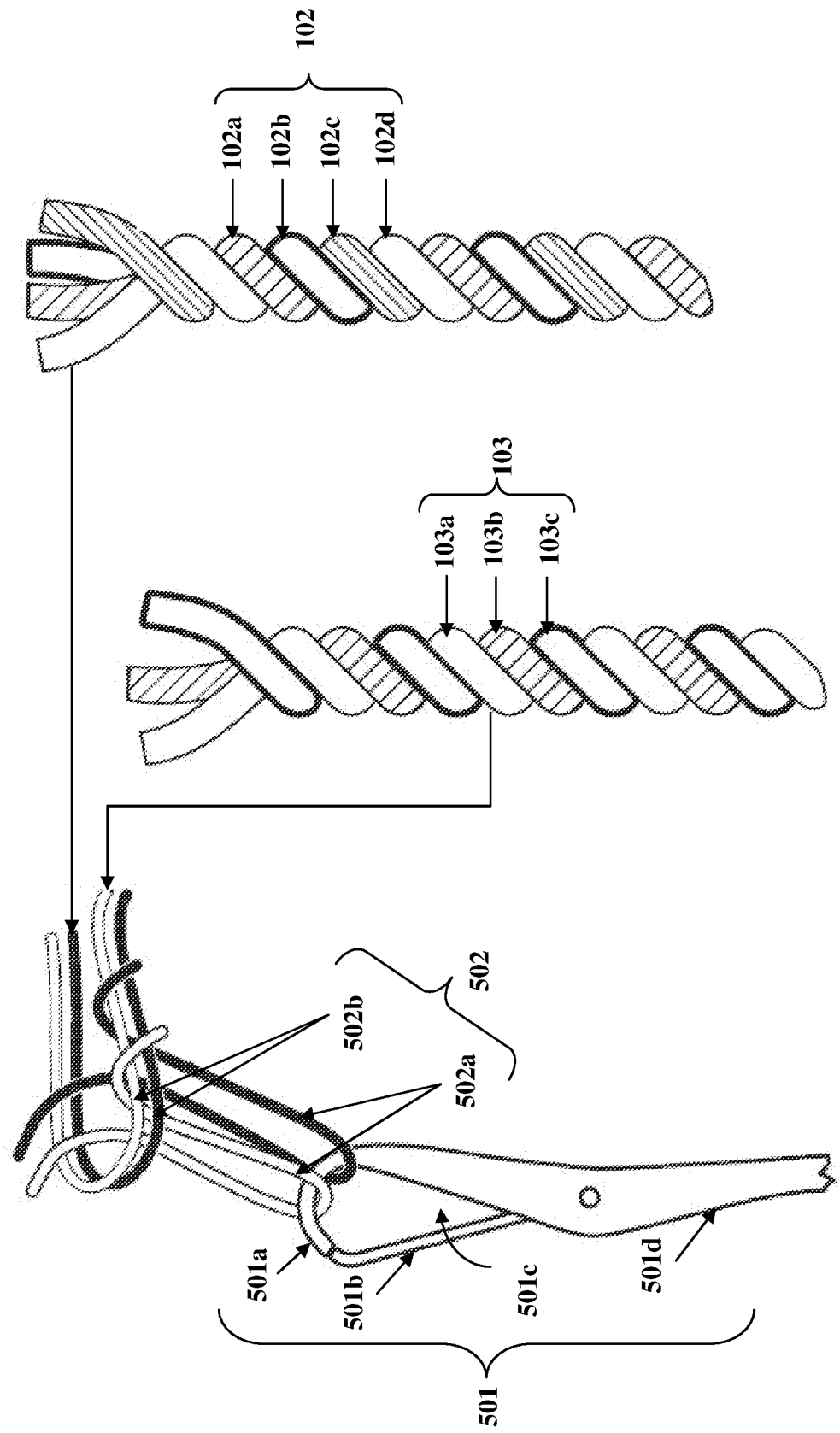
FIG. 5A exemplarily illustrates feeding of the twisted bundle of inner yarns and the twisted bundle of outer yarns into a single knitting needle.

FIG. 5A exemplarily illustrates feeding of the twisted bundle of inner yarns 102 and the twisted bundle of outer yarns 103 into a single knitting needle 501. The knitting needle 501 is, for example, a latch needle. The knitting needle 501 comprises a hook 501a, a latch blade 501b, and a stem 501d. The stem 501d of the knitting needle 501 extends from the hook 501a of the knitting needle 501. The latch blade 501b is pivotally connected to the stem 501d of the knitting needle 501. The inner yarns 102 and the outer yarns 103 are selected and twisted as disclosed in the detailed description of FIGS. 3A-3E, for creating the inner surface 101a and the outer surface 101b of the enclosure 101 of the therapeutic garment 100 exemplarily illustrated in FIG. 1A, respectively. FIG. 5A exemplarily illustrates the inner yarns 102 comprising the first yarn 102a, the second yarn 102b, the third yarn 102c, and the sixth yarn 102d, and the outer yarns 103 comprising the fourth yarn 103a, the fifth yarn 103b, and the supplementary yarn 103c. The functionality, structure, and/or material of the first yarn 102a, the second yarn 102b, the third yarn 102c, the sixth yarn 102d, the fourth yarn 103a, the fifth yarn 103b, and the supplementary yarn 103c are disclosed in the detailed description of FIG. 1B. For purposes of illustration, the detailed description of the FIG. 3A and FIG. 3B refers to the inner surface 101a of the enclosure 101 being made from a combination of the first yarn 102a, the second yarn 102b, the third yarn 102c, and the sixth yarn 102d; however the scope of the therapeutic garment 100 disclosed herein is not limited to the inner surface 101a of the enclosure 101 being made from the combination of the first yarn 102a, the second yarn 102b, the third yarn 102c, and the sixth yarn 102d, but may be made from any combination of the yarns disclosed in the detailed description of FIG. 3A and FIG. 3C. Furthermore, for purposes of illustration, the detailed description refers to the outer surface 101b of the enclosure 101 being made from a combination of the fourth yarn 103a, the fifth yarn 103b, and the supplementary yarn 103c; however the scope of the therapeutic garment 100 disclosed herein is not limited to the outer surface 101b being made from the combination of the fourth yarn 103a, the fifth yarn 103b, and the supplementary yarn 103c, but may be made from any combination of the yarns disclosed in the detailed description of FIG. 3D-3E.

The twisted bundle of inner yarns 102 and the twisted bundle of outer yarns 103 are fed into the knitting needle 501 via the plaiting feeder 401 as disclosed in the detailed description of the FIG. 4A. The plaiting feeder 401 maintains consistent positions of the inner yarns 102 and the outer yarns 103 relative to each other. The hook 501a of the knitting needle 501 holds the twisted bundle of inner yarns 102 and the twisted bundle of outer yarns 103. The latch blade 501b contacts the hook 501a, when the latch blade 501b is in a closed position. The latch blade 501b is distal to the hook 501a when the latch blade 501b is in an open position. The latch blade 501b in the closed position latches the twisted bundle of inner yarns 102 and the twisted bundle of outer yarns 103 within a space 501c defined by the hook 501a and the latch blade 501b of the knitting needle 501. In the open position, the knitting needle 501 draws loops 502 of the twisted bundle of inner yarns 102 and the twisted bundle of outer yarns 103 in a backward direction towards the stem 501d of the knitting needle 501 via the latch blade 501b and allows the hook 501a to hold the twisted bundle of inner yarns 102 and the twisted bundle of outer yarns 103. A first loop 502a of a twisted bundle of inner yarns 102 and a twisted bundle of outer yarns 103 latched in the knitting needle 501 and interwoven with a second loop 502b of a twisted bundle of inner yarns 102 and a twisted bundle of outer yarns 103 is exemplarily illustrated in FIG. 5A.

Figure 5B:
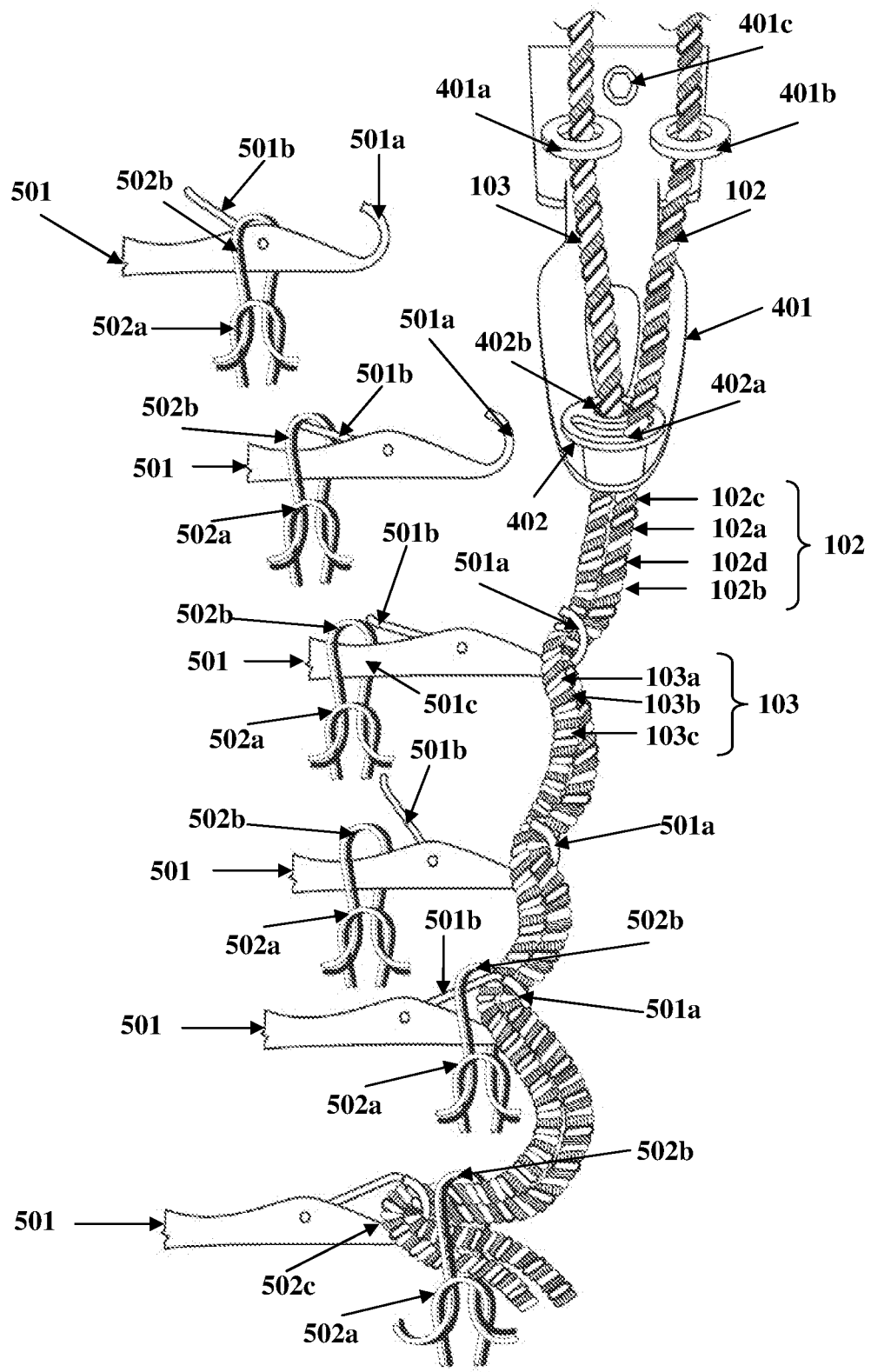
FIG. 5B exemplarily illustrates knitting of the twisted bundle of inner yarns with the twisted bundle of outer yarns using a single knitting needle.

FIG. 5B exemplarily illustrates knitting of the twisted bundle of inner yarns 102 with the twisted bundle of outer yarns 103 using a single knitting needle 501. The knitting of the twisted bundle of inner yarns 102 with the twisted bundle of outer yarns 103 is performed by plaiting. The plaiting procedure requires at least one knitting needle 501. The plaiting procedure is also called weft knitting. As disclosed in the detailed descriptions of the FIGS. 4A-4B, the plaiting feeder 401 feeds the twisted bundle of inner yarns 102 and the twisted bundle of outer yarns 103 to the knitting needle 501. The knitting needle 501 operates as disclosed in the detailed description of FIG. 5A. Consider an example where a first loop 502a and a second loop 502b of the twisted bundle of inner yarns 102 and the twisted bundle of outer yarns 103 are created by knitting using the single knitting needle 501 as exemplarily illustrated in FIG. 5B. When the knitting needle 501 moves in a forward direction, the previously created second loop 502b of the twisted bundle of inner yarns 102 and the twisted bundle of outer yarns 103 slides in a backward direction over the latch blade 501b of the knitting needle 501, thereby opening the latch blade 501b, and lands on the stem 501d of the knitting needle 501. The forward movement of the knitting needle 501 allows the hook 501a of the knitting needle 501 to grasp the twisted bundle of inner yarns 102 and the twisted bundle of outer yarns 103 fed by the plaiting feeder 401. The knitting needle 501, after grasping the twisted bundle of inner yarns 102 and the twisted bundle of outer yarns 103, moves in a backward direction to form a third loop 502c. The backward movement of the knitting needle 501 causes the previously created second loop 502b to slide on the latch blade 501b, thereby closing the latch blade 501b and latching the twisted bundle of inner yarns 102 and the twisted bundle of outer yarns 103 grasped by the hook 501a, and thereafter move onto the third loop 502c formed. Further movement of the knitting needle 501 in the backward direction causes the third loop 502c to go through the second loop 502b, after which the second loop 502b is cast off. The process continues to create a fourth loop (not shown) and so on until the enclosure 101 comprising the inner surface 101a and the outer surface 101b exemplarily illustrated in FIG. 1A, is created.

Figure 5C:
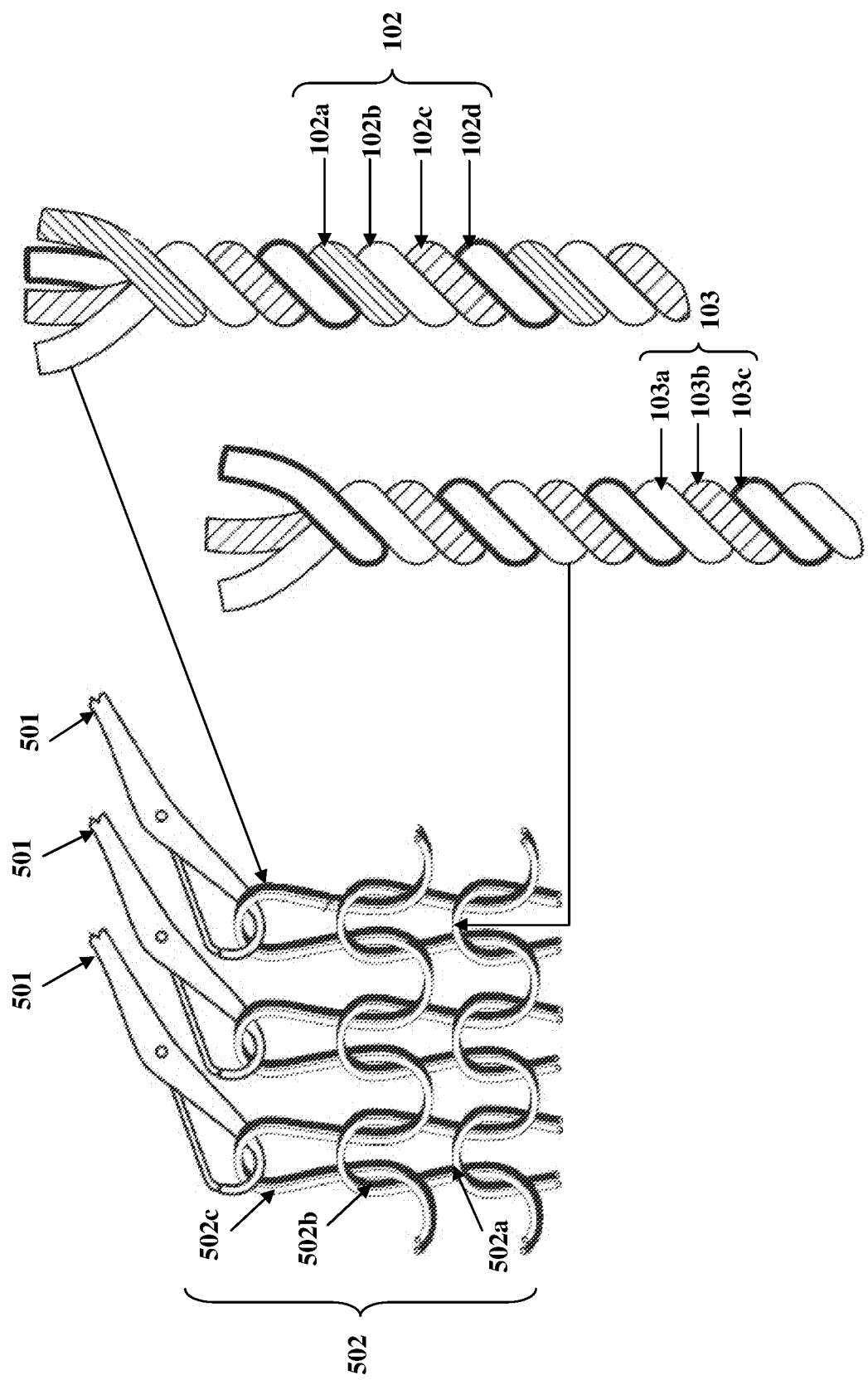
FIG. 5C exemplarily illustrates positions of the twisted bundle of inner yarns and the twisted bundle of outer yarns in a knit pattern created using multiple knitting needles.

FIG. 5C exemplarily illustrates positions of the twisted bundle of inner yarns 102 and the twisted bundle of outer yarns 103 in a knit pattern created, for example, by plaiting, using multiple knitting needles 501 of the knitting machine (not shown). Each of the knitting needles 501 operate as disclosed in the detailed description of FIG. 5A. In an embodiment, the knitting needles 501 knit the twisted bundle of inner yarns 102 and the twisted bundle of outer yarns 103 whether they come through the plaiting feeder 401 exemplarily illustrated in FIG. 4A and 5B or through a regular feeder. The method for plaiting the twisted bundle of inner yarns 102 with the twisted bundle of outer yarns 103 is disclosed in the detailed description of FIG. 5B. The predetermined number of the inner yarns 102 and the predetermined number of the outer yarns 103 defining the inner surface 101a and the outer surface 101b of the enclosure 101 of the therapeutic garment 100 exemplarily illustrated in FIG. 1A, respectively are twisted and knitted to create a uniform surface area distribution of the inner yarns 102 and the outer yarns 103 on the inner surface 101a and the outer surface 101b of the enclosure 101 respectively. The knitted bundle of inner yarns 102 and the knitted bundle of outer yarns 103 contact each other and cover the wearer's body part, for example, the wearer's skin when the therapeutic garment 100 is worn by the wearer.

Figure 6A:
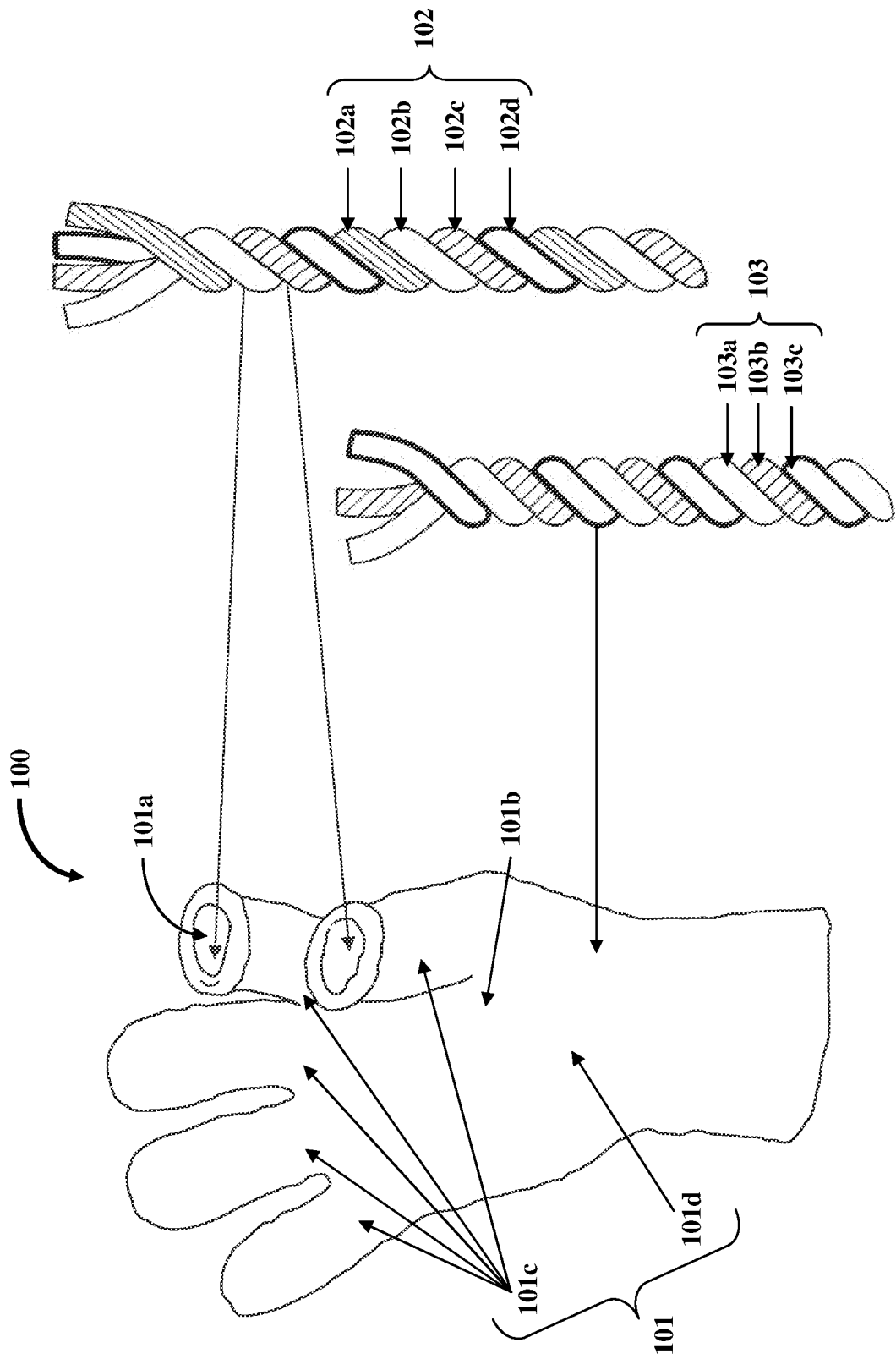
FIGS. 6A-6B exemplarily illustrate energy harvesting, heat managing, multi-effect therapeutic garments configured as therapeutic gloves and constructed in accordance with the method exemplarily illustrated in FIG. 2.
Figure 6B:
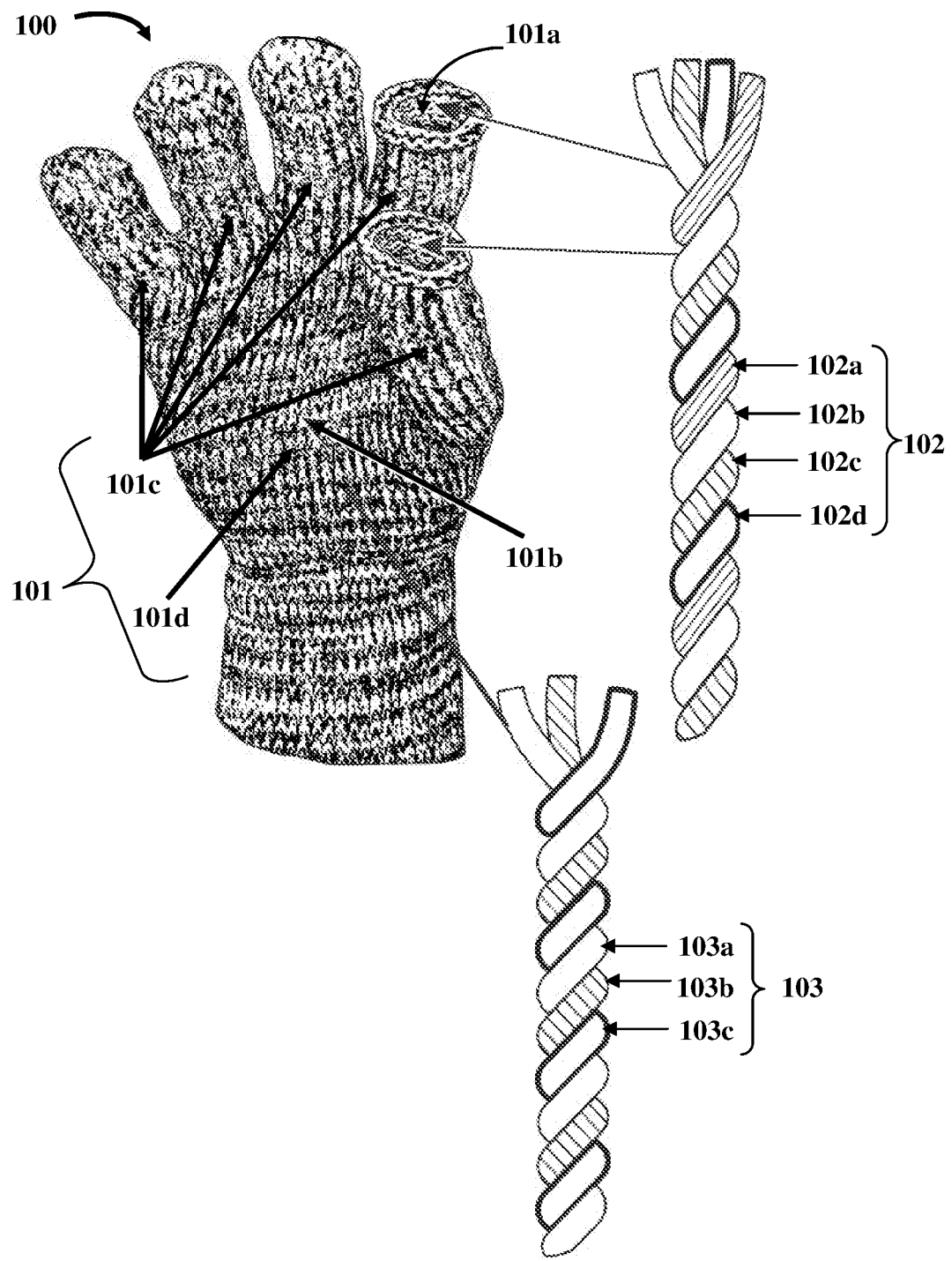

FIGS. 6A-6B exemplarily illustrate energy harvesting, heat managing, multi-effect therapeutic garments 100 configured as therapeutic gloves, herein referenced by the numeral 100, and constructed in accordance with the method exemplarily illustrated in FIG. 2 and as disclosed in the detailed description of FIG. 2. Each of the therapeutic gloves 100 exemplarily illustrated in FIGS. 6A-6B, comprises the finger section 101c and the palm section 101d collectively forming the enclosure 101 having the inner surface 101a and the outer surface 101b. The constructed therapeutic glove 100 exemplarily illustrated in FIG. 6A, is a solid colored therapeutic glove 100 where the inner yarns 102 comprising the first yarn 102a, the second yarn 102b, the third yarn 102c, and the sixth yarn 102d define the inner surface 101a proximal to the skin of the wearer's hand, and the outer yarns 103 comprising the fourth yarn 103a, the fifth yarn 103b, and the supplementary yarn 103c define the outer surface 101b distal to the skin of the wearer's hand. The constructed therapeutic glove 100 exemplarily illustrated in FIG. 6B, is a striated therapeutic glove 100 where the inner yarns 102 comprising the first yarn 102a, the second yarn 102b, the third yarn 102c, and the sixth yarn 102d define the inner surface 101a proximal to the skin of the wearer's hand, and the outer yarns 103 comprising the fifth yarn 103b, the third yarn 102c and the supplementary yarn 103c define the outer surface 101b distal to the skin of the wearer's hand.

Figure 7:
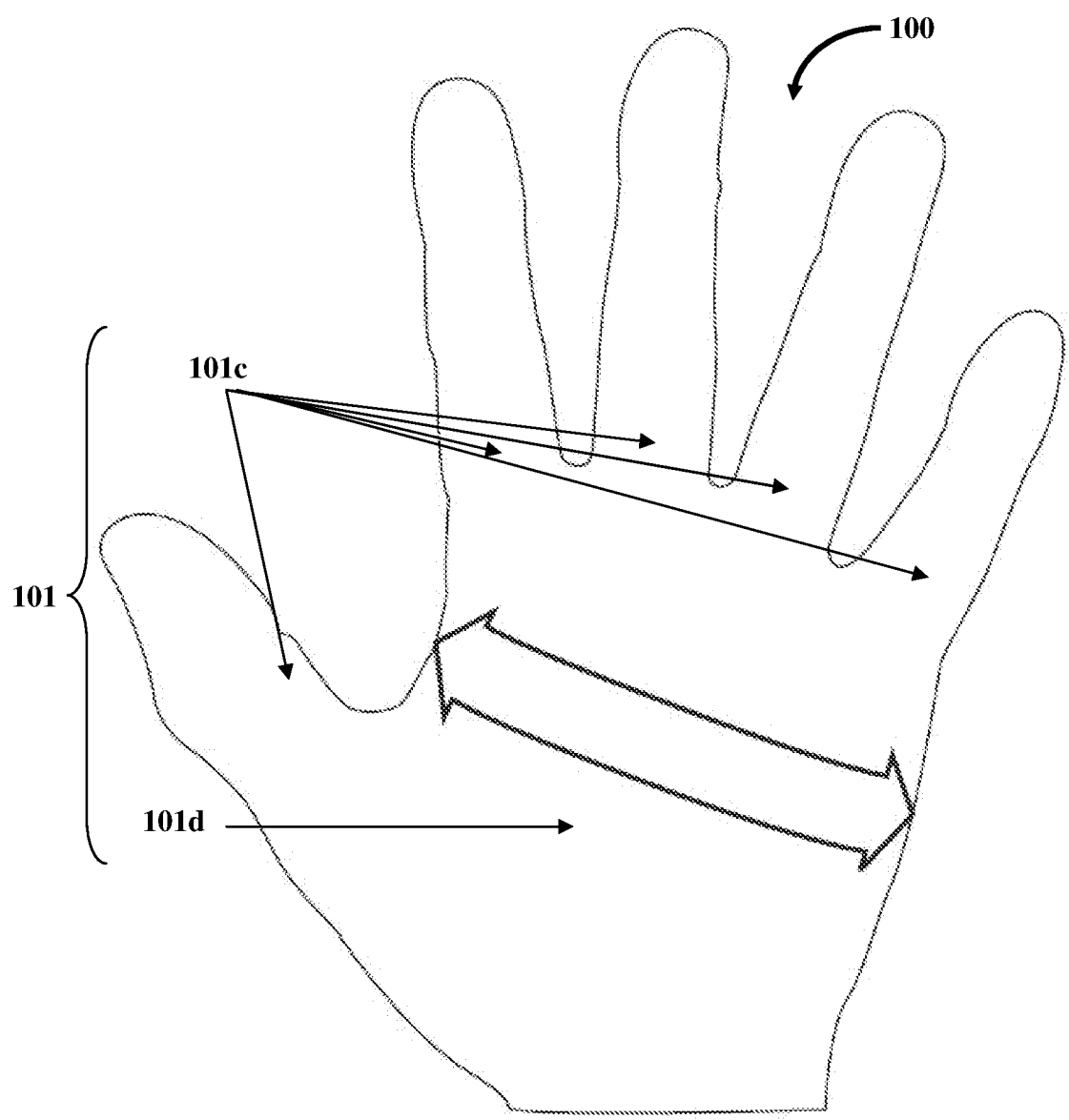
FIG. 7 exemplarily illustrates an energy harvesting, heat managing, multi-effect therapeutic garment configured as a therapeutic glove and seamlessly constructed to provide a snug fit across a palm of a wearer.

FIG. 7 exemplarily illustrates an energy harvesting, heat managing, multi-effect therapeutic garment 100 configured as a therapeutic glove and seamlessly constructed to provide a snug fit across a palm of a wearer. The palm section 101d and the finger section 101c collectively forming the enclosure 101, and the outer surface 101b of the therapeutic garment 100 configured as a therapeutic glove are exemplarily illustrated in FIG. 7. The therapeutic garment 100 is knitted in a single piece, free of seams as a complete garment or a whole garment, resulting in an improved fit on the wearer's palm with improved construction integrity. The structure of the therapeutic garment 100 provides a statistically even surface area distribution of the yarns 102 and 103 exemplarily illustrated in FIGS. 6A-6B, that cover the wearer's skin and that contact each other, which is achieved by bundling the yarns 102 and 103 prior to knitting. The therapeutic garment 100 is knit using a complete garment or three-dimensional knitting technique to create a three-dimensional seamless full garment. Computerized knitting machines perform direct movement of hundreds of knitting needles 501 exemplarily illustrated in FIG. 5C, to construct and connect several tubular knitted forms to create the therapeutic garment 100 in a single production step as per the instructions given. The complete garment knitting technique reduces wastage of materials by eliminating seam allowances and eliminates the conventional sewing technique of a material, thereby facilitating a faster time to market. Hence, the complete garment knitting technique is a cost effective technique. A predetermined number of yarns is fed to a complete garment knitting machine that manipulates the knitting needles 501. Each of the inner yarns 102 and the outer yarns 103 is controlled by a machine head capable of knitting a known or programmed knit pattern. The complete garment knitting technique can be used for knitting various forms of clothing, for example, the therapeutic garment 100.

FIGS. 8A-8B exemplarily illustrate tables containing construction data of yarns in multiple test samples of the energy harvesting, heat managing, multi-effect therapeutic garment 100 exemplarily illustrated in FIGS. 6A-6B. The construction data is represented as x (y denier), that is, x number of spools totalling y denier. FIG. 8A exemplarily illustrates a table showing construction data of the inner yarns 102 used for the construction of the test samples, for example, test sample A to test sample I along with the number of spools and the total denier. The inner yarns 102 represented in the table exemplarily illustrated in FIG. 8A, comprise the first yarn 102a, the second yarn 102b, the third yarn 102c, and the sixth yarn 102d exemplarily illustrated in FIGS. 6A-6B. FIG. 8B exemplarily illustrates a table showing construction data of the outer yarns 103 used for the construction of the test samples, for example, test sample A to test sample I along with the number of spools and the total denier. The outer yarns 103 represented in the table exemplarily illustrated in FIG. 8B, comprise the third yarn 102c, the fifth yarn 103b, and a supplementary yarn 103c made of spandex exemplarily illustrated in FIGS. 6A-6B. On performing a linear regression on the construction data, if the skin temperature increases while the wearer sits in a cold environment, the slope is a positive number. If the skin temperature remains uniform, the slope is zero. When there is a decrease in the skin temperature over a test period, the slope is a negative number. As exemplarily illustrated in FIGS. 8A-8B, the slope is a negative number for all the test samples, that is, test sample A to test sample I, that were tested as disclosed in the detailed description of FIGS. 9A-15H. The slope of the linear regression is multiplied by 1000.

FIGS. 9A-9H exemplarily illustrate a table containing skin temperature measurements of a wearer wearing test sample A and test sample B of the energy harvesting, heat managing, multi-effect therapeutic garment 100 exemplarily illustrated in FIGS. 6A-6B. Test sample A of the therapeutic garment 100 comprises the first yarn 102a, the second yarn 102b, and the third yarn 102c as the inner yarns 102 that form the inner surface 101a of the therapeutic garment 100, and the third yarn 102c, the fifth yarn 103b, and a supplementary yarn 103c made of spandex as the outer yarns 103 that form the outer surface 101b of the therapeutic garment 100 exemplarily illustrated in FIGS. 6A-6B. Test sample B of the therapeutic garment 100 comprises the first yarn 102a, the second yarn 102b, and the third yarn 102c as the inner yarns 102 that form the inner surface 101a of the therapeutic garment 100, and the third yarn 102c, the fifth yarn 103b, and the supplementary yarn 103c as the outer yarns 103 that form the outer surface 101b of the therapeutic garment 100. The skin temperature measurements of the wearer wearing the test sample A and the test sample B of the therapeutic garment 100 are taken as follows. The wearer wears the test sample A on his/her right hand and the test sample B on his/her left hand. The user is then seated in an environmental chamber with the temperature controlled, for example, at about 40 degree Fahrenheit to about 45 degree Fahrenheit. Probes are positioned on the tips of the middle fingers of the wearer's right hand and left hand, where the blood vessels close. The skin temperature on the wearer's skin is measured by the probes, for example, at fifteen second intervals, for up to one hour. The skin temperatures are analyzed as a function of elapsed time and tabulated as exemplarily illustrated in FIGS. 9A-9H. This test shows that the second yarn 102b transforms the conductive heat energy into far infrared radiation energy from the heat of the wearer's hands and from the heat in the first yarn 102a. The increase in skin temperature by wearing the test sample A and the test sample B of the therapeutic garment 100 as exemplarily illustrated by the measured data in FIGS. 9A-9H, can help persons with Raynaud's syndrome or rheumatoid arthritis, or those seeking effective protection against cold hands in cold weather.

FIGS. 10A-10H exemplarily illustrate a table containing skin temperature measurements of a wearer wearing test sample D and test sample C of the energy harvesting, heat managing, multi-effect therapeutic garment 100 exemplarily illustrated in FIGS. 6A-6B. Test sample D of the therapeutic garment 100 comprises the first yarn 102a and the third yarn 102c as the inner yarns 102 that form the inner surface 101a of the therapeutic garment 100, and the third yarn 102c, the fifth yarn 103b, and a supplementary yarn 103c made of spandex as the outer yarns 103 that form the outer surface 101b of the therapeutic garment 100 exemplarily illustrated in FIGS. 6A-6B. Test sample C of the therapeutic garment 100 comprises the first yarn 102a and the second yarn 102b as the inner yarns 102 that form the inner surface 101a of the therapeutic garment 100, and the third yarn 102c, the fifth yarn 103b, and a supplementary yarn 103c made of spandex as the outer yarns 103 that form the outer surface 101b of the therapeutic garment 100. The skin temperature measurements of the wearer wearing the test sample D and the test sample C of the therapeutic garment 100 are taken as follows. The wearer wears the test sample D on his/her right hand and the test sample C on his/her left hand. The user is then seated in an environmental chamber with the temperature controlled, for example, at about 40 degree Fahrenheit to about 45 degree Fahrenheit. Probes are positioned on the tips of the middle fingers of the wearer's right hand and left hand, where the blood vessels close. The skin temperature on the wearer's skin is measured by the probes, for example, at fifteen second intervals, for up to one hour. The skin temperatures are analyzed as a function of elapsed time and tabulated as exemplarily illustrated in FIGS. 10A-10H. This test shows that the second yarn 102b transforms the conductive heat energy into far infrared radiation energy from the heat of the wearer's hands and from the heat in the first yarn 102a. The increase in skin temperature by wearing the test sample D and the test sample C of the therapeutic garment 100 as exemplarily illustrated by the measured data in FIGS. 10A-10H, can help persons with Raynaud's syndrome or rheumatoid arthritis, or those seeking effective protection against cold hands in cold weather.

FIGS. 11A-11H exemplarily illustrate a table containing skin temperature measurements of a wearer wearing test sample E of the energy harvesting, heat managing, multi-effect therapeutic garment 100 exemplarily illustrated in FIGS. 6A-6B. Test sample E of the therapeutic garment 100 comprises the second yarn 102b and the third yarn 102c as the inner yarns 102 that form the inner surface 101a of the therapeutic garment 100, and the third yarn 102c, the fifth yarn 103b, and a supplementary yarn 103c made of spandex as the outer yarns 103 that form the outer surface 101b of the therapeutic garment 100 exemplarily illustrated in FIGS. 6A-6B. The skin temperature measurements of the wearer wearing the test sample E of the therapeutic garment 100 are taken as follows. The wearer wears the test sample E of the therapeutic garment 100 on his/her right hand. The user is then seated in an environmental chamber with the temperature controlled, for example, at about 40 degree Fahrenheit to about 45 degree Fahrenheit. A probe is positioned on the tip of the middle finger of the wearer's right hand, where the blood vessels close. The skin temperature on the wearer's skin is measured by the probe, for example, at fifteen second intervals, for up to one hour. The skin temperatures are analyzed as a function of elapsed time and tabulated as exemplarily illustrated in FIGS. 11A-11H. The increase in skin temperature by wearing the test sample E of the therapeutic garment 100 as exemplarily illustrated by the measured data in FIGS. 11A-11H, can help persons with Raynaud's syndrome or rheumatoid arthritis, or those seeking effective protection against cold hands in cold weather.

FIGS. 12A-12H exemplarily illustrate a table containing skin temperature measurements of a wearer wearing test sample F of the energy harvesting, heat managing, multi-effect therapeutic garment 100 exemplarily illustrated in FIGS. 6A-6B. Test sample F of the therapeutic garment 100 comprises the third yarn 102c as the inner yarn 102 that forms the inner surface 101a of the therapeutic garment 100, and the third yarn 102c, the fifth yarn 103b, and a supplementary yarn 103c made of spandex as the outer yarns 103 that form the outer surface 101b of the therapeutic garment 100 exemplarily illustrated in FIGS. 6A-6B. The skin temperature measurements of the wearer wearing the test sample F of the therapeutic garment 100 are taken as follows. The wearer wears the test sample F of the therapeutic garment 100 on his/her right hand. The user is then seated in an environmental chamber with the temperature controlled, for example, at about 40 degree Fahrenheit to about 45 degree Fahrenheit. A probe is positioned on the tip of the middle finger of the wearer's right hand, where the blood vessels close. The skin temperature on the wearer's skin is measured by the probe, for example, at fifteen second intervals, for up to one hour. The skin temperatures are analyzed as a function of elapsed time and tabulated as exemplarily illustrated in FIGS. 12A-12H. The increase in skin temperature by wearing the test sample F of the therapeutic garment 100 as exemplarily illustrated by the measured data in FIGS. 12A-12H, can help persons with Raynaud's syndrome or rheumatoid arthritis, or those seeking effective protection against cold hands in cold weather.

FIGS. 13A-13H exemplarily illustrate a table containing skin temperature measurements of a wearer wearing test sample G of the energy harvesting, heat managing, multi-effect therapeutic garment 100 exemplarily illustrated in FIGS. 6A-6B. Test sample G of the therapeutic garment 100 comprises the second yarn 102b as the inner yarn 102 that forms the inner surface 101a of the therapeutic garment 100, and the third yarn 102c, the fifth yarn 103b, and a supplementary yarn 103c made of spandex as the outer yarns 103 that form the outer surface 101b of the therapeutic garment 100 exemplarily illustrated in FIGS. 6A-6B. The skin temperature measurements of the wearer wearing the test sample G of the therapeutic garment 100 are taken as follows. The wearer wears the test sample G of the therapeutic garment 100 on his/her left hand. The user is then seated in an environmental chamber with the temperature controlled, for example, at about 40 degree Fahrenheit to about 45 degree Fahrenheit. A probe is positioned on the tip of the middle finger of the wearer's left hand, where the blood vessels close. The skin temperature on the wearer's skin is measured by the probe, for example, at fifteen second intervals, for up to one hour. The skin temperatures are analyzed as a function of elapsed time and tabulated as exemplarily illustrated in FIGS. 13A-13H. The increase in skin temperature by wearing the test sample G of the therapeutic garment 100 as exemplarily illustrated by the measured data in FIGS. 13A-13H, can help persons with Raynaud's syndrome or rheumatoid arthritis, or those seeking effective protection against cold hands in cold weather.

FIGS. 14A-14H exemplarily illustrate a table containing skin temperature measurements of a wearer wearing test sample H of the energy harvesting, heat managing, multi-effect therapeutic garment 100 exemplarily illustrated in FIGS. 6A-6B. Test sample H of the therapeutic garment 100 comprises the first yarn 102a as the inner yarn 102 that forms the inner surface 101a of the therapeutic garment 100, and the third yarn 102c, the fifth yarn 103b, and a supplementary yarn 103c made of spandex as the outer yarns 103 that form the outer surface 101b of the therapeutic garment 100 exemplarily illustrated in FIGS. 6A-6B. The skin temperature measurements of the wearer wearing the test sample H of the therapeutic garment 100 are taken as follows. The wearer wears the test sample H of the therapeutic garment 100 on his/her left hand. The user is then seated in an environmental chamber with the temperature controlled, for example, at about 40 degree Fahrenheit to about 45 degree Fahrenheit. A probe is positioned on the tip of the middle finger of the wearer's left hand, where the blood vessels close. The skin temperature on the wearer's skin is measured by the probe, for example, at fifteen second intervals, for up to one hour. The skin temperatures are analyzed as a function of elapsed time and tabulated as exemplarily illustrated in FIGS. 14A-14H. The increase in skin temperature by wearing the test sample H of the therapeutic garment 100 as exemplarily illustrated by the measured data in FIGS. 14A-14H, can help persons with Raynaud's syndrome or rheumatoid arthritis, or those seeking effective protection against cold hands in cold weather.

FIGS. 15A-15H exemplarily illustrate a table containing skin temperature measurements of a wearer wearing test sample I of the energy harvesting, heat managing, multi-effect therapeutic garment 100 exemplarily illustrated in FIGS. 6A-6B. Test sample I of the therapeutic garment 100 comprises the first yarn 102a, the second yarn 102b, the third yarn 102c, and the sixth yarn 102d as the inner yarns 102 that form the inner surface 101a of the therapeutic garment 100, and the third yarn 102c, the fifth yarn 103b, and a supplementary yarn 103c made of spandex as the outer yarns 103 that form the outer surface 101b of the therapeutic garment 100 exemplarily illustrated in FIGS. 6A-6B. The skin temperature measurements of the wearer wearing the test sample I are taken as follows. The wearer wears the test sample I of the therapeutic garment 100 on his/her left hand. The user is then seated in an environmental chamber with the temperature controlled, for example, at about 40 degree Fahrenheit to about 45 degree Fahrenheit. A probe is positioned on the tip of the middle finger of the wearer's left hand, where the blood vessels close. The skin temperature on the wearer's skin is measured by the probe, for example, at fifteen second intervals, for up to one hour. The skin temperatures are analyzed as a function of elapsed time and tabulated as exemplarily illustrated in FIGS. 15A-15H. By performing infrared imaging, for example, through a FLIR ONE® thermal imaging camera of Flir Systems, Inc., it is shown that heat from the sixth yarn 102d, that is, the carbon nanofiber, is conductively moved from an inner palm area that is the warmest part of the wearer's hand towards the wearer's fingers. This test also shows that the second yarn 102b transforms the conductive heat energy into far infrared radiation energy from the heat of the wearer and from the heat in the first yarn 102a. The increase in skin temperature by wearing the test sample I of the therapeutic garment 100 as exemplarily illustrated by the measured data in FIGS. 15A-15H, can help persons with Raynaud's syndrome or rheumatoid arthritis, or those seeking effective protection against cold hands in cold weather.

The foregoing examples have been provided merely for the purpose of explanation and are in no way to be construed as limiting of the therapeutic garment 100 and the method of construction thereof disclosed herein. While the therapeutic garment 100 and the method have been described with reference to various embodiments, it is understood that the words, which have been used herein, are words of description and illustration, rather than words of limitation. Further, although the therapeutic garment 100 and the method have been described herein with reference to particular means, materials, and embodiments, the therapeutic garment 100 and the method are not intended to be limited to the particulars disclosed herein; rather, the therapeutic garment 100 and the method extend to all functionally equivalent structures, methods and uses, such as are within the scope of the appended claims. Those skilled in the art, having the benefit of the teachings of this specification, may effect numerous modifications thereto and changes may be made without departing from the scope and spirit of the therapeutic garment 100 and the method disclosed herein in their aspects.

We claim:

1. An energy harvesting, heat managing, multi-effect therapeutic garment comprising:
    an enclosure, the enclosure configured to conform to a body part of a wearer, the enclosure comprising an inner surface and an outer surface, the inner surface being proximal to the body part of the wearer and the outer surface being distal to the body part of the wearer when the wearer is wearing the enclosure; and
    a combination of seven different types of yarns knitted to create the inner surface and the outer surface of the enclosure, wherein the seven different types of yarns comprise:
        a first yarn for absorbing, storing, and releasing heat energy through a phase change;
        a second yarn for converting the heat energy into far infrared radiation energy and radiating the far infrared radiation energy to the other yarns and to the body part of the wearer;
        a third yarn for adsorbing moisture from one or more of the body part of the wearer and ambient environment and generating the heat energy through an exothermic reaction between the moisture and the third yarn;
        a fourth yarn for converting ultraviolet radiation energy from sunlight into the far infrared radiation energy and radiating the far infrared radiation energy to other of the yarns and to the body part of the wearer;
        a fifth yarn for providing heat insulation and for repelling the moisture;
        a sixth yarn for conducting heat and maintaining a uniform temperature within the yarns; and
        a supplementary yarn for enhancing heat conductivity between the body part of the wearer and the inner surface of the enclosure;
    wherein a bundle of selected inner yarns is knitted with a bundle of selected outer yarns for said creation of the enclosure, wherein the knitted bundle of the selected inner yarns defines the inner surface of the enclosure, wherein a knitted bundle of the selected outer yarns defines the outer surface of the enclosure, wherein a sum of total number of yarns in the bundle of selected inner yarns and a total number of yarns in the bundle of selected outer yarns is at least six, and wherein a uniform surface area distribution of the inner yarns and the outer yarns is created on the inner surface and the outer surface of the enclosure respectively, wherein the knitted bundle of inner yarns is exposed on the inner surface of the enclosure and the knitted bundle of outer yarns is exposed on the outer surface of the enclosure, and wherein the knitted bundle of inner yarns and the knitted bundle of outer yarns contact each other and cover the body part of the wearer when the energy harvesting, heat managing, multi-effect therapeutic garment is worn by the wearer.

2. The energy harvesting, heat managing, multi-effect therapeutic garment of claim 1, wherein at least one of the yarns in the bundle of outer yarns comprises a plurality of threads of the fifth yarn.

3. The energy harvesting, heat managing, multi-effect therapeutic garment of claim 1, wherein the sixth yarn is a carbon nanofiber.

4. The energy harvesting, heat managing, multi-effect therapeutic garment of claim 1, wherein the second yarn, the third yarn, and the fourth yarn are configured to interact with each other and with one or more of the body part of the wearer and the ambient environment to harvest the heat energy.

5. The energy harvesting, heat managing, multi-effect therapeutic garment of claim 1, wherein the first yarn is configured to absorb the far infrared radiation energy from the second yarn and the fourth yarn and receive the heat energy from the third yarn.

6. The energy harvesting, heat managing, multi-effect therapeutic garment of claim 1, wherein the first yarn, in conjunction with the sixth yarn having a high heat conductivity, is further configured to maintain the uniform temperature within the yarns.

7. The energy harvesting, heat managing, multi-effect therapeutic garment of claim 1, wherein the supplementary yarn is bundled with at least one of the outer yarns to define the outer surface of the enclosure.

8. The energy harvesting, heat managing, multi-effect therapeutic garment of claim 1, wherein the bundle of inner yarns and the bundle of outer yarns are twisted prior to knitting.

9. An energy harvesting, heat managing, multi-effect therapeutic garment comprising:
an enclosure, the enclosure configured to conform to a body part of a wearer, the enclosure comprising an inner surface and an outer surface, the inner surface being proximal to the body part of the wearer and the outer surface being distal to the body part of the wearer when the wearer is wearing the enclosure; and
said enclosure created by knitting a bundle of pre-selected inner yarns and a bundle of pre-selected outer yarns, wherein the pre-selection of the inner yarns comprises selecting at least three yarns from a first yarn, a second yarn, a third yarn, and a sixth yarn, to define the inner surface of the enclosure, wherein the pre-selection of the outer yarns comprises selecting at least two yarns from the third yarn, a fourth yarn, and a fifth yarn, to define the outer surface of the enclosure, wherein a sum of a total number of yarns in the bundle of pre-selected inner yarns and a total number of yarns in the bundle of pre-selected outer yarns is at least six, wherein the yarns in the bundle of pre-selected inner yarns and the bundle of pre-selected outer yarns are configured to interact with each other, interact with a body part of the wearer, and interact with an ambient environment, for creating the energy harvesting, heat managing, multi-effect therapeutic garment, and wherein seven different types of yarns are available for the pre-selection comprising:

said first yarn configured to absorb, store, and release heat energy through a phase change;
said second yarn configured to convert the heat energy into far infrared radiation energy and radiate the far infrared radiation energy to other yarns and to the body part of the wearer;
said third yarn configured to adsorb moisture from the body part of the wearer and the ambient environment and generate the heat energy through an exothermic reaction between the moisture and the third yarn;
said fourth yarn configured to convert ultraviolet radiation energy from sunlight into the far infrared radiation energy and radiate the far infrared radiation energy to other yarns and to the body part of the wearer;
said fifth yarn configured to provide heat insulation and for repelling the moisture;
said sixth yarn configured to conduct heat and maintain a uniform temperature within the yarns; and
a supplementary yarn for enhancing heat conductivity between the body part of the wearer and the inner surface of the enclosure.

10. The energy harvesting, heat managing, multi-effect therapeutic garment of claim 9, wherein the supplementary yarn is bundled with at least one of the outer yarns to define the outer surface of the enclosure.

11. An energy harvesting, heat managing, multi-effect therapeutic garment comprising:
an enclosure, the enclosure configured to conform to a body part of a wearer, the enclosure comprising an inner surface and an outer surface, the inner surface being proximal to the body part of the wearer and the outer surface being distal to the body part of the wearer when the wearer is wearing the enclosure; and
a combination of seven different types of yarns knitted to create the inner surface and the outer surface of the enclosure, wherein a third yarn is selected as part of both the inner and outer surfaces, wherein the inner surface of the enclosure further comprises two or more yarns selected from a first yarn, a second yarn, and a sixth yarn, wherein the outer surface of the enclosure further comprises one or more yarns selected from a fourth yarn and a fifth yarn, wherein total number of the selected yarns in the enclosure is at least six, and wherein the seven different types of yarns available for selection comprise:
said first yarn for absorbing, storing, and releasing heat energy through a phase change;
said second yarn for converting the heat energy into far infrared radiation energy and radiating the far infrared radiation energy to the other yarns and to the body part of the wearer;
said third yarn for adsorbing moisture from one or more of the body part of the wearer and ambient environment and generating the heat energy through an exothermic reaction between the moisture and the third yarn;
said fourth yarn for converting ultraviolet radiation energy from sunlight into the far infrared radiation energy and radiating the far infrared radiation energy to other of the yarns and to the body part of the wearer;
said fifth yarn for providing heat insulation and for repelling the moisture;
said sixth yarn for conducting heat and maintaining a uniform temperature within the yarns; and a supplementary yarn for enhancing heat conductivity between the body part of the wearer and the inner surface of the enclosure;

wherein a bundle of selected inner yarns is knitted with a bundle of selected outer yarns for said creation of the enclosure, wherein the knitted bundle of the selected inner yarns defines the inner surface of the enclosure, wherein a knitted bundle of the selected outer yarns defines the outer surface of the enclosure, wherein a sum of total number of yarns in the bundle of selected inner yarns and a total number of yarns in the bundle of selected outer yarns is at least six, wherein a uniform surface area distribution of the inner yarns and the outer yarns is created on the inner surface and the outer surface of the enclosure respectively, wherein the knitted bundle of inner yarns is exposed on the inner surface of the enclosure and the knitted bundle of outer yarns is exposed on the outer surface of the enclosure, and wherein the knitted bundle of inner yarns and the knitted bundle of outer yarns contact each other and cover the body part of the wearer when the energy harvesting, heat managing, multi-effect therapeutic garment is worn by the wearer.

* * * * *